US009731000B2

(12) United States Patent
Pushko et al.

(10) Patent No.: US 9,731,000 B2
(45) Date of Patent: *Aug. 15, 2017

(54) MODIFIED RSV F PROTEINS AND METHODS OF THEIR USE

(71) Applicant: NOVAVAX, INC., Gaithersburg, MD (US)

(72) Inventors: Peter M. Pushko, Frederick, MD (US); Yingyun Wu, Gaithersburg, MD (US); Michael J. Massare, Mt. Airy, MD (US); Ye Liu, Laurel, MD (US); Gale Smith, Gaithersburg, MD (US); Bin Zhou, Gaithersburg, MD (US)

(73) Assignee: Novavax, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/730,805

(22) Filed: Jun. 4, 2015

(65) Prior Publication Data
US 2015/0265698 A1 Sep. 24, 2015

Related U.S. Application Data

(63) Continuation of application No. 14/221,675, filed on Mar. 21, 2014, which is a continuation of application No. 12/633,995, filed on Dec. 9, 2009, now Pat. No. 8,715,692.

(60) Provisional application No. 61/121,126, filed on Dec. 9, 2008, provisional application No. 61/169,077, filed on Apr. 14, 2009, provisional application No. 61/224,787, filed on Jul. 10, 2009.

(51) Int. Cl.
| | |
|---|---|
| *A61K 39/155* | (2006.01) |
| *C07K 14/005* | (2006.01) |
| *A61K 39/12* | (2006.01) |
| *C12N 7/00* | (2006.01) |
| *A61K 9/00* | (2006.01) |
| *A61K 39/39* | (2006.01) |
| *A61K 9/107* | (2006.01) |
| *A61K 39/00* | (2006.01) |

(52) U.S. Cl.
CPC .......... *A61K 39/155* (2013.01); *A61K 9/0019* (2013.01); *A61K 9/1075* (2013.01); *A61K 39/12* (2013.01); *A61K 39/39* (2013.01); *C07K 14/005* (2013.01); *C12N 7/00* (2013.01); *A61K 39/00* (2013.01); *A61K 2039/5258* (2013.01); *A61K 2039/54* (2013.01); *A61K 2039/545* (2013.01); *A61K 2039/55* (2013.01); *A61K 2039/55505* (2013.01); *A61K 2039/57* (2013.01); *A61K 2039/575* (2013.01); *C07K 2319/00* (2013.01); *C12N 2760/18522* (2013.01); *C12N 2760/18523* (2013.01); *C12N 2760/18534* (2013.01); *C12N 2760/18562* (2013.01); *C12N 2760/18571* (2013.01)

(58) Field of Classification Search
None
See application file for complete search history.

(56) References Cited

U.S. PATENT DOCUMENTS

| | | | | |
|---|---|---|---|---|
| 5,149,650 | A | 9/1992 | Wertz et al. | |
| 6,245,532 | B1 | 6/2001 | Smith et al. | |
| 8,563,002 | B2 * | 10/2013 | Baudoux .............. | A61K 39/155 424/192.1 |
| 8,715,692 | B2 * | 5/2014 | Pushko ................ | A61K 9/1075 424/204.1 |
| 2004/0028698 | A1 | 2/2004 | Colau et al. | |
| 2005/0142148 | A1 | 6/2005 | Fouchier et al. | |
| 2008/0233150 | A1 | 9/2008 | Smith et al. | |
| 2010/0239617 | A1 | 9/2010 | Pushko et al. | |
| 2010/0291147 | A1 | 11/2010 | Baugoux et al. | |
| 2013/0122032 | A1 | 5/2013 | Smith et al. | |
| 2014/0294879 | A1 | 10/2014 | Pushko et al. | |
| 2015/0266930 | A1 | 9/2015 | Pushko et al. | |
| 2015/0306207 | A1 | 10/2015 | Smith et al. | |
| 2015/0335730 | A1 | 11/2015 | Smith et al. | |
| 2015/0359872 | A1 | 12/2015 | Pushko et al. | |

FOREIGN PATENT DOCUMENTS

| | | |
|---|---|---|
| AU | 2014100888 A4 | 9/2014 |
| WO | WO 2005/080417 A2 | 9/2005 |
| WO | WO 2007/149490 A1 | 12/2007 |
| WO | WO 2008/114149 * | 9/2008 |
| WO | WO 2008/114149 A2 | 9/2008 |
| WO | WO 2008/133663 A2 | 11/2008 |
| WO | WO 2009/012487 A2 | 1/2009 |
| WO | WO 2009/108689 A1 | 9/2009 |
| WO | WO 2010/077717 A1 | 7/2010 |

OTHER PUBLICATIONS

Weisshaar et al. DNA and Cell Biology 2015, vol. 34, pp. 505-510.*
Murphy et al. Virus Research 1994 vol. 32, pp. 13-26.*
Anderson et al., "Intracellular processing of the human respiratory syncytial virus fusion glycoprotein: amino acid substitutions affecting folding, transport and cleavage," J. Gen. Virol. 73:1177-118 (1992).
Creemers et al., "Endoproteolytic Cleavage of Its Propeptide Is a Prerequisite for Efficient Transport of Furin Out of the Endoplasmic Reticulum," J. Biol. Chem. 270(6):2695-2702 (1995).
Genbank Accession No. AAC55970.1, "fusion glycoprotein precursor [Human respiratory syncytial virus]" (1996).
Glenn, "Recombinant, Insect Cell-Derived RSV Nanoparticle Vaccine," Novavax.com, 34 pages (Jul. 4, 2012) https://www.novavax.com/download/file/RSV nanoparticle Vaccine—MVADsJuly4(2).pdf.
Glenn et al., "Safety and immunogenicity of a Sf9 insect cell-derived respiratory syncytial virus fusion protein nanoparticle vaccine," Vaccine. Jan. 7, 2013;31(3):524-532.

(Continued)

*Primary Examiner* — Shanon A Foley
*Assistant Examiner* — Myron Hill
(74) *Attorney, Agent, or Firm* — Cooley LLP

(57) ABSTRACT

The present invention is generally related to modified or mutated respiratory syncytial virus fusion (F) proteins and methods for making and using them, including immunogenic compositions such as vaccines for the treatment and/or prevention of RSV infection.

18 Claims, 25 Drawing Sheets

(56) References Cited

OTHER PUBLICATIONS

International Search Report, 4 pages, PCT appl. No. PCT/US09/67269 (mailed Mar. 4, 2010).
International Search Report, 5 pages, PCT appl. No. PCT/US2012/057546 (mailed Jan. 22, 2013).
Ruiz-Arguello et al., "Thermostability of the human respiratory syncytial virus fusion protein before and after activation: implications for the membrane-fusion mechanism," J. Gen. Virol. 85:3677-3687 (2004).
Smith et al., "Respiratory Syncytial Virus Fusion Glycoprotein Expressed in Insect Cells Form Protein Nanoparticles That Induce Protective Immunity in Cotton Rats," PLOS ONE 7(11):e50852, 12 pages (2012).
Supplementary European Search Report, EP Appl. No. 09836751.9, 9 pages (Apr. 29, 2013).
Supplementary European Search Report, EP Appl. No. 12835033.7, 7 pages (Feb. 17, 2015).
Widjaja et al., "Recombinant Soluble Respiratory Syncytial Virus F Protein That Lacks Heptad Repeat B, Contains a GCN4 Trimerization Motif and Is Not Cleaved Displays Prefusion-Like Characteristics," PLoS One 10(6):e0130829, 19 pages (2015).
Whitehead et al., "Recombinant Respiratory Syncytial Virus (RSV) Bearing a Set of Mutations from Cold-Passaged RSV is Attenuated in Chimpanzees," J. Virol. 72(5):4467-4471 (1998).
Written Opinion of the International Searching Authority, 4 pages, PCT appl. No. PCT/US09/67269 (mailed Mar. 4, 2010).
Written Opinion of the International Searching Authority, 5 pages, PCT appl. No. PCT/US2012/057546 (mailed Jan. 22, 2013).
Lieberman et al., "Preparation and immunogenic properties of a recombinant West Nile subunit vaccine," Vaccine 25:414-423 (2007).
Parrington et al., "Baculovirus expression of the respiratory syncytial virus fusion protein using Trichoplusia ni insect cells," Virus Genes 14:63-72 (1997).
European Search Report, EP Appl. No. 16166033.7, 10 pages (Aug. 10, 2016).

* cited by examiner

FIGURE 4

Modified RSV F0 (GeneBank Assession AAB59858): pNVAX 2023 clone

FIGURE 7

BV #683 Modified RSV F0

Codon optimized
1° cleavage site inactivation (3 conservative aa changes)
Cryptic poly(A) in F2 removed
3 aa corrections to GenBank sequence
Deletion of N-terminal half of the F1 fusion domain Particle size analysis shows RSV 683 F0 forms 40 nm particles

| Clone Name | Description | WB/Coomassie | Conclusion |
|---|---|---|---|
| HRSV F0 (541) W/ BRSV F0 CT | HRSV F0 CT replaced by BRSV F0 CT | +++/- | Intracellular level is similar to 541, but inhibit BRSV M when co-infection. VLP yield is not as good as 541 |
| HRSV F0(541)+BRSV M | double genes tandem | F+++, M+++/ F-, M++ | Both intracellular and VLP yield is better than 541 co-infection with BRSV M |
| HRSV F0 (541) W/BRSV F0 CT+BRSV M | double genes tandem | F+++, M+++ F-, M++ | Both intracellular and VLP yield is better than co-infection, inhibition of BRSV M solved |
| HRSV F0 FD(G139K) | introduce G139K Point mutation (G139K) into Fusion domian | ++/- | FD(G139K) doesn't improve F0 expression |
| HRSV F0 FD(G143K) | introduce G143K Point mutation (G139K) into Fusion domian | ++/- | FD(G143K) doesn't improve F0 expression |
| HRSV F0 FD(S150K) | introduce S150K Point mutation (G139K) into Fusion domian | ++/- | FD(S150K) doesn't improve F0 expression |
| HRSV F0 FD(S153K) | introduce S153K Point mutation (G139K) into Fusion domian | ++/- | FD(S153K) doesn't improve F0 expression |
| HRSV F0 FD(S146K) | introduce S146K Point mutation (G139K) into Fusion domian | ++/- | FD(S146K) doesn't improve F0 expression |
| HRSV F0 CS mut | delete 4AA in 1'CS, change 2'CS from RARR to RANN | ++/- | very poor F0 expression |
| HRSV F0 CS mut (622) | F0 Fusion domain partial deletion(10AA) Intact Cleavage Site | ++++/ +++ | excellent F0 intracellular expression, strong band on coomassie gel |
| HRSV F0 CS mut (683) | F0 Fusion domain partial deletion(10AA) Intact Cleavage Site | ++++/ ++++ | excellent F0 intracellular expression, strong band on coomassie gel |

MODIFIED RSV F PROTEINS AND METHODS OF THEIR USE

CROSS-REFERENCE TO RELATED APPLICATIONS

This application is a continuation of U.S. Ser. No. 14/221,675, filed Mar. 21, 2014, which is a continuation of U.S. Ser. No. 12/633,995, filed Dec. 9, 2009, now U.S. Pat. No. 8,715,692, issued May 6, 2014, which claims priority to U.S. Provisional Application Ser. No. 61/121,126, filed Dec. 9, 2008, U.S. Provisional Application Ser. No. 61/169,077, filed Apr. 14, 2009, and U.S. Provisional Application Ser. No. 61/224,787, filed Jul. 10, 2009, each of which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: NOVV_034_04US_SeqList.txt, date recorded: Jun. 2, 2015; file size: 73 kilobytes).

TECHNICAL FIELD

The present invention is generally related to modified or mutated respiratory syncytial virus fusion (F) proteins and methods for making and using them, including immunogenic compositions such as vaccines for the treatment and/or prevention of RSV infection.

BACKGROUND OF THE INVENTION

Respiratory syncytial virus (RSV) is a member of the genus *Pneumovirus* of the family Paramyxoviridae. Human RSV (HRSV) is the leading cause of severe lower respiratory tract disease in young children and is responsible for considerable morbidity and mortality in humans. RSV is also recognized as an important agent of disease in immunocompromised adults and in the elderly. Due to incomplete resistance to RSV in the infected host after a natural infection, RSV may infect multiple times during childhood and adult life.

This virus has a genome comprised of a single strand negative-sense RNA, which is tightly associated with viral protein to form the nucleocapsid. The viral envelope is composed of a plasma membrane derived lipid bilayer that contains virally encoded structural proteins. A viral polymerase is packaged with the virion and transcribes genomic RNA into mRNA. The RSV genome encodes three transmembrane structural proteins, F, G, and SH, two matrix proteins, M and M2, three nucleocapsid proteins N, P, and L, and two nonstructural proteins, NS1 and NS2.

Fusion of HRSV and cell membranes is thought to occur at the cell surface and is a necessary step for the transfer of viral ribonucleoprotein into the cell cytoplasm during the early stages of infection. This process is mediated by the fusion (F) protein, which also promotes fusion of the membrane of infected cells with that of adjacent cells to form a characteristic syncytia, which is both a prominent cytopathic effect and an additional mechanism of viral spread. Accordingly, neutralization of fusion activity is important in host immunity. Indeed, monoclonal antibodies developed against the F protein have been shown to neutralize virus infectivity and inhibit membrane fusion (Calder et al., 2000, *Virology* 271: 122-131).

The F protein of RSV shares structural features and limited, but significant amino acid sequence identity with F glycoproteins of other paramyxoviruses. It is synthesized as an inactive precursor of 574 amino acids (F0) that is cotranslationally glycosylated on asparagines in the endoplasmic reticulum, where it assembles into homo-oligomers. Before reaching the cell surface, the F0 precursor is cleaved by a protease into F2 from the N terminus and F1 from the C terminus The F2 and F1 chains remains covalently linked by one or more disulfide bonds.

Immunoaffinity purified full-length F proteins have been found to accumulate in the form of micelles (also characterized as rosettes), similar to those observed with other full-length virus membrane glycoproteins (Wrigley et al., 1986, in *Electron Microscopy of Proteins*, Vol 5, p. 103-163, Academic Press, London). Under electron microscopy, the molecules in the rosettes appear either as inverted cone-shaped rods (~70%) or lollipop-shaped (~30%) structures with their wider ends projecting away from the centers of the rosettes. The rod conformational state is associated with an F glycoprotein in the pre-fusion inactivate state while the lollipop conformational state is associated with an F glycoprotein in the post-fusion, active state.

Electron micrography can be used to distinguish between the prefusion and postfusion (alternatively designated prefusogenic and fusogenic) conformations, as demonstrated by Calder et al., 2000, *Virology* 271:122-131. The prefusion conformation can also be distinguished from the fusogenic (postfusion) conformation by liposome association assays. Additionally, prefusion and fusogenic conformations can be distinguished using antibodies (e.g., monoclonal antibodies) that specifically recognize conformation epitopes present on one or the other of the prefusion or fusogenic form of the RSV F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

It has been shown previously that the F precursor is cleaved at two sites (site I, after residue 109 and site II, after residue 136), both preceded by motifs recognized by furin-like proteases. Site II is adjacent to a fusion peptide, and cleavage of the F protein at both sites is needed for membrane fusion (Gonzalez-Reyes et al., 2001, *PNAS* 98(17): 9859-9864). When cleavage is completed at both sites, it is believed that there is a transition from cone-shaped to lollipop-shaped rods.

SUMMARY OF THE INVENTION

As described herein, the present inventors have found that surprisingly high levels of expression of the fusion (F) protein can be achieved when certain modifications are made to the structure of the RSV F protein. Such modifications also unexpectedly reduce the cellular toxicity of the RSV F protein in a host cell. In addition, the modified F proteins of the present invention demonstrate an improved ability to exhibit the post-fusion "lollipop" morphology as opposed to the pre-fusion "rod" morphology. Thus, in one aspect, the modified F proteins of the present invention can also exhibit improved immunogenicity as compared to wild-type F proteins. These modifications have significant applications to the development of vaccines and methods of using said vaccines for the treatment and/or prevention of RSV. The present invention provides recombinant RSV F proteins that demonstrate increased expression, reduced cellular toxicity, and/or enhanced immunogenic properties as compared to wild-type RSV F proteins.

In one aspect, the invention provides recombinant RSV F proteins comprising modified or mutated amino acid sequences as compared to wild-type RSV F proteins. In general, these modifications or mutations increase the expression, reduce the cellular toxicity, and/or enhance the immunogenic properties of the RSV F proteins as compared to wild-type RSV F proteins. In certain exemplary embodiments, the RSV F proteins are human RSV F proteins.

The RSV F protein preferably comprises a modified or mutated amino acid sequence as compared to the wild-type RSV F protein (e.g. as exemplified in SEQ ID NO: 2). In one embodiment, the RSV F protein contains a modification or mutation at the amino acid corresponding to position P102 of the wild-type RSV F protein (SEQ ID NO: 2). In another embodiment, the RSV F protein contains a modification or mutation at the amino acid corresponding to position I379 of the wild-type RSV F protein (SEQ ID NO: 2). In another embodiment, the RSV F protein contains a modification or mutation at the amino acid corresponding to position M447 of the wild-type RSV F protein (SEQ ID NO: 2).

In one embodiment, the RSV F protein contains two or more modifications or mutations at the amino acids corresponding to the positions described above. In another embodiment, the RSV F protein contains three modifications or mutations at the amino acids corresponding to the positions described above.

In one specific embodiment, the invention is directed to RSV F proteins wherein the proline at position 102 is replaced with alanine. In another specific embodiment, the invention is directed to RSV F proteins wherein the isoleucine at position 379 is replaced with valine. In yet another specific embodiment, the invention is directed to RSV F proteins wherein the methionine at position 447 is replaced with valine. In certain embodiments, the RSV F protein contains two or more modifications or mutations at the amino acids corresponding to the positions described in these specific embodiments. In certain other embodiments, the RSV F protein contains three modifications or mutations at the amino acids corresponding to the positions described in these specific embodiments. In an exemplary embodiment, the RSV protein has the amino acid sequence described in SEQ ID NO: 4.

In one embodiment, the coding sequence of the RSV F protein is further optimized to enhance its expression in a suitable host cell. In one embodiment, the host cell is an insect cell. In an exemplary embodiment, the insect cell is an Sf9 cell.

In one embodiment, the coding sequence of the codon optimized RSV F gene is SEQ ID NO: 3. In another embodiment, the codon optimized RSV F protein has the amino acid sequence described in SEQ ID NO: 4.

In one embodiment, the RSV F protein further comprises at least one modification in the cryptic poly(A) site of F2. In another embodiment, the RSV F protein further comprises one or more amino acid mutations at the primary cleavage site (CS). In one embodiment, the RSV F protein contains a modification or mutation at the amino acid corresponding to position R133 of the wild-type RSV F protein (SEQ ID NO: 2) or the codon optimized RSV F protein (SEQ ID NO: 4). In another embodiment, the RSV F protein contains a modification or mutation at the amino acid corresponding to position R135 of the wild-type RSV F protein (SEQ ID NO: 2) or the codon optimized RSV F protein (SEQ ID NO: 4). In yet another embodiment, the RSV F protein contains a modification or mutation at the amino acid corresponding to position R136 of the wild-type RSV F protein (SEQ ID NO: 2) or the codon optimized RSV F protein (SEQ ID NO: 4).

In one specific embodiment, the invention is directed to RSV F proteins wherein the arginine at position 133 is replaced with glutamine. In another specific embodiment, the invention is directed to RSV F proteins wherein the arginine at position 135 is replaced with glutamine. In yet another specific embodiment, the invention is directed to RSV F proteins wherein arginine at position 136 is replaced with glutamine. In certain embodiments, the RSV F protein contains two or more modifications or mutations at the amino acids corresponding to the positions described in these specific embodiments. In certain other embodiment, the RSV F protein contains three modifications or mutations at the amino acids corresponding to the positions described in these specific embodiments. In an exemplary embodiment, the RSV protein has the amino acid sequence described in SEQ ID NO: 6.

In another embodiment, the RSV F protein further comprises a deletion in the N-terminal half of the fusion domain corresponding to amino acids 137-146 of SEQ ID NO: 2, SEQ ID NO: 4, and SEQ ID NO: 6. In an exemplary embodiment, the RSV F protein has the amino acid sequence described in SEQ ID NO: 8. In an alternative embodiment, the RSV F protein has the amino acid sequence described in SEQ ID NO: 10.

Further included within the scope of the invention are RSV F proteins, other than human RSV F protein (SEQ ID NO: 2), which contain alterations corresponding to those set out above. Such RSV F proteins may include, but are not limited to, the RSV F proteins from A strains of human RSV, B strains of human RSV, strains of bovine RSV, and strains of avian RSV.

In some embodiments, the invention is directed to modified or mutated RSV F proteins that demonstrate increased expression in a host cell as compared to wild-type RSV F proteins, such as the one shown by SEQ ID NO: 2. In other embodiments, the invention is directed to modified or mutated RSV F proteins that demonstrate reduced cellular toxicity in a host cell as compared to wild-type RSV F proteins, such as the one shown by SEQ ID NO: 2. In yet other embodiments, the invention is directed to modified or mutated RSV F proteins that demonstrate enhanced immunogenic properties as compared to wild-type RSV F proteins, such as the one shown by SEQ ID NO: 2.

In additional aspects, the invention provides immunogenic compositions comprising one or more modified or mutated RSV F proteins as described herein. In one embodiment, the invention provides a micelle comprised of one or more modified or mutated RSV F proteins (e.g. an RSV F micelle).

In another embodiment, the present invention provides a virus-like particle (VLP) comprising a modified or mutated RSV F protein. In some embodiments, the VLP further comprises one or more additional proteins.

In one embodiment, the VLP further comprises a matrix (M) protein. In one embodiment, the M protein is derived from a human strain of RSV. In another embodiment, the M protein is derived from a bovine strain of RSV. In other embodiments, the matrix protein may be an M1 protein from an influenza virus strain. In one embodiment, the influenza virus strain is an avian influenza virus strain. In other embodiments, the M protein may be derived from a Newcastle Disease Virus (NDV) strain.

In additional embodiments, the VLP further comprises the RSV glycoprotein G. In another embodiment, the VLP further comprises the RSV glycoprotein SH. In yet another embodiment, the VLP further comprises the RSV nucleocapsid N protein.

The modified or mutated RSV F proteins may be used for the prevention and/or treatment of RSV infection. Thus, in another aspect, the invention provides a method for eliciting an immune response against RSV. The method involves administering an immunologically effective amount of a composition containing a modified or mutated RSV F protein to a subject, such as a human or animal subject.

In another aspect, the present invention provides pharmaceutically acceptable vaccine compositions comprising a modified or mutated RSV F protein, an RSV F micelle comprising a modified or mutated RSV F protein, or a VLP comprising a modified or mutated RSV F protein.

In one embodiment, the invention comprises an immunogenic formulation comprising at least one effective dose of a modified or mutated RSV F protein. In another embodiment, the invention comprises an immunogenic formulation comprising at least one effective dose of an RSV F micelle comprising a modified or mutated RSV F protein. In yet another embodiment, the invention comprises an immunogenic formulation comprising at least one effective dose of a VLP comprising a modified or mutated RSV F protein.

In another embodiment, the invention provides for a pharmaceutical pack or kit comprising one or more containers filled with one or more of the ingredients of the vaccine formulations of the invention.

In another embodiment, the invention provides a method of formulating a vaccine or antigenic composition that induces immunity to an infection or at least one disease symptom thereof to a mammal, comprising adding to the formulation an effective dose of a modified or mutated RSV F protein, an RSV F micelle comprising a modified or mutated RSV F protein, or a VLP comprising a modified or mutated RSV F protein. In a preferred embodiment, the infection is an RSV infection.

The modified or mutated RSV F proteins of the invention are useful for preparing compositions that stimulate an immune response that confers immunity or substantial immunity to infectious agents. Thus, in one embodiment, the invention provides a method of inducing immunity to infections or at least one disease symptom thereof in a subject, comprising administering at least one effective dose of a modified or mutated RSV F protein, an RSV F micelle comprising a modified or mutated RSV F protein, or a VLP comprising a modified or mutated RSV F protein.

In yet another aspect, the invention provides a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein.

Compositions of the invention can induce substantial immunity in a vertebrate (e.g. a human) when administered to the vertebrate. Thus, in one embodiment, the invention provides a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein. In another embodiment, the invention provides a method of vaccinating a mammal against RSV comprising administering to the mammal a protection-inducing amount of a modified or mutated RSV F protein, an RSV F micelle comprising a modified or mutated RSV F protein, or a VLP comprising a modified or mutated RSV F protein.

In another embodiment, the invention comprises a method of inducing a protective antibody response to an infection or at least one symptom thereof in a subject, comprising administering at least one effective dose of a modified or mutated RSV F protein, an RSV F micelle comprising a modified or mutated RSV F protein, or a VLP comprising a modified or mutated RSV F protein.

In another embodiment, the invention comprises a method of inducing a protective cellular response to RSV infection or at least one disease symptom in a subject, comprising administering at least one effective dose of a modified or mutated RSV F protein. In another embodiment, the invention comprises a method of inducing a protective cellular response to RSV infection or at least one disease symptom in a subject, comprising administering at least one effective dose of an RSV F micelle comprising a modified or mutated RSV F protein. In yet another embodiment, the invention comprises a method of inducing a protective cellular response to RSV infection or at least one disease symptom in a subject, comprising administering at least one effective dose of a VLP, wherein the VLP comprises a modified or mutated RSV F protein.

In yet another aspect, the invention provides an isolated nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9.

In yet another aspect, the invention provides an isolated cell comprising a nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9.

In yet another aspect, the invention provides a vector comprising a nucleic acid encoding a modified or mutated RSV F protein of the invention. In an exemplary embodiment, the isolated nucleic acid encoding a modified or mutated RSV F protein is selected from the group consisting of SEQ ID NO: 3, SEQ ID NO: 5, SEQ ID NO: 7, or SEQ ID NO: 9. In one embodiment, the vector is a baculovirus vector.

In yet another aspect, the invention provides a method of making a RSV F protein, comprising (a) transforming a host cell to express a nucleic acid encoding a modified or mutated RSV F protein of the invention; and (b) culturing said host cell under conditions conducive to the production of said RSV F protein. In one embodiment, the nucleic acid encoding a modified or mutated RSV F protein is selected from the group consisting of SEQ ID NO: 3, SEQ ID NO: 5, SEQ ID NO: 7, or SEQ ID NO: 9. In another embodiment, the host cell is an insect cell. In a further embodiment, the host cell is an is an insect cell transfected with a baculovirus vector comprising a modified or mutated RSV F protein of the invention.

In yet another aspect, the invention provides a method of making a RSV F protein micelle, comprising (a) transforming a host cell to express a nucleic acid encoding a modified or mutated RSV F protein of the invention; and (b) culturing said host cell under conditions conducive to the production of said RSV F protein micelle. In one embodiment, the nucleic acid encoding a modified or mutated RSV F protein is selected from the group consisting of SEQ ID NO: 3, SEQ ID NO: 5, SEQ ID NO: 7, or SEQ ID NO: 9. In one embodiment, the host cell is an insect cell. In an exemplary embodiment, the host cell is an is an insect cell transfected with a baculovirus vector comprising a modified or mutated RSV F protein of the invention.

BRIEF DESCRIPTION OF THE FIGURES

FIG. 4 depicts sequence and structure of modified HRSV F protein BV #541 (SEQ ID NO: 6), and the sequence of the KKQKQQ cleavage site (SEQ ID NO:28).

FIG. 7 depicts structure of modified HRSV F protein BV #683, and the KKQKQQ cleavage site (SEQ ID NO: 28).

FIG. 14 depicts SDS-PAGE coomassie-stained gel (on the left) and Western Blot (on the right) analysis of modified HRSV F protein BV #622, double tandem chimeric BV #636 (BV #541+BRSV M), BV #683, BV #684 (BV #541 with YIAL L-domain), and BV #685 (BV #541 with YKKL L-domain) with or without co-expression with HRSV N and BRSV M proteins in the crude cell culture harvests (intra-cellular) samples, and structure of each analyzed modified HRSV F protein. Also featured is the KKQKQQ cleavage site (SEQ ID NO:28), and the KKRKRRcleavage site (SEQ ID NO:24).

FIG. 15 depicts SDS-PAGE coomassie-stained gel (on the left) and Western Blot (on the right) analysis of modified RSV F protein BV #622 (SEQ ID NO: 10), double tandem chimeric BV #636 (BV #541+BRSV M), BV #683 (SEQ ID NO: 8), BV #684 (BV #541 with YIAL L-domain), and BV #685 (BV #541 with YKKL L-domain) with or without co-expression with HRSV N and BRSV M proteins in the pelleted samples by 30% sucrose gradient separation, and structure of each analyzed modified HRSV F protein. Also featured is the KKQKQQ cleavage site (SEQ ID NO:28), and the KKRKRR cleavage site (SEQ ID NO:24).

Figure 16B:
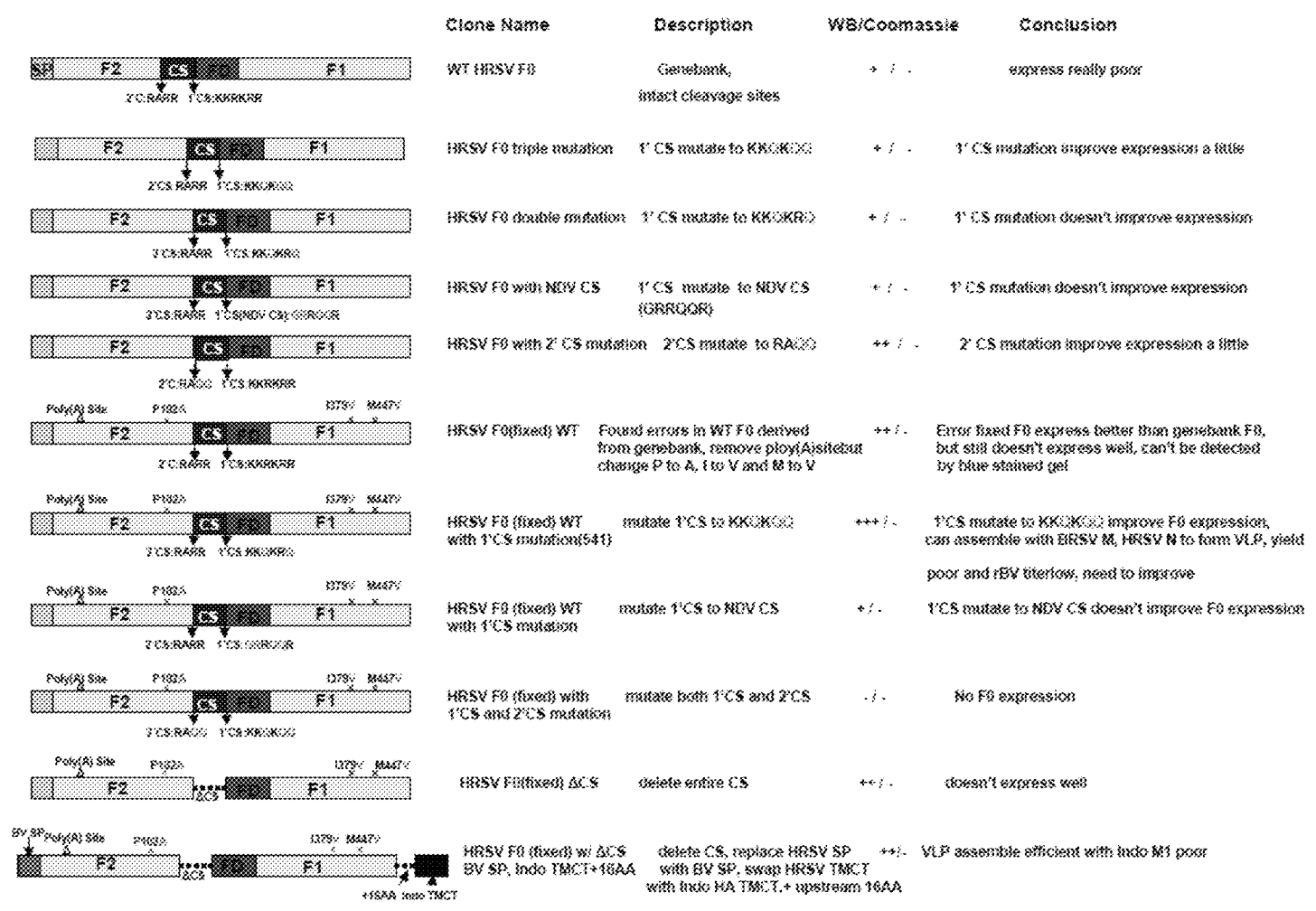

FIGS. 16A-16D depict structure, clone name, description, Western Blot and SDS-PAGE coomassie results, and conclusion for each modified RSV F protein as described in Example 9. Also featured are the KKQKQQ (SEQ ID NO:28) and the KKRKRR (SEQ ID NO:24) cleavage sites.

DETAILED DESCRIPTION

Definitions

Figure 1:
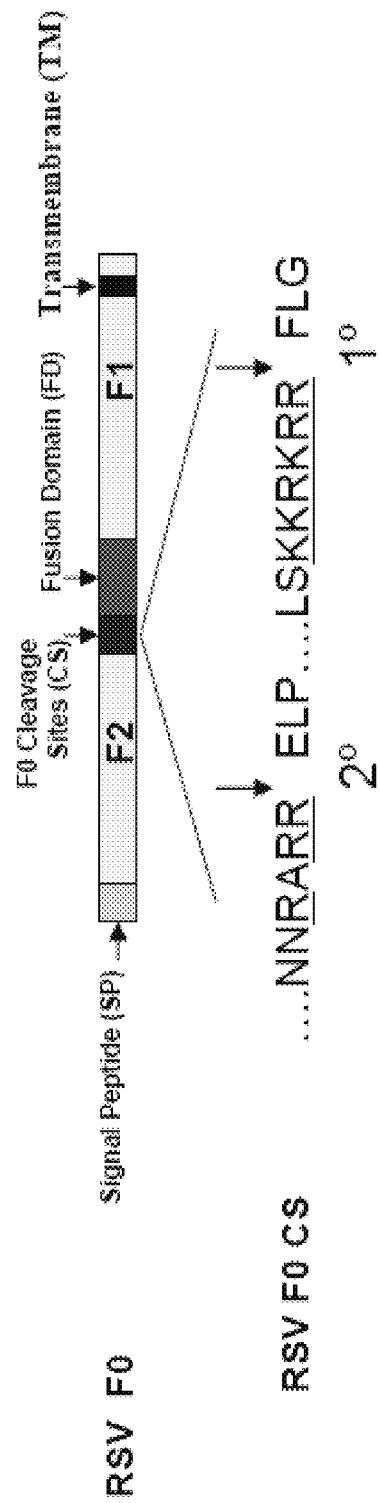
FIG. 1 depicts structure of wild type HRSV $F_0$ protein.

As used herein the term "adjuvant" refers to a compound that, when used in combination with a specific immunogen (e.g. a modified or mutated RSV F protein, an RSV F micelle comprising a modified or mutated RSV F protein, or a VLP comprising a modified or mutated RSV F protein) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

As use herein, the term "antigenic formulation" or "antigenic composition" refers to a preparation which, when administered to a vertebrate, especially a bird or a mammal, will induce an immune response.

As used herein the term "avian influenza virus" refers to influenza viruses found chiefly in birds but that can also infect humans or other animals. In some instances, avian influenza viruses may be transmitted or spread from one human to another. An avian influenza virus that infects humans has the potential to cause an influenza pandemic, i.e., morbidity and/or mortality in humans. A pandemic occurs when a new strain of influenza virus (a virus in which human have no natural immunity) emerges, spreading beyond individual localities, possibly around the globe, and infecting many humans at once.

As used herein an "effective dose" generally refers to that amount of a modified or mutated RSV F protein, an RSV F micelle comprising a modified or mutated RSV F protein, or a VLP comprising a modified or mutated RSV F protein of the invention sufficient to induce immunity, to prevent and/or ameliorate an infection or to reduce at least one symptom of an infection or disease, and/or to enhance the efficacy of another dose of a modified or mutated RSV F protein, an RSV F micelle comprising a modified or mutated RSV F protein, or a VLP comprising a modified or mutated RSV F protein. An effective dose may refer to the amount of a modified or mutated RSV F protein, an RSV F micelle comprising a modified or mutated RSV F protein, or a VLP comprising a modified or mutated RSV F protein sufficient to delay or minimize the onset of an infection or disease. An effective dose may also refer to the amount of a modified or mutated RSV F protein, an RSV F micelle comprising a modified or mutated RSV F protein, or a VLP comprising a modified or mutated RSV F protein that provides a therapeutic benefit in the treatment or management of an infection or disease. Further, an effective dose is the amount with respect to a modified or mutated RSV F protein, an RSV F micelle comprising a modified or mutated RSV F protein, or a VLP comprising a modified or mutated RSV F protein of the invention alone, or in combination with other therapies, that provides a therapeutic benefit in the treatment or management of an infection or disease. An effective dose may also be the amount sufficient to enhance a subject's (e.g., a human's) own immune response against a subsequent exposure to an infectious agent or disease. Levels of immunity can be monitored, e.g., by measuring amounts of neutralizing secretory and/or serum antibodies, e.g., by plaque neutralization, complement fixation, enzyme-linked immunosorbent, or microneutralization assay, or by measuring cellular responses, such as, but not limited to cytotoxic T cells, antigen presenting cells, helper T cells, dendritic cells and/or other cellular responses. T cell responses can be monitored, e.g., by measuring, for example, the amount of $CD4^+$ and $CD8^+$ cells present using specific markers by fluorescent flow cytometry or T cell assays, such as but not limited to T-cell proliferation assay, T-cell cytotoxic assay, TETRAMER assay, and/or ELISPOT assay. In the case of a vaccine, an "effective dose" is one that prevents disease and/or reduces the severity of symptoms.

As used herein, the term "effective amount" refers to an amount of a modified or mutated RSV F protein, an RSV F micelle comprising a modified or mutated RSV F protein, or a VLP comprising a modified or mutated RSV F protein necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to a modified or mutated RSV F protein, an RSV F micelle comprising a modified or mutated RSV F protein, or a VLP comprising a modified or mutated RSV F protein of the invention. The term is also synonymous with "sufficient amount."

As used herein, the term "expression" refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA. In the context of the present invention, the term also encompasses the yield of RSV F gene mRNA and RSV F proteins achieved following expression thereof.

As used herein, the term "F protein" or "Fusion protein" or "F protein polypeptide" or "Fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. Numerous RSV Fusion and Attachment proteins have been described and are known to those of skill in the art. WO/2008/114149, which is herein incorporated by reference in its entirety, sets out exemplary F and G protein variants (for example, naturally occurring variants).

As used herein, the terms "immunogens" or "antigens" refer to substances such as proteins, peptides, peptides, nucleic acids that are capable of eliciting an immune response. Both terms also encompass epitopes, and are used interchangeably.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons (IFN-γ), interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As use herein, the term "immunogenic formulation" refers to a preparation which, when administered to a vertebrate, e.g. a mammal, will induce an immune response.

As use herein, the term "infectious agent" refers to microorganisms that cause an infection in a vertebrate. Usually, the organisms are viruses, bacteria, parasites, protozoa and/or fungi.

As used herein, the terms "mutated," "modified," "mutation," or "modification" indicate any modification of a nucleic acid and/or polypeptide which results in an altered nucleic acid or polypeptide. Mutations include, for example, point mutations, deletions, or insertions of single or multiple residues in a polynucleotide, which includes alterations arising within a protein-encoding region of a gene as well as alterations in regions outside of a protein-encoding sequence, such as, but not limited to, regulatory or promoter sequences. A genetic alteration may be a mutation of any type. For instance, the mutation may constitute a point mutation, a frame-shift mutation, an insertion, or a deletion of part or all of a gene. In some embodiments, the mutations are naturally-occurring. In other embodiments, the mutations are the results of artificial mutation pressure. In still other embodiments, the mutations in the RSV F proteins are the result of genetic engineering.

As used herein, the term "multivalent" refers to compositions which have one or more antigenic proteins/peptides or immunogens against multiple types or strains of infectious agents or diseases.

As used herein, the term "pharmaceutically acceptable vaccine" refers to a formulation which contains a modified or mutated RSV F protein, an RSV F micelle comprising a modified or mutated RSV F protein, or a VLP comprising a modified or mutated RSV F protein of the present invention, which is in a form that is capable of being administered to a vertebrate and which induces a protective immune response sufficient to induce immunity to prevent and/or ameliorate an infection or disease, and/or to reduce at least one symptom of an infection or disease, and/or to enhance the efficacy of another dose of a modified or mutated RSV F protein, an RSV F micelle comprising a modified or mutated RSV F protein, or a VLP comprising a modified or mutated RSV F protein. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

As used herein, the phrase "protective immune response" or "protective response" refers to an immune response mediated by antibodies against an infectious agent or disease, which is exhibited by a vertebrate (e.g., a human), that prevents or ameliorates an infection or reduces at least one disease symptom thereof Modified or mutated RSV F proteins, RSV F micelles comprising a modified or mutated RSV F protein, or VLPs comprising a modified or mutated RSV F protein of the invention can stimulate the production of antibodies that, for example, neutralize infectious agents, blocks infectious agents from entering cells, blocks replication of the infectious agents, and/or protect host cells from infection and destruction. The term can also refer to an immune response that is mediated by T-lymphocytes and/or other white blood cells against an infectious agent or disease, exhibited by a vertebrate (e.g., a human), that prevents or ameliorates infection or disease, or reduces at least one symptom thereof.

As use herein, the term "vertebrate" or "subject" or "patient" refers to any member of the subphylum cordata, including, without limitation, humans and other primates, including non-human primates such as chimpanzees and other apes and monkey species. Farm animals such as cattle, sheep, pigs, goats and horses; domestic mammals such as dogs and cats; laboratory animals including rodents such as mice, rats (including cotton rats) and guinea pigs; birds, including domestic, wild and game birds such as chickens, turkeys and other gallinaceous birds, ducks, geese, and the like are also non-limiting examples. The terms "mammals" and "animals" are included in this definition. Both adult and newborn individuals are intended to be covered. In particular, infants and young children are appropriate subjects or patients for a RSV vaccine.

As used herein, the term "virus-like particle" (VLP) refers to a structure that in at least one attribute resembles a virus but which has not been demonstrated to be infectious. Virus-like particles in accordance with the invention do not carry genetic information encoding for the proteins of the virus-like particles. In general, virus-like particles lack a viral genome and, therefore, are noninfectious. In addition, virus-like particles can often be produced in large quantities by heterologous expression and can be easily purified.

As used herein, the term "chimeric VLP" refers to VLPs that contain proteins, or portions thereof, from at least two different infectious agents (heterologous proteins). Usually, one of the proteins is derived from a virus that can drive the formation of VLPs from host cells. Examples, for illustrative purposes, are the BRSV M protein and/or the HRSV G or F proteins. The terms RSV VLPs and chimeric VLPs can be used interchangeably where appropriate.

As used herein, the term "vaccine" refers to a preparation of dead or weakened pathogens, or of derived antigenic determinants that is used to induce formation of antibodies or immunity against the pathogen. A vaccine is given to provide immunity to the disease, for example, influenza, which is caused by influenza viruses. In addition, the term "vaccine" also refers to a suspension or solution of an immunogen (e.g. a modified or mutated RSV F protein, an RSV F micelle comprising a modified or mutated RSV F protein, or a VLP comprising a modified or mutated RSV F protein) that is administered to a vertebrate to produce protective immunity, i.e., immunity that prevents or reduces the severity of disease associated with infection. The present invention provides for vaccine compositions that are immunogenic and may provide protection against a disease associated with infection.

RSV F Proteins

Two structural membrane proteins, F and G proteins, are expressed on the surface of RSV, and have been shown to be targets of neutralizing antibodies (Sullender, W., 2000, *Clinical Microbiology Review* 13, 1-15). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein can neutralize virus or block entry of the virus into the cell or prevent syncytia formation. Although antigenic and structural differences between A and B subtypes have been described for both the G and F proteins, the more significant antigenic differences reside on the G protein, where amino acid sequences are only 53% homologous and antigenic relatedness is 5% (Walsh et al. (1987) J. Infect. Dis. 155, 1198-1204; and Johnson et al. (1987) Proc. Natl. Acad. Sci. USA 84, 5625-5629). Conversely, antibodies raised to the F protein show a high degree of cross-reactivity among subtype A and B viruses.

The RSV F protein directs penetration of RSV by fusion between the virion's envelope protein and the host cell plasma membrane. Later in infection, the F protein expressed on the cell surface can mediate fusion with neighboring cells to form syncytia. The F protein is a type I transmembrane surface protein that has a N-terminal cleaved signal peptide and a membrane anchor near the C-terminus. RSV F is synthesized as an inactive $F_0$ precursor that assembles into a homotrimer and is activated by cleavage in the trans-Golgi complex by a cellular endoprotease to yield two disulfide-linked subunits, $F_1$ and $F_2$ subunits. The N-terminus of the $F_1$ subunit that is created by cleavage contains a hydrophobic domain (the fusion peptide) that inserts directly into the target membrane to initiate fusion. The $F_1$ subunit also contains heptad repeats that associate during fusion, driving a conformational shift that brings the viral and cellular membranes into close proximity (Collins and Crowe, 2007, Fields Virology, $5^{th}$ ed., D. M Kipe et al., Lipincott, Williams and Wilkons, p. 1604). SEQ ID NO: 2 (GenBank Accession No. AAB59858) depicts a representative RSV F protein, which is encoded by the gene shown in SEQ ID NO: 1 (GenBank Accession No. M11486).

In nature, the RSV F protein is expressed as a single polypeptide precursor, 574 amino acids in length, designated F0. In vivo, F0 oligomerizes in the endoplasmic reticulum and is proteolytically processed by a furin protease at two conserved furin consensus sequences (furin cleavage sites), RARR (SEQ ID NO: 23) (secondary) and KKRKRR (SEQ ID NO: 24) (primary) to generate an oligomer consisting of two disulfide-linked fragments. The smaller of these fragments is termed F2 and originates from the N-terminal portion of the F0 precursor. It will be recognized by those of skill in the art that the abbreviations F0, F1 and F2 are commonly designated $F_0$, $F_1$ and $F_2$ in the scientific literature. The larger, C-terminal F1 fragment anchors the F protein in the membrane via a sequence of hydrophobic amino acids, which are adjacent to a 24 amino acid cytoplasmic tail. Three F2-F1 dimers associate to form a mature F protein, which adopts a metastable prefusogenic ("prefusion") conformation that is triggered to undergo a conformational change upon contact with a target cell membrane. This conformational change exposes a hydrophobic sequence, known as the fusion peptide, which associates with the host cell membrane and promotes fusion of the membrane of the virus, or an infected cell, with the target cell membrane.

The F1 fragment contains at least two heptad repeat domains, designated HRA and HRB, and is situated in proximity to the fusion peptide and transmembrane anchor domains, respectively. In the prefusion conformation, the F2-F1 dimer forms a globular head and stalk structure, in which the HRA domains are in a segmented (extended) conformation in the globular head. In contrast, the HRB domains form a three-stranded coiled coil stalk extending from the head region. During transition from the prefusion to the postfusion conformations, the HRA domains collapse and are brought into proximity to the HRB domains to form an anti-parallel six helix bundle. In the postfusion state the fusion peptide and transmembrane domains are juxtaposed to facilitate membrane fusion.

Although the conformational description provided above is based on molecular modeling of crystallographic data, the structural distinctions between the prefusion and postfusion conformations can be monitored without resort to crystallography. For example, electron micrography can be used to distinguish between the prefusion and postfusion (alternatively designated prefusogenic and fusogenic) conformations, as demonstrated by Calder et al., *Virology*, 271:122-131 (2000) and Morton et al., *Virology*, 311: 275-288, which are incorporated herein by reference for the purpose of their technological teachings. The prefusion conformation can also be distinguished from the fusogenic (post-fusion) conformation by liposome association assays as described by Connolly et al, *Proc. Natl. Acad. Sci. USA*, 103:17903-17908 (2006), which is also incorporated herein by reference for the purpose of its technological teachings. Additionally, prefusion and fusogenic conformations can be distinguished using antibodies (e.g., monoclonal antibodies) that specifically recognize conformation epitopes present on one or the other of the prefusion or fusogenic form of the RSV F protein, but not on the other form. Such conformation epitopes can be due to preferential exposure of an antigenic determinant on the surface of the molecule. Alternatively, conformational epitopes can arise from the juxtaposition of amino acids that are non-contiguous in the linear polypeptide.

Modified or Mutated RSV F Proteins

The present inventors have found that surprisingly high levels of expression of the fusion (F) protein can be achieved when specific modifications are made to the structure of the RSV F protein. Such modifications also unexpectedly reduce the cellular toxicity of the RSV F protein in a host cell. In addition, the modified F proteins of the present invention demonstrate an improved ability to exhibit the post-fusion "lollipop" morphology as opposed to the prefusion "rod" morphology. Thus, in one aspect, the modified F proteins of the present invention can also exhibit improved (e.g. enhanced) immunogenicity as compared to wild-type F proteins (e.g. exemplified by SEQ ID NO: 2, which corresponds to GenBank Accession No. AAB59858). These modifications have significant applications to the development of vaccines and methods of using said vaccines for the treatment and/or prevention of RSV.

In accordance with the invention, any number of mutations can be made to native or wild-type RSV F proteins, and in a preferred aspect, multiple mutations can be made to result in improved expression and/or immunogenic properties as compared to native or wild-type RSV F proteins. Such mutations include point mutations, frame shift mutations, deletions, and insertions, with one or more (e.g., one, two, three, or four, etc.) mutations preferred.

The native F protein polypeptide can be selected from any F protein of an RSV A strain, RSV B strain, HRSV A strain, HRSV B strain, BRSV strain, or avian RSV strain, or from variants thereof (as defined above). In certain exemplary embodiments, the native F protein polypeptide is the F protein represented by SEQ ID NO: 2 (GenBank Accession No AAB59858). To facilitate understanding of this disclosure, all amino acid residue positions, regardless of strain, are given with respect to (that is, the amino acid residue position corresponds to) the amino acid position of the exemplary F protein. Comparable amino acid positions of the F protein from other RSV strains can be determined easily by those of ordinary skill in the art by aligning the amino acid sequences of the selected RSV strain with that of the exemplary sequence using readily available and well-known alignment algorithms (such as BLAST, e.g., using default parameters). Numerous additional examples of F protein polypeptides from different RSV strains are disclosed in WO/2008/114149 (which is incorporated herein by reference in its entirety). Additional variants can arise through genetic drift, or can be produced artificially using site directed or random mutagenesis, or by recombination of two or more preexisting variants. Such additional variants are also suitable in the context of the modified or mutated RSV F proteins disclosed herein.

Mutations may be introduced into the RSV F proteins of the present invention using any methodology known to those skilled in the art. Mutations may be introduced randomly by, for example, conducting a PCR reaction in the presence of manganese as a divalent metal ion cofactor. Alternatively, oligonucleotide directed mutagenesis may be used to create the mutant or modified RSV F proteins which allows for all possible classes of base pair changes at any determined site along the encoding DNA molecule. In general, this technique involves annealing an oligonucleotide complementary (except for one or more mismatches) to a single stranded nucleotide sequence coding for the RSV F protein of interest. The mismatched oligonucleotide is then extended by DNA polymerase, generating a double-stranded DNA molecule which contains the desired change in sequence in one strand. The changes in sequence can, for example, result in the deletion, substitution, or insertion of an amino acid. The double-stranded polynucleotide can then be inserted into an appropriate expression vector, and a mutant or modified polypeptide can thus be produced. The above-described oligonucleotide directed mutagenesis can, for example, be carried out via PCR.

Additional RSV Proteins

The invention also encompasses RSV virus-like particles (VLPs) comprising a modified or mutated RSV F protein that can be formulated into vaccines or antigenic formulations for protecting vertebrates (e.g. humans) against RSV infection or at least one disease symptom thereof In some embodiments, the VLP comprising a modified or mutated RSV F protein further comprises additional RSV proteins, such as M, N, G, and SH. In other embodiments, the VLP comprising a modified or mutated RSV F protein further comprises proteins from heterologous strains of virus, such as influenza virus proteins HA, NA, and M1. In one embodiment, the influenza virus protein M1 is derived from an avian influenza virus strain.

RSV N protein binds tightly to both genomic RNA and the replicative intermediate anti-genomic RNA to form RNAse resistant nucleocapsid. SEQ ID NOs: 16 (wild-type) and 18 (codon-optimized) depict representative amino acid sequences of the RSV N protein and SEQ ID NOs: 15 (wild-type) and 17 (codon-optimized) depict representative nucleic acid sequences encoding the RSV N protein. Encompassed in this invention are RSV N proteins that are at least about 20%, about 30%, about 40%, about 50%, about 60%, about 70% or about 80%, about 85%, about 90%, about 95%, about 96%, about 97%, about 98% or about 99% identical to SEQ ID NO: 18, and all fragments and variants (including chimeric proteins) thereof.

RSV M protein is a non-glycosylated internal virion protein that accumulates in the plasma membrane that interacts with RSV F protein and other factors during virus morphogenesis. In certain preferred embodiments, the RSV M protein is a bovine RSV (BRSV) M protein. SEQ ID NOs: 12 (wild-type) and 14 (codon-optimized) depict representative amino acid sequences of the BRSV M protein and SEQ ID NOs: 11 (wild-type) and 13 (codon-optimized) depict representative nucleic acid sequences encoding the BRSV M protein. Encompassed in this invention are RSV (including, but not limited to, BRSV) M proteins that are at least about 20%, about 30%, about 40%, about 50%, about 60%, about 70% or about 80%, about 85%, about 90%, about 95%, about 96%, about 97%, about 98% or about 99% identical to SEQ ID NOs: 12 and 14, and all fragments and variants (including chimeric proteins) thereof.

RSV G protein is a type II transmembrane glycoprotein with a single hydrophobic region near the N-terminal end that serves as both an uncleaved signal peptide and a membrane anchor, leaving the C-terminal two-thirds of the molecule oriented externally. RSV G is also expressed as a secreted protein that arises from translational initiation at the second AUG in the ORF (at about amino acid 48), which lies within the signal/anchor. Most of the ectodomain of RSV G is highly divergent between RSV strains (Id., p. 1607). SEQ ID NO: 26 depicts a representative RSV G protein, which is encoded by the gene sequence shown in SEQ ID NO: 25. Encompassed in this invention are RSV G proteins that are at least about 20%, about 30%, about 40%, about 50%, about 60%, about 70% or about 80%, about 85%, about 90%, about 95%, about 96%, about 97%, about 98% or about 99% identical to SEQ ID NO: 26, and all fragments and variants (including chimeric proteins) thereof.

The SH protein of RSV is a type II transmembrane protein that contains 64 (RSV subgroup A) or 65 amino acid residues (RSV subgroup B). Some studies have suggested that the RSV SH protein may have a role in viral fusion or in changing membrane permeability. However, RSV lacking the SH gene are viable, cause syncytia formation and grow as well as the wild-type virus, indicating that the SH protein is not necessary for virus entry into host cells or syncytia formation. The SH protein of RSV has shown the ability of inhibit TNF-α signaling. SEQ ID NO: 27 depicts a representative amino acid sequence of the RSV SH protein. Encompassed in this invention are RSV SH proteins that are at least about 20%, about 30%, about 40%, about 50%, about 60%, about 70% or about 80%, about 85%, about 90%, about 95%, about 96%, about 97%, about 98% or about 99% identical to SEQ ID NO: 27, and all fragments and variants (including chimeric proteins) thereof.

RSV Vaccines

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al., (1976) J. Infect. Dis. 134, 211-217; and Glezen et al. (1981) J. Pediatr. 98, 708-715). Hemming et al. (Morell et al., eds., 1986, Clinical Use of Intravenous Immunoglobulins, Academic Press, London at pages 285-294) recognized the possible utility of RSV antibody in treatment or prevention of RSV infection during studies involving the pharmacokinetics of an intravenous immunoglobulin (WIG) in newborns suspected of having neonatal sepsis. They noted that one infant, whose respiratory secretions yielded RSV, recovered rapidly after WIG infusion. Subsequent analysis of the IVIG lot revealed an unusually high titer of RSV neutralizing antibody. This same group of investigators then examined the ability of hyperimmune serum or immunoglobulin, enriched for RSV neutralizing antibody, to protect cotton rats and primates against RSV infection (Prince et al. (1985) Virus Res. 3, 193-206; Prince et al. (1990) J. Virol. 64, 3091-3092. Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Since RSV infection can be prevented by providing neutralizing antibodies to a vertebrate, a vaccine comprising a modified or mutated RSV F protein may induce, when administered to a vertebrate, neutralizing antibodies in vivo. The modified or mutated RSV F proteins are favorably used for the prevention and/or treatment of RSV infection. Thus, another aspect of this disclosure concerns a method for eliciting an immune response against RSV. The method involves administering an immunologically effective amount of a composition containing a modified or mutated RSV F protein to a subject (such as a human or animal subject). Administration of an immunologically effective amount of the composition elicits an immune response specific for epitopes present on the modified or mutated RSV F protein. Such an immune response can include B cell responses (e.g., the production of neutralizing antibodies) and/or T cell responses (e.g., the production of cytokines).

Preferably, the immune response elicited by the modified or mutated RSV F protein includes elements that are specific for at least one conformational epitope present on the modified or mutated RSV F protein. In one embodiment, the immune response is specific for an epitope present on an RSV F protein found in the "lollipop" post-fusion active state. The RSV F proteins and compositions can be administered to a subject without enhancing viral disease following contact with RSV. Preferably, the modified or mutated RSV F proteins disclosed herein and suitably formulated immunogenic compositions elicit a Th1 biased immune response that reduces or prevents infection with a RSV and/or reduces or prevents a pathological response following infection with a RSV.

In one embodiment, the RSV F proteins of the present invention are found in the form of micelles (e.g. rosettes). The micelles obtainable in accordance with the invention consist of aggregates of the immunogenically active F spike proteins having a rosette-like structure. The rosettes are visible in the electron microscope (Calder et al., 2000, Virology 271: 122-131). Preferably, the micelles of the present invention comprising modified or mutated RSV F proteins exhibit the "lollipop" morphology indicative of the post-fusion active state. In one embodiment, the micelles are purified following expression in a host cell. When administered to a subject, the micelles of the present invention preferably induce neutralizing antibodies. In some embodiments, the micelles may be administered with an adjuvant. In other embodiments, the micelles may be administered without an adjuvant.

In another embodiment, the invention encompasses RSV virus-like particles (VLPs) comprising a modified or mutated RSV F protein that can be formulated into vaccines or antigenic formulations for protecting vertebrates (e.g. humans) against RSV infection or at least one disease symptom thereof. The present invention also relates to RSV VLPs and vectors comprising wild-type and mutated RSV genes or a combination thereof derived from different strains of RSV virus, which when transfected into host cells, will produce virus like particles (VLPs) comprising RSV proteins.

In some embodiments, RSV virus-like particles may further comprise at least one viral matrix protein (e.g. an RSV M protein). In one embodiment, the M protein is derived from a human strain of RSV. In another embodiment, the M protein is derived from a bovine strain of RSV. In other embodiments, the matrix protein may be an M1 protein from a strain of influenza virus. In one embodiment, the strain of influenza virus is an avian influenza strain. In a preferred embodiment, the avian influenza strain is the H5N1 strain A/Indonesia/5/05. In other embodiments, the matrix protein may be from Newcastle Disease Virus (NDV).

In some embodiments, the VLPs may further comprise an RSV G protein. In one embodiment, the G protein may be from HRSV group A. In another embodiment, the G protein may be from HRSV group B. In yet another embodiment, the RSV G may be derived from HRSV group A and/or group B.

In some embodiments, the VLPs may further comprise an RSV SH protein. In one embodiment, the SH protein may be from HRSV group A. In another embodiment, the SH protein may be from HRSV group B. In yet another embodiment, the RSV SH may be derived from HRSV group A and/or group B.

In some embodiments, VLPs may further comprise an RSV N protein. In one embodiment, the N protein may be from HRSV group A. In another embodiment, the N protein may be from HRSV group B. In yet another embodiment, the RSV N may be derived from HRSV group A and/or group B.

In further embodiments, VLPs of the invention may comprise one or more heterologous immunogens, such as influenza hemagglutinin (HA) and/or neuraminidase (NA).

In some embodiments, the invention also comprises combinations of different RSV M, F, N, SH, and/or G proteins from the same and/or different strains in one or more VLPs. In addition, the VLPs can include one or more additional molecules for the enhancement of an immune response.

In another embodiment of the invention, the RSV VLPs can carry agents such as nucleic acids, siRNA, microRNA, chemotherapeutic agents, imaging agents, and/or other agents that need to be delivered to a patient.

VLPs of the invention are useful for preparing vaccines and immunogenic compositions. One important feature of VLPs is the ability to express surface proteins of interest so that the immune system of a vertebrate induces an immune response against the protein of interest. However, not all proteins can be expressed on the surface of VLPs. There may be many reasons why certain proteins are not expressed, or be poorly expressed, on the surface of VLPs. One reason is that the protein is not directed to the membrane of a host cell or that the protein does not have a transmembrane domain. As an example, sequences near the carboxyl terminus of influenza hemagglutinin may be important for incorporation of HA into the lipid bilayer of the mature influenza enveloped nucleocapsids and for the assembly of HA trimer interaction with the influenza matrix protein M1 (Ali, et al., (2000) J. Virol. 74, 8709-19).

Thus, one embodiment of the invention comprises chimeric VLPs comprising a modified or mutated F protein from RSV and at least one immunogen which is not normally efficiently expressed on the cell surface or is not a normal RSV protein. In one embodiment, the modified or mutated RSV F protein may be fused with an immunogen of interest. In another embodiment, the modified or mutated RSV F protein associates with the immunogen via the transmembrane domain and cytoplasmic tail of a heterologous viral surface membrane protein, e.g., MMTV envelope protein.

Other chimeric VLPs of the invention comprise VLPs comprising a modified or mutated RSV F protein and at least one protein from a heterologous infectious agent. Examples of heterologous infectious agent include but are not limited to a virus, a bacterium, a protozoan, a fungi and/or a parasite. In one embodiment, the immunogen from another infectious agent is a heterologous viral protein. In another embodiment, the protein from a heterologous infectious agent is an envelope-associated protein. In another embodiment, the protein from another heterologous infectious agent is expressed on the surface of VLPs. In another embodiment, the protein from an infectious agent comprises an epitope that will generate a protective immune response in a vertebrate. In one embodiment, the protein from another infectious agent is co-expressed with a modified or mutated RSV F protein. In another embodiment, the protein from another infectious agent is fused to a modified or mutated RSV F protein. In another embodiment, only a portion of a protein from another infectious agent is fused to a modified or mutated RSV F protein. In another embodiment, only a portion of a protein from another infectious agent is fused to a portion of a modified or mutated RSV F protein. In another embodiment, the portion of the protein from another infectious agent fused to modified or mutated RSV F protein is expressed on the surface of VLPs.

The invention also encompasses variants of the proteins expressed on or in the VLPs of the invention. The variants may contain alterations in the amino acid sequences of the constituent proteins. The term "variant" with respect to a protein refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Natural variants can occur due to mutations in the proteins. These mutations may lead to antigenic variability within individual groups of infectious agents, for example influenza. Thus, a person infected with, for example, an influenza strain develops antibody against that virus, as newer virus strains appear, the antibodies against the older strains no longer recognize the newer virus and re-infection can occur. The invention encompasses all antigenic and genetic variability of proteins from infectious agents for making VLPs.

General texts which describe molecular biological techniques, which are applicable to the present invention, such as cloning, mutation, cell culture and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and mutating F and/or G molecules of RSV, etc. Thus, the invention also encompasses using known methods of protein engineering and recombinant DNA technology to improve or alter the characteristics of the proteins expressed on or in the VLPs of the invention. Various types of mutagenesis can be used to produce and/or isolate variant nucleic acids that encode for protein molecules and/or to further modify/mutate the proteins in or on the VLPs of the invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

The invention further comprises protein variants which show substantial biological activity, e.g., able to elicit an effective antibody response when expressed on or in VLPs of the invention. Such variants include deletions, insertions, inversions, repeats, and substitutions selected according to general rules known in the art so as have little effect on activity.

Methods of cloning the proteins are known in the art. For example, the gene encoding a specific RSV protein can be isolated by RT-PCR from polyadenylated mRNA extracted from cells which had been infected with a RSV virus. The resulting product gene can be cloned as a DNA insert into a vector. The term "vector" refers to the means by which a nucleic acid can be propagated and/or transferred between organisms, cells, or cellular components. Vectors include plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. In many, but not all, common embodiments, the vectors of the present invention are plasmids or bacmids.

Thus, the invention comprises nucleotides that encode proteins, including chimeric molecules, cloned into an expression vector that can be expressed in a cell that induces the formation of VLPs of the invention. An "expression vector" is a vector, such as a plasmid that is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer. In one embodiment, the nucleotides encode for a modified or mutated RSV F protein (as discussed above). In another embodiment, the vector further comprises nucleotides that encode the M and/or G RSV proteins. In another embodiment, the vector further comprises nucleotides that encode the M and/or N RSV proteins. In another embodiment, the vector further comprises nucleotides that encode the M, G and/or N RSV proteins. In another embodiment, the vector further comprises nucleotides that encode a BRSV M protein and/or N RSV proteins. In another embodiment, the vector further comprises nucleotides that encode a BRSV M and/or G protein, or influenza HA and/or NA protein. In another embodiment, the nucleotides encode a modified or mutated RSV F and/or RSV G protein with an influenza HA and/or NA protein. In another embodiment, the expression vector is a baculovirus vector.

In some embodiments of the invention, proteins may comprise mutations containing alterations which produce silent substitutions, additions, or deletions, but do not alter the properties or activities of the encoded protein or how the proteins are made. Nucleotide variants can be produced for a variety of reasons, e.g., to optimize codon expression for a particular host (change codons in the human mRNA to those preferred by insect cells such as Sf9 cells. See U.S. Patent Publication 2005/0118191, herein incorporated by reference in its entirety for all purposes.

In addition, the nucleotides can be sequenced to ensure that the correct coding regions were cloned and do not contain any unwanted mutations. The nucleotides can be subcloned into an expression vector (e.g. baculovirus) for expression in any cell. The above is only one example of how the RSV viral proteins can be cloned. A person with skill in the art understands that additional methods are available and are possible.

The invention also provides for constructs and/or vectors that comprise RSV nucleotides that encode for RSV structural genes, including F, M, G, N, SH, or portions thereof, and/or any chimeric molecule described above. The vector may be, for example, a phage, plasmid, viral, or retroviral vector. The constructs and/or vectors that comprise RSV structural genes, including F, M, G, N, SH, or portions thereof, and/or any chimeric molecule described above, should be operatively linked to an appropriate promoter, such as the AcMNPV polyhedrin promoter (or other baculovirus), phage lambda PL promoter, the E. coli lac, phoA and tac promoters, the SV40 early and late promoters, and promoters of retroviral LTRs are non-limiting examples. Other suitable promoters will be known to the skilled artisan depending on the host cell and/or the rate of expression desired. The expression constructs will further contain sites for transcription initiation, termination, and, in the transcribed region, a ribosome-binding site for translation. The coding portion of the transcripts expressed by the constructs will preferably include a translation initiating codon at the beginning and a termination codon appropriately positioned at the end of the polypeptide to be translated.

Expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Among vectors preferred are virus vectors, such as baculovirus, poxvirus (e.g., vaccinia virus, avipox virus, canarypox virus, fowlpox virus, raccoonpox virus, swinepox virus, etc.), adenovirus (e.g., canine adenovirus), herpesvirus, and retrovirus. Other vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan. In one embodiment, the vector that comprises nucleotides encoding for RSV genes, including modified or mutated RSV F genes, as well as genes for M, G, N, SH or portions thereof, and/or any chimeric molecule described above, is pFastBac.

The recombinant constructs mentioned above could be used to transfect, infect, or transform and can express RSV proteins, including a modified or mutated RSV F protein and at least one immunogen. In one embodiment, the recombinant construct comprises a modified or mutated RSV F, M, G, N, SH, or portions thereof, and/or any molecule described above, into eukaryotic cells and/or prokaryotic cells. Thus, the invention provides for host cells which comprise a vector (or vectors) that contain nucleic acids which code for RSV structural genes, including a modified or mutated RSV F; and at least one immunogen such as but not limited to RSV G, N, and SH, or portions thereof, and/or any molecule described above, and permit the expression of genes, including RSV F, G, N, M, or SH or portions thereof, and/or any molecule described above in the host cell under conditions which allow the formation of VLPs.

Among eukaryotic host cells are yeast, insect, avian, plant, C. elegans (or nematode) and mammalian host cells. Non limiting examples of insect cells are, Spodoptera frugiperda (Sf) cells, e.g. Sf9, Sf21, Trichoplusia ni cells, e.g. High Five cells, and Drosophila S2 cells. Examples of fungi (including yeast) host cells are S. cerevisiae, Kluyveromyces lactis (K. lactis), species of Candida including C. albicans and C. glabrata, Aspergillus nidulans, Schizosaccharomyces pombe (S. pombe), Pichia pastoris, and Yarrowia lipolytica. Examples of mammalian cells are COS cells, baby hamster kidney cells, mouse L cells, LNCaP cells, Chinese hamster ovary (CHO) cells, human embryonic kidney (HEK) cells, and African green monkey cells, CV1 cells, HeLa cells, MDCK cells, Vero and Hep-2 cells. Xenopus laevis oocytes, or other cells of amphibian origin, may also be used. Examples of prokaryotic host cells include bacterial cells, for example, E. coli, B. subtilis, Salmonella typhi and mycobacteria.

Vectors, e.g., vectors comprising polynucleotides of a modified or mutated RSV F protein; and at least one immunogen including but not limited to RSV G, N, or SH or portions thereof, and/or any chimeric molecule described above, can be transfected into host cells according to methods well known in the art. For example, introducing nucleic acids into eukaryotic cells can be by calcium phosphate co-precipitation, electroporation, microinjection, lipofection, and transfection employing polyamine transfection reagents. In one embodiment, the vector is a recombinant baculovirus. In another embodiment, the recombinant baculovirus is transfected into a eukaryotic cell. In a preferred embodiment, the cell is an insect cell. In another embodiment, the insect cell is a Sf9 cell.

This invention also provides for constructs and methods that will increase the efficiency of VLP production. For example, the addition of leader sequences to the RSV F, M, G, N, SH, or portions thereof, and/or any chimeric or heterologous molecules described above, can improve the efficiency of protein transporting within the cell. For example, a heterologous signal sequence can be fused to the F, M, G, N, SH, or portions thereof, and/or any chimeric or heterologous molecule described above. In one embodiment, the signal sequence can be derived from the gene of an insect cell and fused to M, F, G, N, SH, or portions thereof, and/or any chimeric or heterologous molecules described above. In another embodiment, the signal peptide is the chitinase signal sequence, which works efficiently in baculovirus expression systems.

Another method to increase efficiency of VLP production is to codon optimize the nucleotides that encode RSV including a modified or mutated RSV F protein, M, G, N, SH or portions thereof, and/or any chimeric or heterologous molecules described above for a specific cell type. For examples of codon optimizing nucleic acids for expression in Sf9 cell see SEQ ID Nos: 3, 5, 7, 9, 13, 17, 19, and 25.

The invention also provides for methods of producing VLPs, the methods comprising expressing RSV genes including a modified or mutated RSV F protein, and at least one additional protein, including but not limited to RSV M, G, N, SH, or portions thereof, and/or any chimeric or heterologous molecules described above under conditions that allow VLP formation. Depending on the expression system and host cell selected, the VLPs are produced by growing host cells transformed by an expression vector under conditions whereby the recombinant proteins are expressed and VLPs are formed. In one embodiment, the invention comprises a method of producing a VLP, comprising transfecting vectors encoding at least one modified or mutated RSV F protein into a suitable host cell and expressing the modified or mutated RSV F protein under conditions that allow VLP formation. In another embodiment, the eukaryotic cell is selected from the group consisting of, yeast, insect, amphibian, avian or mammalian cells. The selection of the appropriate growth conditions is within the skill or a person with skill of one of ordinary skill in the art.

Methods to grow cells engineered to produce VLPs of the invention include, but are not limited to, batch, batch-fed, continuous and perfusion cell culture techniques. Cell culture means the growth and propagation of cells in a bioreactor (a fermentation chamber) where cells propagate and express protein (e.g. recombinant proteins) for purification and isolation. Typically, cell culture is performed under sterile, controlled temperature and atmospheric conditions in a bioreactor. A bioreactor is a chamber used to culture cells in which environmental conditions such as temperature, atmosphere, agitation and/or pH can be monitored. In one embodiment, the bioreactor is a stainless steel chamber. In another embodiment, the bioreactor is a pre-sterilized plastic bag (e.g. Cellbag®, Wave Biotech, Bridgewater, N.J.). In other embodiment, the pre-sterilized plastic bags are about 50 L to 1000 L bags.

The VLPs are then isolated using methods that preserve the integrity thereof, such as by gradient centrifugation, e.g., cesium chloride, sucrose and iodixanol, as well as standard purification techniques including, e.g., ion exchange and gel filtration chromatography.

The following is an example of how VLPs of the invention can be made, isolated and purified. Usually VLPs are produced from recombinant cell lines engineered to create VLPs when the cells are grown in cell culture (see above). A person of skill in the art would understand that there are additional methods that can be utilized to make and purify VLPs of the invention, thus the invention is not limited to the method described.

Production of VLPs of the invention can start by seeding Sf9 cells (non-infected) into shaker flasks, allowing the cells to expand and scaling up as the cells grow and multiply (for example from a 125-ml flask to a 50 L Wave bag). The medium used to grow the cell is formulated for the appropriate cell line (preferably serum free media, e.g. insect medium ExCell-420, JRH). Next, the cells are infected with recombinant baculovirus at the most efficient multiplicity of infection (e.g. from about 1 to about 3 plaque forming units per cell). Once infection has occurred, the modified or mutated RSV F protein, M, G, N, SH, or portions thereof, and/or any chimeric or heterologous molecule described above, are expressed from the virus genome, self assemble into VLPs and are secreted from the cells approximately 24 to 72 hours post infection. Usually, infection is most efficient when the cells are in mid-log phase of growth ($4$-$8 \times 10^6$ cells/ml) and are at least about 90% viable.

VLPs of the invention can be harvested approximately 48 to 96 hours post infection, when the levels of VLPs in the cell culture medium are near the maximum but before extensive cell lysis. The Sf9 cell density and viability at the time of harvest can be about $0.5 \times 10^6$ cells/ml to about $1.5 \times 10^6$ cells/ml with at least 20% viability, as shown by dye exclusion assay. Next, the medium is removed and clarified. NaCl can be added to the medium to a concentration of about 0.4 to about 1.0 M, preferably to about 0.5 M, to avoid VLP aggregation. The removal of cell and cellular debris from the cell culture medium containing VLPs of the invention can be accomplished by tangential flow filtration (TFF) with a single use, pre-sterilized hollow fiber 0.5 or 1.00 µm filter cartridge or a similar device.

Next, VLPs in the clarified culture medium can be concentrated by ultra-filtration using a disposable, pre-sterilized 500,000 molecular weight cut off hollow fiber cartridge. The concentrated VLPs can be diafiltrated against 10 volumes pH 7.0 to 8.0 phosphate-buffered saline (PBS) containing 0.5 M NaCl to remove residual medium components.

The concentrated, diafiltrated VLPs can be furthered purified on a 20% to 60% discontinuous sucrose gradient in pH 7.2 PBS buffer with 0.5 M NaCl by centrifugation at $6,500 \times g$ for 18 hours at about 4° C. to about 10° C. Usually VLPs will form a distinctive visible band between about 30% to about 40% sucrose or at the interface (in a 20% and 60% step gradient) that can be collected from the gradient and stored. This product can be diluted to comprise 200 mM of NaCl in preparation for the next step in the purification process. This product contains VLPs and may contain intact baculovirus particles.

Further purification of VLPs can be achieved by anion exchange chromatography, or 44% isopycnic sucrose cushion centrifugation. In anion exchange chromatography, the sample from the sucrose gradient (see above) is loaded into column containing a medium with an anion (e.g. Matrix Fractogel EMD TMAE) and eluded via a salt gradient (from about 0.2 M to about 1.0 M of NaCl) that can separate the VLP from other contaminates (e.g. baculovirus and DNA/RNA). In the sucrose cushion method, the sample comprising the VLPs is added to a 44% sucrose cushion and centrifuged for about 18 hours at 30,000 g. VLPs form a band at the top of 44% sucrose, while baculovirus precipitates at the bottom and other contaminating proteins stay in the 0% sucrose layer at the top. The VLP peak or band is collected.

The intact baculovirus can be inactivated, if desired. Inactivation can be accomplished by chemical methods, for example, formalin or β-propiolactone (BPL). Removal and/or inactivation of intact baculovirus can also be largely accomplished by using selective precipitation and chromatographic methods known in the art, as exemplified above. Methods of inactivation comprise incubating the sample containing the VLPs in 0.2% of BPL for 3 hours at about 25° C. to about 27° C. The baculovirus can also be inactivated by incubating the sample containing the VLPs at 0.05% BPL at 4° C. for 3 days, then at 37° C. for one hour.

After the inactivation/removal step, the product comprising VLPs can be run through another diafiltration step to remove any reagent from the inactivation step and/or any residual sucrose, and to place the VLPs into the desired buffer (e.g. PBS). The solution comprising VLPs can be sterilized by methods known in the art (e.g. sterile filtration) and stored in the refrigerator or freezer.

The above techniques can be practiced across a variety of scales. For example, T-flasks, shake-flasks, spinner bottles, up to industrial sized bioreactors. The bioreactors can comprise either a stainless steel tank or a pre-sterilized plastic bag (for example, the system sold by Wave Biotech, Bridgewater, N.J.). A person with skill in the art will know what is most desirable for their purposes.

Expansion and production of baculovirus expression vectors and infection of cells with recombinant baculovirus to produce recombinant RSV VLPs can be accomplished in insect cells, for example Sf9 insect cells as previously described. In one embodiment, the cells are SF9 infected with recombinant baculovirus engineered to produce RSV VLPs.

Pharmaceutical or Vaccine Formulations and Administration

The pharmaceutical compositions useful herein contain a pharmaceutically acceptable carrier, including any suitable diluent or excipient, which includes any pharmaceutical agent that does not itself induce the production of an immune response harmful to the vertebrate receiving the composition, and which may be administered without undue toxicity and a modified or mutated RSV F protein, an RSV F micelle comprising a modified or mutated RSV F protein, or a VLP comprising a modified or mutated RSV F protein of the invention. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. These compositions can be useful as a vaccine and/or antigenic compositions for inducing a protective immune response in a vertebrate.

The invention encompasses a pharmaceutically acceptable vaccine composition comprising VLPs comprising at least one modified or mutated RSV F protein, and at least one additional protein, including but not limited to RSV M, G, N, SH, or portions thereof, and/or any chimeric or heterologous molecules described above. In one embodiment, the pharmaceutically acceptable vaccine composition comprises VLPs comprising at least one modified or mutated RSV F protein and at least one additional immunogen. In another embodiment, the pharmaceutically acceptable vaccine composition comprises VLPs comprising at least one modified or mutated RSV F protein and at least one RSV M protein. In another embodiment, the pharmaceutically acceptable vaccine composition comprises VLPs comprising at least one modified or mutated RSV F protein and at least one BRSV M protein. In another embodiment, the pharmaceutically acceptable vaccine composition comprises VLPs comprising at least one modified or mutated RSV F protein and at least one influenza M1 protein. In another embodiment, the pharmaceutically acceptable vaccine composition comprises VLPs comprising at least one modified or mutated RSV F protein and at least one avian influenza M1 protein.

In another embodiment, the pharmaceutically acceptable vaccine composition comprises VLPs further comprising an RSV G protein, including but not limited to a HRSV, BRSV or avian RSV G protein. In another embodiment, the pharmaceutically acceptable vaccine composition comprises VLPs further comprising RSV N protein, including but not limited to a HRSV, BRSV or avian RSV N protein. In another embodiment, the pharmaceutically acceptable vaccine composition comprises VLPs further comprising RSV SH protein, including but not limited to a HRSV, BRSV or avian RSV SH protein.

In another embodiment, the invention encompasses a pharmaceutically acceptable vaccine composition comprising chimeric VLPs such as VLPs comprising BRSV M and a modified or mutated RSV F protein and/or G, H, or SH protein from a RSV and optionally HA or NA protein derived from an influenza virus, wherein the HA or NA protein is a fused to the transmembrane domain and cytoplasmic tail of RSV F and/or G protein.

The invention also encompasses a pharmaceutically acceptable vaccine composition comprising modified or mutated RSV F protein, an RSV F micelle comprising a modified or mutated RSV F protein, or a VLP comprising a modified or mutated RSV F protein as described above.

In one embodiment, the pharmaceutically acceptable vaccine composition comprises VLPs comprising a modified or mutated RSV F protein and at least one additional protein. In another embodiment, the pharmaceutically acceptable vaccine composition comprises VLPs further comprising RSV M protein, such as but not limited to a BRSV M protein. In another embodiment, the pharmaceutically acceptable vaccine composition comprises VLPs further comprising RSV G protein, including but not limited to a HRSV G protein. In another embodiment, the pharmaceutically acceptable vaccine composition comprises VLPs further comprising RSV N protein, including but not limited to a HRSV, BRSV or avian RSV N protein. In another embodiment, the pharmaceutically acceptable vaccine composition comprises VLPs further comprising RSV SH protein, including but not limited to a HRSV, BRSV or avian RSV SH protein. In another embodiment, the pharmaceutically acceptable vaccine composition comprises VLPs comprising BRSV M protein and F and/or G protein from HRSV group A. In another embodiment, the pharmaceutically acceptable vaccine composition comprises VLPs comprising BRSV M protein and F and/or G protein from HRSV group B. In another embodiment, the invention encompasses a pharmaceutically acceptable vaccine composition comprising chimeric VLPs such as VLPs comprising chimeric M protein from a BRSV and optionally HA protein derived from an influenza virus, wherein the M protein is fused to the influenza HA protein. In another embodiment, the invention encompasses a pharmaceutically acceptable vaccine composition comprising chimeric VLPs such as VLPs comprising BRSV M, and a chimeric F and/or G protein from a RSV and optionally HA protein derived from an influenza virus, wherein the chimeric influenza HA protein is fused to the transmembrane domain and cytoplasmic tail of RSV F and/or G protein. In another embodiment, the invention encompasses a pharmaceutically acceptable vaccine composition comprising chimeric VLPs such as VLPs comprising BRSV M and a chimeric F and/or G protein from a RSV and optionally HA or NA protein derived from an influenza virus, wherein the HA or NA protein is a fused to the transmembrane domain and cytoplasmic tail of RSV F and/or G protein.

The invention also encompasses a pharmaceutically acceptable vaccine composition comprising a chimeric VLP that comprises at least one RSV protein. In one embodiment, the pharmaceutically acceptable vaccine composition comprises VLPs comprising a modified or mutated RSV F protein and at least one immunogen from a heterologous infectious agent or diseased cell. In another embodiment, the immunogen from a heterologous infectious agent is a viral protein. In another embodiment, the viral protein from a heterologous infectious agent is an envelope associated protein. In another embodiment, the viral protein from a heterologous infectious agent is expressed on the surface of VLPs. In another embodiment, the protein from an infectious agent comprises an epitope that will generate a protective immune response in a vertebrate.

The invention also encompasses a kit for immunizing a vertebrate, such as a human subject, comprising VLPs that comprise at least one RSV protein. In one embodiment, the kit comprises VLPs comprising a modified or mutated RSV F protein. In one embodiment, the kit further comprises a RSV M protein such as a BRSV M protein. In another embodiment, the kit further comprises a RSV G protein. In another embodiment, the invention encompasses a kit comprising VLPs which comprises a chimeric M protein from a BRSV and optionally HA protein derived from an influenza virus, wherein the M protein is fused to the BRSV M. In another embodiment, the invention encompasses a kit comprising VLPs which comprises a chimeric M protein from a BRSV, a RSV F and/or G protein and an immunogen from a heterologous infectious agent. In another embodiment, the invention encompasses a kit comprising VLPs which comprises a M protein from a BRSV, a chimeric RSV F and/or G protein and optionally HA protein derived from an influenza virus, wherein the HA protein is fused to the transmembrane domain and cytoplasmic tail of RSV F or G protein. In another embodiment, the invention encompasses a kit comprising VLPs which comprises M protein from a BRSV, a chimeric RSV F and/or G protein and optionally HA or NA protein derived from an influenza virus, wherein the HA protein is fused to the transmembrane domain and cytoplasmic tail of RSV F and/or G protein.

In one embodiment, the invention comprises an immunogenic formulation comprising at least one effective dose of a modified or mutated RSV F protein. In another embodiment, the invention comprises an immunogenic formulation comprising at least one effective dose of an RSV F micelle comprising a modified or mutated RSV F protein. In yet another embodiment, the invention comprises an immunogenic formulation comprising at least one effective dose of a VLP comprising a modified or mutated RSV F protein as described above.

The immunogenic formulation of the invention comprises a modified or mutated RSV F protein, an RSV F micelle comprising a modified or mutated RSV F protein, or a VLP comprising a modified or mutated RSV F protein, and a pharmaceutically acceptable carrier or excipient. Pharmaceutically acceptable carriers include but are not limited to saline, buffered saline, dextrose, water, glycerol, sterile isotonic aqueous buffer, and combinations thereof A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably is sterile, non-particulate and/or non-pyrogenic.

The composition, if desired, can also contain minor amounts of wetting or emulsifying agents, or pH buffering agents. The composition can be a solid form, such as a lyophilized powder suitable for reconstitution, a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

The invention also provides for a pharmaceutical pack or kit comprising one or more containers filled with one or more of the ingredients of the vaccine formulations of the invention. In a preferred embodiment, the kit comprises two containers, one containing a modified or mutated RSV F protein, an RSV F micelle comprising a modified or mutated RSV F protein, or a VLP comprising a modified or mutated RSV F protein, and the other containing an adjuvant. Associated with such container(s) can be a notice in the form prescribed by a governmental agency regulating the manufacture, use or sale of pharmaceuticals or biological products, which notice reflects approval by the agency of manufacture, use or sale for human administration.

The invention also provides that the formulation be packaged in a hermetically sealed container such as an ampoule or sachette indicating the quantity of composition. In one embodiment, the composition is supplied as a liquid, in another embodiment, as a dry sterilized lyophilized powder or water free concentrate in a hermetically sealed container and can be reconstituted, e.g., with water or saline to the appropriate concentration for administration to a subject.

In an alternative embodiment, the composition is supplied in liquid form in a hermetically sealed container indicating the quantity and concentration of the composition. Preferably, the liquid form of the composition is supplied in a hermetically sealed container at least about 50 µg/ml, more preferably at least about 100 tg/ml, at least about 200 µg/ml, at least 500 µg/ml, or at least 1 mg/ml.

As an example, chimeric RSV VLPs comprising a modified or mutated RSV F protein of the invention are administered in an effective amount or quantity (as defined above) sufficient to stimulate an immune response, each a response against one or more strains of RSV. Administration of the modified or mutated RSV F protein, an RSV F micelle comprising a modified or mutated RSV F protein, or VLP of the invention elicits immunity against RSV. Typically, the dose can be adjusted within this range based on, e.g., age, physical condition, body weight, sex, diet, time of administration, and other clinical factors. The prophylactic vaccine formulation is systemically administered, e.g., by subcutaneous or intramuscular injection using a needle and syringe, or a needle-less injection device. Alternatively, the vaccine formulation is administered intranasally, either by drops, large particle aerosol (greater than about 10 microns), or spray into the upper respiratory tract. While any of the above routes of delivery results in an immune response, intranasal administration confers the added benefit of eliciting mucosal immunity at the site of entry of many viruses, including RSV and influenza.

Thus, the invention also comprises a method of formulating a vaccine or antigenic composition that induces immunity to an infection or at least one disease symptom thereof to a mammal, comprising adding to the formulation an effective dose of a modified or mutated RSV F protein, an RSV F micelle comprising a modified or mutated RSV F protein, or a VLP comprising a modified or mutated RSV F protein. In one embodiment, the infection is an RSV infection.

While stimulation of immunity with a single dose is possible, additional dosages can be administered, by the same or different route, to achieve the desired effect. In neonates and infants, for example, multiple administrations may be required to elicit sufficient levels of immunity. Administration can continue at intervals throughout childhood, as necessary to maintain sufficient levels of protection against infections, e.g. RSV infection. Similarly, adults who are particularly susceptible to repeated or serious infections, such as, for example, health care workers, day care workers, family members of young children, the elderly, and individuals with compromised cardiopulmonary function may require multiple immunizations to establish and/or maintain protective immune responses. Levels of induced immunity can be monitored, for example, by measuring amounts of neutralizing secretory and serum antibodies, and dosages adjusted or vaccinations repeated as necessary to elicit and maintain desired levels of protection.

Methods of administering a composition comprising a modified or mutated RSV F protein, an RSV F micelle comprising a modified or mutated RSV F protein, or a VLP comprising a modified or mutated RSV F protein (e.g. vaccine and/or antigenic formulations) include, but are not limited to, parenteral administration (e.g., intradermal, intramuscular, intravenous and subcutaneous), epidural, and mucosal (e.g., intranasal and oral or pulmonary routes or by suppositories). In a specific embodiment, compositions of the present invention are administered intramuscularly, intravenously, subcutaneously, transdermally or intradermally. The compositions may be administered by any convenient route, for example by infusion or bolus injection, by absorption through epithelial or mucocutaneous linings (e.g., oral mucous, colon, conjunctiva, nasopharynx, oropharynx, vagina, urethra, urinary bladder and intestinal mucosa, etc.) and may be administered together with other biologically active agents. In some embodiments, intranasal or other mucosal routes of administration of a composition of the invention may induce an antibody or other immune response that is substantially higher than other routes of administration. In another embodiment, intranasal or other mucosal routes of administration of a composition of the invention may induce an antibody or other immune response that will induce cross protection against other strains of RSV. Administration can be systemic or local.

In yet another embodiment, the vaccine and/or immunogenic formulation is administered in such a manner as to target mucosal tissues in order to elicit an immune response at the site of immunization. For example, mucosal tissues such as gut associated lymphoid tissue (GALT) can be targeted for immunization by using oral administration of compositions which contain adjuvants with particular mucosal targeting properties. Additional mucosal tissues can also be targeted, such as nasopharyngeal lymphoid tissue (NALT) and bronchial-associated lymphoid tissue (BALT).

Vaccines and/or immunogenic formulations of the invention may also be administered on a dosage schedule, for example, an initial administration of the vaccine composition with subsequent booster administrations. In particular embodiments, a second dose of the composition is administered anywhere from two weeks to one year, preferably from about 1, about 2, about 3, about 4, about 5 to about 6 months, after the initial administration. Additionally, a third dose may be administered after the second dose and from about three months to about two years, or even longer, preferably about 4, about 5, or about 6 months, or about 7 months to about one year after the initial administration. The third dose may be optionally administered when no or low levels of specific immunoglobulins are detected in the serum and/or urine or mucosal secretions of the subject after the second dose. In a preferred embodiment, a second dose is administered about one month after the first administration and a third dose is administered about six months after the first administration. In another embodiment, the second dose is administered about six months after the first administration. In another embodiment, the compositions of the invention can be administered as part of a combination therapy. For example, compositions of the invention can be formulated with other immunogenic compositions, antivirals and/or antibiotics.

The dosage of the pharmaceutical composition can be determined readily by the skilled artisan, for example, by first identifying doses effective to elicit a prophylactic or therapeutic immune response, e.g., by measuring the serum titer of virus specific immunoglobulins or by measuring the inhibitory ratio of antibodies in serum samples, or urine samples, or mucosal secretions. The dosages can be determined from animal studies. A non-limiting list of animals used to study the efficacy of vaccines include the guinea pig, hamster, ferrets, chinchilla, mouse and cotton rat. Most animals are not natural hosts to infectious agents but can still serve in studies of various aspects of the disease. For example, any of the above animals can be dosed with a vaccine candidate, e.g. modified or mutated RSV F proteins, an RSV F micelle comprising a modified or mutated RSV F protein, or VLPs of the invention, to partially characterize the immune response induced, and/or to determine if any neutralizing antibodies have been produced. For example, many studies have been conducted in the mouse model because mice are small size and their low cost allows researchers to conduct studies on a larger scale.

In addition, human clinical studies can be performed to determine the preferred effective dose for humans by a skilled artisan. Such clinical studies are routine and well known in the art. The precise dose to be employed will also depend on the route of administration. Effective doses may be extrapolated from dose-response curves derived from in vitro or animal test systems.

As also well known in the art, the immunogenicity of a particular composition can be enhanced by the use of non-specific stimulators of the immune response, known as adjuvants. Adjuvants have been used experimentally to promote a generalized increase in immunity against unknown antigens (e.g., U.S. Pat. No. 4,877,611) Immunization protocols have used adjuvants to stimulate responses for many years, and as such, adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation. The inclusion of any adjuvant described in Vogel et al., "A Compendium of Vaccine Adjuvants and Excipients ($2^{nd}$ Edition)," herein incorporated by reference in its entirety for all purposes, is envisioned within the scope of this invention.

Exemplary, adjuvants include complete Freund's adjuvant (a non-specific stimulator of the immune response containing killed *Mycobacterium tuberculosis*), incomplete Freund's adjuvants and aluminum hydroxide adjuvant. Other adjuvants comprise GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is contemplated. MF-59, Novasomes®, MHC antigens may also be used.

In one embodiment of the invention the adjuvant is a paucilamellar lipid vesicle having about two to ten bilayers arranged in the form of substantially spherical shells separated by aqueous layers surrounding a large amorphous central cavity free of lipid bilayers. Paucilamellar lipid vesicles may act to stimulate the immune response several ways, as non-specific stimulators, as carriers for the antigen, as carriers of additional adjuvants, and combinations thereof. Paucilamellar lipid vesicles act as non-specific immune stimulators when, for example, a vaccine is prepared by intermixing the antigen with the preformed vesicles such that the antigen remains extracellular to the vesicles. By encapsulating an antigen within the central cavity of the vesicle, the vesicle acts both as an immune stimulator and a carrier for the antigen. In another embodiment, the vesicles are primarily made of nonphospholipid vesicles. In other embodiment, the vesicles are Novasomes®. Novasomes® are paucilamellar nonphospholipid vesicles ranging from about 100 nm to about 500 nm. They comprise Brij 72, cholesterol, oleic acid and squalene. Novasomes have been shown to be an effective adjuvant for influenza antigens (see, U.S. Pat. Nos. 5,629,021, 6,387,373, and 4,911,928, herein incorporated by reference in their entireties for all purposes).

The compositions of the invention can also be formulated with "immune stimulators." These are the body's own chemical messengers (cytokines) to increase the immune system's response Immune stimulators include, but not limited to, various cytokines, lymphokines and chemokines with immunostimulatory, immunopotentiating, and pro-inflammatory activities, such as interleukins (e.g., IL-1, IL-2, IL-3, IL-4, IL-12, IL-13); growth factors (e.g., granulocyte-macrophage (GM)-colony stimulating factor (CSF)); and other immunostimulatory molecules, such as macrophage inflammatory factor, F1t3 ligand, B7.1; B7.2, etc. The immunostimulatory molecules can be administered in the same formulation as the compositions of the invention, or can be administered separately. Either the protein or an expression vector encoding the protein can be administered to produce an immunostimulatory effect. Thus in one embodiment, the invention comprises antigenic and vaccine formulations comprising an adjuvant and/or an immune stimulator.

Methods of Stimulating an Immune Response

The modified or mutated RSV F proteins, the RSV F micelles comprising a modified or mutated RSV F protein, or the VLPs of the invention are useful for preparing compositions that stimulate an immune response that confers immunity or substantial immunity to infectious agents. Both mucosal and cellular immunity may contribute to immunity to infectious agents and disease. Antibodies secreted locally in the upper respiratory tract are a major factor in resistance to natural infection. Secretory immunoglobulin A (sIgA) is involved in the protection of the upper respiratory tract and serum IgG in protection of the lower respiratory tract. The immune response induced by an infection protects against reinfection with the same virus or an antigenically similar viral strain. For example, RSV undergoes frequent and unpredictable changes; therefore, after natural infection, the effective period of protection provided by the host's immunity may only be effective for a few years against the new strains of virus circulating in the community.

Thus, the invention encompasses a method of inducing immunity to infections or at least one disease symptom thereof in a subject, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs comprising a modified or mutated RSV F protein and at least one additional protein. In another embodiment, the method comprises administering VLPs further comprising an RSV M protein, for example, a BRSV M protein. In another embodiment, the method comprises administering VLPs further comprising a RSV N protein. In another embodiment, the method comprises administering VLPs further comprising a RSV G protein. In another embodiment, the method comprises administering VLPs further comprising a RSV SH protein. In another embodiment, the method comprises administering VLPs further comprising F and/or G protein from HRSV group A and/or group B. In another embodiment, the method comprises administering VLPs comprising M protein from BRSV and a chimeric RSV F and/or G protein or MMTV envelope protein, for example, HA or NA protein derived from an influenza virus, wherein the HA and/or NA protein is fused to the transmembrane domain and cytoplasmic tail of the RSV F and/or G protein or MMTV envelope protein. In another embodiment, the method comprises administering VLPs comprising M protein from BRSV and a chimeric RSV F and/or G protein and optionally HA or NA protein derived from an influenza virus, wherein the HA or NA protein is fused to the transmembrane domain and cytoplasmic tail of RSV F and/or G protein. In another embodiment, the subject is a mammal In another embodiment, the mammal is a human. In another embodiment, RSV VLPs are formulated with an adjuvant or immune stimulator.

In one embodiment, the invention comprises a method to induce immunity to RSV infection or at least one disease symptom thereof in a subject, comprising administering at least one effective dose of a modified or mutated RSV F protein. In another embodiment, the invention comprises a method to induce immunity to RSV infection or at least one disease symptom thereof in a subject, comprising administering at least one effective dose of an RSV F micelle comprising a modified or mutated RSV F protein. In yet another embodiment, the invention comprises a method to induce immunity to RSV infection or at least one disease symptom thereof in a subject, comprising administering at least one effective dose of a RSV VLPs, wherein the VLPs comprise a modified or mutated RSV F protein, M, G, SH, and/or N proteins. In another embodiment, a method of inducing immunity to RSV infection or at least one symptom thereof in a subject, comprises administering at least one effective dose of a RSV VLPs, wherein the VLPs consists essentially of BRSV M (including chimeric M), and RSV F, G, and/or N proteins. The VLPs may comprise additional RSV proteins and/or protein contaminates in negligible concentrations. In another embodiment, a method of inducing immunity to RSV infection or at least one symptom thereof in a subject, comprises administering at least one effective dose of a RSV VLPs, wherein the VLPs consists of BRSV M (including chimeric M), RSV G and/or F. In another embodiment, a method of inducing immunity to RSV infection or at least one disease symptom in a subject, comprises administering at least one effective dose of a RSV VLPs comprising RSV proteins, wherein the RSV proteins consist of BRSV M (including chimeric M), F, G, and/or N proteins, including chimeric F, G, and/or N proteins. These VLPs contain BRSV M (including chimeric M), RSV F, G, and/or N proteins and may contain additional cellular constituents such as cellular proteins, baculovirus proteins, lipids, carbohydrates etc., but do not contain additional RSV proteins (other than fragments of BRSV M (including chimeric M), BRSV/RSV F, G, and/or N proteins. In another embodiment, the subject is a vertebrate. In one embodiment the vertebrate is a mammal In another embodiment, the mammal is a human. In another embodiment, the method comprises inducing immunity to RSV infection or at least one disease symptom by administering the formulation in one dose. In another embodiment, the method comprises inducing immunity to RSV infection or at least one disease symptom by administering the formulation in multiple doses.

The invention also encompasses inducing immunity to an infection, or at least one symptom thereof, in a subject caused by an infectious agent, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs comprising a modified or mutated RSV F protein and at least one protein from a heterologous infectious agent. In one embodiment, the method comprises administering VLPs comprising a modified or mutated RSV F protein and at least one protein from the same or a heterologous infectious agent. In another embodiment, the protein from the heterologous infectious agent is a viral protein. In another embodiment, the protein from the infectious agent is an envelope associated protein. In another embodiment, the protein from the infectious agent is expressed on the surface of VLPs. In another embodiment, the protein from the infectious agent comprises an epitope that will generate a protective immune response in a vertebrate. In another embodiment, the protein from the infectious agent can associate with RSV M protein such as BRSV M protein, RSV F, G and/or N protein. In another embodiment, the protein from the infectious agent is fused to a RSV protein such as a BRSV M protein, RSV F, G and/or N protein. In another embodiment, only a portion of a protein from the infectious agent is fused to a RSV protein such as a BRSV M protein, RSV F, G and/or N protein. In another embodiment, only a portion of a protein from the infectious agent is fused to a portion of a RSV protein such as a BRSV M protein, RSV F, G and/or N protein. In another embodiment, the portion of the protein from the infectious agent fused to the RSV protein is expressed on the surface of VLPs. In other embodiment, the RSV protein, or portion thereof, fused to the protein from the infectious agent associates with the RSV M protein. In other embodiment, the RSV protein, or portion thereof, is derived from RSV F, G, N and/or P. In another embodiment, the chimeric VLPs further comprise N and/or P protein from RSV. In another embodiment, the chimeric VLPs comprise more than one protein from the same and/or a heterologous infectious agent. In another embodiment, the chimeric VLPs comprise more than one infectious agent protein, thus creating a multivalent VLP.

Compositions of the invention can induce substantial immunity in a vertebrate (e.g. a human) when administered to the vertebrate. The substantial immunity results from an immune response against compositions of the invention that protects or ameliorates infection or at least reduces a symptom of infection in the vertebrate. In some instances, if the vertebrate is infected, the infection will be asymptomatic. The response may not be a fully protective response. In this case, if the vertebrate is infected with an infectious agent, the vertebrate will experience reduced symptoms or a shorter duration of symptoms compared to a non-immunized vertebrate.

In one embodiment, the invention comprises a method of inducing substantial immunity to RSV virus infection or at least one disease symptom in a subject, comprising administering at least one effective dose of a modified or mutated RSV F protein, an RSV F micelle comprising a modified or mutated RSV F protein, or a VLP comprising a modified or mutated RSV F protein. In another embodiment, the invention comprises a method of vaccinating a mammal against RSV comprising administering to the mammal a protection-inducing amount of a modified or mutated RSV F protein, an RSV F micelle comprising a modified or mutated RSV F protein, or a VLP comprising a modified or mutated RSV F protein. In one embodiment, the method comprises administering VLPs further comprising an RSV M protein, such as BRSV M protein. In another embodiment, the method further comprises administering VLPs comprising RSV G protein, for example a HRSV G protein. In another embodiment, the method further comprises administering VLPs comprising the N protein from HRSV group A. In another embodiment, the method further comprises administering VLPs comprising the N protein from HRSV group B. In another embodiment, the method comprises administering VLPs comprising chimeric M protein from BRSV and F and/or G protein derived from RSV wherein the F and/or G protein is fused to the transmembrane and cytoplasmic tail of the M protein. In another embodiment, the method comprises administering VLPs comprising M protein from BRSV and chimeric RSV F and/or G protein wherein the F and/or G protein is a fused to the transmembrane domain and cytoplasmic tail of influenza HA and/or NA protein. In another embodiment, the method comprises administering VLPs comprising M protein from BRSV and chimeric RSV F and/or G protein and optionally an influenza HA and/or NA protein wherein the F and/or G protein is a fused to the transmembrane domain and cytoplasmic tail of the HA protein. In another embodiment, the method comprises administering VLPs comprising M protein from BRSV and chimeric RSV F and/or G protein, and optionally an influenza HA and/or NA protein wherein the HA and/or NA protein is fused to the transmembrane domain and cytoplasmic tail of RSV F and/or G protein.

The invention also encompasses a method of inducing substantial immunity to an infection, or at least one disease symptom in a subject caused by an infectious agent, comprising administering at least one effective dose of a modified or mutated RSV F protein, an RSV F micelle comprising a modified or mutated RSV F protein, or a VLP comprising a modified or mutated RSV F protein. In one embodiment, the method comprises administering VLPs further comprising a RSV M protein, such as BRSV M protein, and at least one protein from another infectious agent. In one embodiment, the method comprises administering VLPs further comprising a BRSV M protein and at least one protein from the same or a heterologous infectious agent. In another embodiment, the protein from the infectious agent is a viral protein. In another embodiment, the protein from the infectious agent is an envelope associated protein. In another embodiment, the protein from the infectious agent is expressed on the surface of VLPs. In another embodiment, the protein from the infectious agent comprises an epitope that will generate a protective immune response in a vertebrate. In another embodiment, the protein from the infectious agent can associate with RSV M protein. In another embodiment, the protein from the infectious agent can associate with BRSV M protein. In another embodiment, the protein from the infectious agent is fused to a RSV protein. In another embodiment, only a portion of a protein from the infectious agent is fused to a RSV protein. In another embodiment, only a portion of a protein from the infectious agent is fused to a portion of a RSV protein. In another embodiment, the portion of the protein from the infectious agent fused to the RSV protein is expressed on the surface of VLPs. In other embodiment, the RSV protein, or portion thereof, fused to the protein from the infectious agent associates with the RSV M protein. In other embodiment, the RSV protein, or portion thereof, fused to the protein from the infectious agent associates with the BRSV M protein. In other embodiment, the RSV protein, or portion thereof, is derived from RSV F, G, N and/or P. In another embodiment, the VLPs further comprise N and/or P protein from RSV. In another embodiment, the VLPs comprise more than one protein from the infectious agent. In another embodiment, the VLPs comprise more than one infectious agent protein, thus creating a multivalent VLP.

In another embodiment, the invention comprises a method of inducing a protective antibody response to an infection or at least one symptom thereof in a subject, comprising administering at least one effective dose of a modified or mutated RSV F protein, an RSV F micelle comprising a modified or mutated RSV F protein, or a VLP comprising a modified or mutated RSV F protein as described above.

As used herein, an "antibody" is a protein comprising one or more polypeptides substantially or partially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. A typical immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. Antibodies exist as intact immunoglobulins or as a number of well-characterized fragments produced by digestion with various peptidases.

In one embodiment, the invention comprises a method of inducing a protective cellular response to RSV infection or at least one disease symptom in a subject, comprising administering at least one effective dose of a modified or mutated RSV F protein. In another embodiment, the invention comprises a method of inducing a protective cellular response to RSV infection or at least one disease symptom in a subject, comprising administering at least one effective dose an RSV F micelle comprising a modified or mutated RSV F protein. In yet another embodiment, the invention comprises a method of inducing a protective cellular response to RSV infection or at least one disease symptom in a subject, comprising administering at least one effective dose a VLP, wherein the VLP comprises a modified or mutated RSV F protein as described above. Cell-mediated immunity also plays a role in recovery from RSV infection and may prevent RSV-associated complications. RSV-specific cellular lymphocytes have been detected in the blood and the lower respiratory tract secretions of infected subjects. Cytolysis of RSV-infected cells is mediated by CTLs in concert with RSV-specific antibodies and complement. The primary cytotoxic response is detectable in blood after 6-14 days and disappears by day 21 in infected or vaccinated individuals (Ennis et al., 1981). Cell-mediated immunity may also play a role in recovery from RSV infection and may prevent RSV-associated complications. RSV-specific cellular lymphocytes have been detected in the blood and the lower respiratory tract secretions of infected subjects.

As mentioned above, the immunogenic compositions of the invention prevent or reduce at least one symptom of RSV infection in a subject. Symptoms of RSV are well known in the art. They include rhinorrhea, sore throat, headache, hoarseness, cough, sputum, fever, rales, wheezing, and dyspnea. Thus, the method of the invention comprises the prevention or reduction of at least one symptom associated with RSV infection. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a RSV infection or additional symptoms, a reduced severity of a RSV symptoms or a suitable assays (e.g. antibody titer and/or T-cell activation assay). The objective assessment comprises both animal and human assessments.

This invention is further illustrated by the following examples that should not be construed as limiting. The contents of all references, patents and published patent applications cited throughout this application, as well as the Figures and the Sequence Listing, are incorporated herein by reference for all purposes.

EXAMPLES

Example 1

Generating Recombinant Bacmids, Transfection of Insect Cells to Make Recombinant Virus Stocks, Plaque Purification, and Infecting Insect Cells with Primary Virus Stock.

To construct recombinant virus, the viral genes of interest were codon optimized for Sf9 insect cells expression and cloned into pFastBac™ vectors.

Once the desired constructs were confirmed and purified, one vial of MAX Efficiency® DH10Bac™ competent cells for each construct was thawed on ice. Approximately 1 ng (5 µl) of the desired pFastBac™ construct plasmid DNA was added to the cells and mixed gently. The cells were incubated on ice for 30 minutes. This was followed by heat-shock of the cells for 45 seconds at 42° C. without shaking. Next, the tubes were transferred to ice and chilled for 2 minutes. Subsequently 900 µl of room temperature S.O.C. Medium was added to each tube. The tubes were put on a shaker at 37° C. at 225 rpm for 4 hours. For each pFastBac™ transformation, 10-fold serial dilutions of the cells (10-1, 10-2 and 10-3) was prepared using S.O.C. medium. Next, 100 µl of each dilution was plated on an LB agar plate containing 50 µg/ml kanamycin, 7 µg/ml gentamicin, 10 µg/ml tetracycline, 100 µg/ml Bluo-gal, and 40 µg/ml IPTG. The plates were incubated for 48 hours at 37° C. White colonies were picked for analysis.

Different bacmid DNAs from above were made for each construct and were isolated. These DNAs were precipitation and added to Sf9 cells for 5 hours.

Next, 30 ml of Sf9 insect cells ($2 \times 10^6$ cells/ml) were infected with baculovirus expressing viral proteins of interest with 0.3 ml of plaque eluate and incubated 48-72 hrs. Approximately 1 ml of crude culture (cells+medium) and clarified culture harvests were saved for expression analysis and the rest were saved for purification purposes.

Example 2

Expression, Purification, and Analysis of Modified HRSV F Proteins

Genes encoding modified HRSV F proteins of interest were synthesized in vitro as overlapping oligonucleotides, cloned and expressed in host cells. Cloning and expression of the modified RSV F genes were achieved following the methods known in the art.

Recombinant plaques containing viral proteins of interest were picked and confirmed. The recombinant virus was then amplified by infection of Sf9 insect cells. In some cases, Sf9 insect cells were co-infected by a recombinant virus expressing modified F protein and another recombinant virus expressing other viral proteins (e.g., BRSV M protein and/or HRSV N protein). A culture of insect cells was infected at ~3 MOI (Multiplicity of infection =virus ffu or pfu/cell) with baculovirus carrying the various constructs. The culture and supernatant were harvested 48-72 post-infection. The crude harvest, approximately 30 mL, was clarified by centrifugation for 15 minutes at approximately 800×g. The resulting crude cell harvests containing modified HRSV F protein were purified as described below.

Modified HRSV F proteins of interest were purified from the infected Sf9 insect cell culture harvests. Non-ionic surfactant Tergitol® NP-9 (Nonylphenol Ethoxylate) was used to in a membrane protein extraction protocol. Crude extraction was further purified by passing through anion exchange chromatography, lentil lectin affinity/HIC, and cation exchange chromatography.

Protein expression was analyzed by SDS-PAGE and stained for total proteins by coomassie stain. Equal volumes of cell samples from crude harvest and 2× sample buffer containing βME (beta-mercaptoehtanol) were loaded, approximately 15 to 20 µl (about to 7.5 to 10 µl of the culture)/lane, onto an SDS Laemmli gel.

In some cases, instead of chromatography, modified HRSV F proteins in the crude cell harvests were concentrated by 30% sucrose gradient separation method, and then were analyzed by SDS-PAGE stained with coomassie, or Western Blot using anti-RSV F monoclonal antibody.

Crude cell harvest containing modified recombinant F proteins, purified recombinant F proteins, or recombinant F proteins concentrated by sucrose gradient can be further analyzed by Western Blot using anti-RSV F monoclonal antibody and/or anti-RSV F polyclonal antibody.

Example 3

Modified HRSV F Gene Encoding F Protein BV #541

Initial attempts to express the full length HRSV F protein proved unsuccessful in achieving high levels of expression. The F gene sequence used in the expression was SEQ ID NO: 1 (wild type HRSV F gene, GenBank Accession No. M11486). It encodes an inactive precursor ($F_0$) of 574 aa. This precursor is cleaved twice by furin-like proteases during maturation to yield two disulfide-linked polypeptides, subunit $F_2$ from the N terminus and $F_1$ from the C terminus (FIG. 1). The two cleavages sites are at residues 109 and 136, which are preceded by furin-recognition motifs (RARR, aa 106-109 (SEQ ID NO: 23) and KKRKRR, aa 131-136 (SEQ ID NO: 24)). The F gene sequence of SEQ ID NO: 1 contains suboptimal codon usage for expression in Sf9 insect cells and harbors 3 errors, producing a protein that can exhibit less than optimal folding (SEQ ID NO: 2, GenBank Accession No. AAB59858). In addition, a possible Poly (A) adenylation site (ATAAAA) was identified at the region encoding the $F_2$ subunit. Moreover, the wild type F gene sequence is approximately 65% AT rich, while desired GC-AT ratio of a gene sequence in Sf9 insect cell expression system is approximately 1:1.

In attempt to overcome poor expression levels of HRSV F protein, a new F gene sequence was designed so that:
 (a) the three GenBank sequencing errors were corrected;
 (b) the cryptic poly (A) site at the region encoding $F_2$ subunit was modified;
 (c) F gene codons were optimized; and
 (d) the F gene encodes a modified F protein with inactivated primary cleavage site.

The three corrected amino acids errors were P102A, I379V, and M447V. The cryptic poly (A) site in the HRSV F gene was corrected without changing the amino acid sequence.

The codon optimization scheme was based on the following criteria: (1) abundance of aminoacyl-tRNAs for a particular codon in Lepidopteran species of insect cells for a given amino acid as described by Levin, D. B. et al. (Journal of General Virology, 2000, vol. 81, pp. 2313-2325), (2) maintenance of GC-AT ratio in gene sequences at approximately 1:1, (3) minimal introduction of palindromic or stem-loop DNA structures, and (4) minimal introduction of transcription and post-transcription repressor element sequences. An example of optimized F gene sequence was shown as SEQ ID NO: 19 (RSV-F BV #368).

Figure 2:
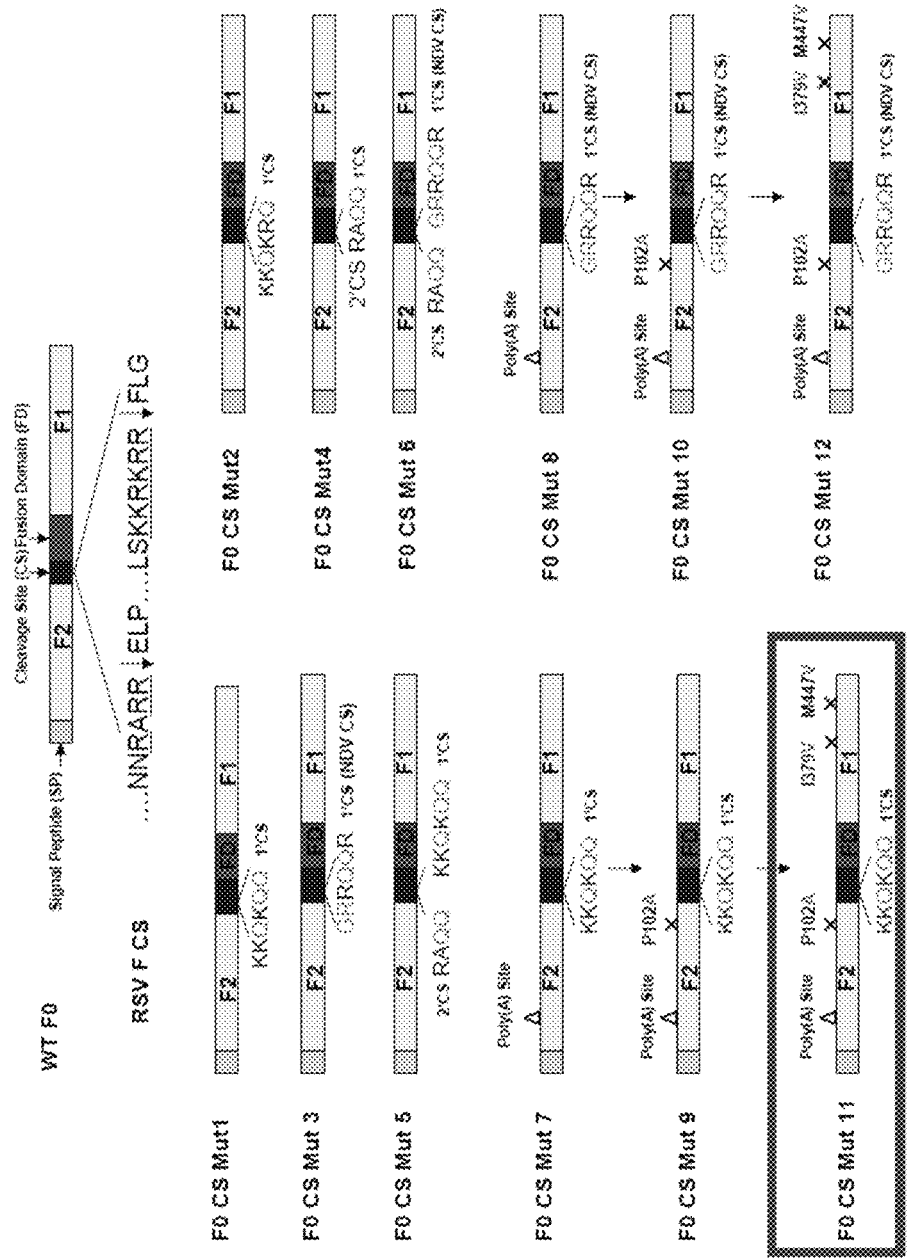
FIG. 2 depicts structures of modified RSV $F_0$ proteins with cleavage site mutations as described in Example 3. The cleavage site regions are shown as NNRARRELP (SEQ ID NO:30) and LSKKRKRRFLG (SEQ ID NO:31). Particular cleavage site sequences are shown as KKQKQQ (SEQ ID NO:28), GRRQQR (SEQ ID NO:29), KKQKRQ (SEQ ID NO:32), RAQQ (SEQ ID NO:33), and RANN (SEQ ID NO:34).
Figure 3:
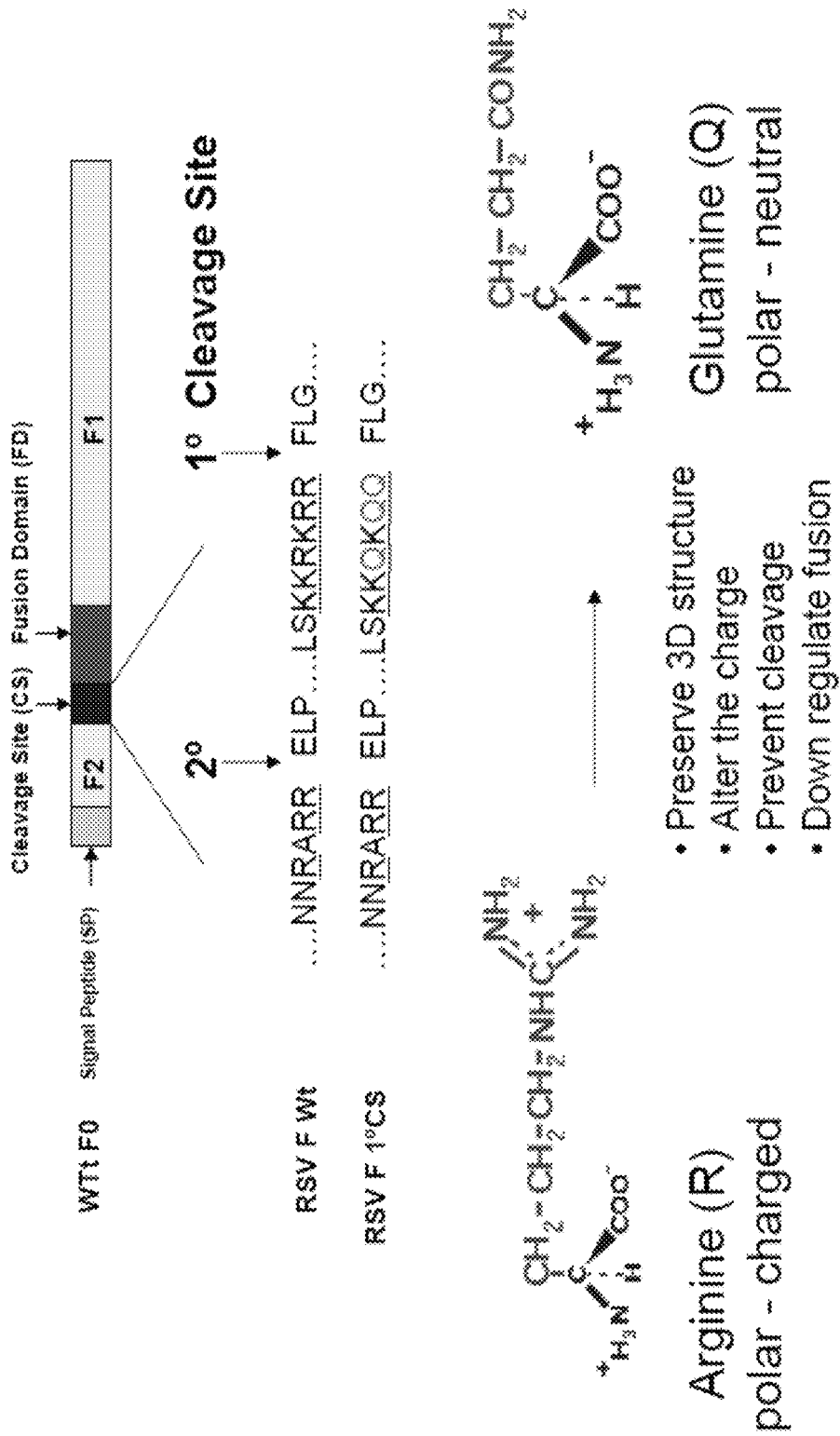
FIG. 3 depicts conservative substitutions (R133Q, R135Q and R136Q) in the primary cleavage site of modified HRSV F protein BV #541 (SEQ ID NO: 6). The mutated cleavage site region is shown as LSKKQKQQFLG (SEQ ID NO:35).

To inactivate the primary cleavage site (1° CS, KKRKRR, aa 131-136) of HRSV F protein, the furin recognition site was mutated to either KKQKQQ (SEQ ID NO: 28) or GRRQQR (SEQ ID NO: 29). Several modified F proteins with such cleavage site mutations were evaluated to determine the efficiency of cleavage prevention. FIG. 2 shows several of the modified F proteins that were evaluated. The results indicate that the primary cleavage site of HRSV F protein can be inactivated by three conservative amino acid changes R133Q, R135Q, and R136Q. These conservative amino acid changes from Arginine (R) which is a polar-charged molecule, to Glutamine (Q) which is a polar-neutral molecule, altered the charge status at these sites and prevented cleavage by furin-like proteases (see FIG. 3), while still preserving the F protein 3D structure. Prevention of cleavage at 1° CS resulted in reduced membrane fusion activity of the F protein.

Figure 4:
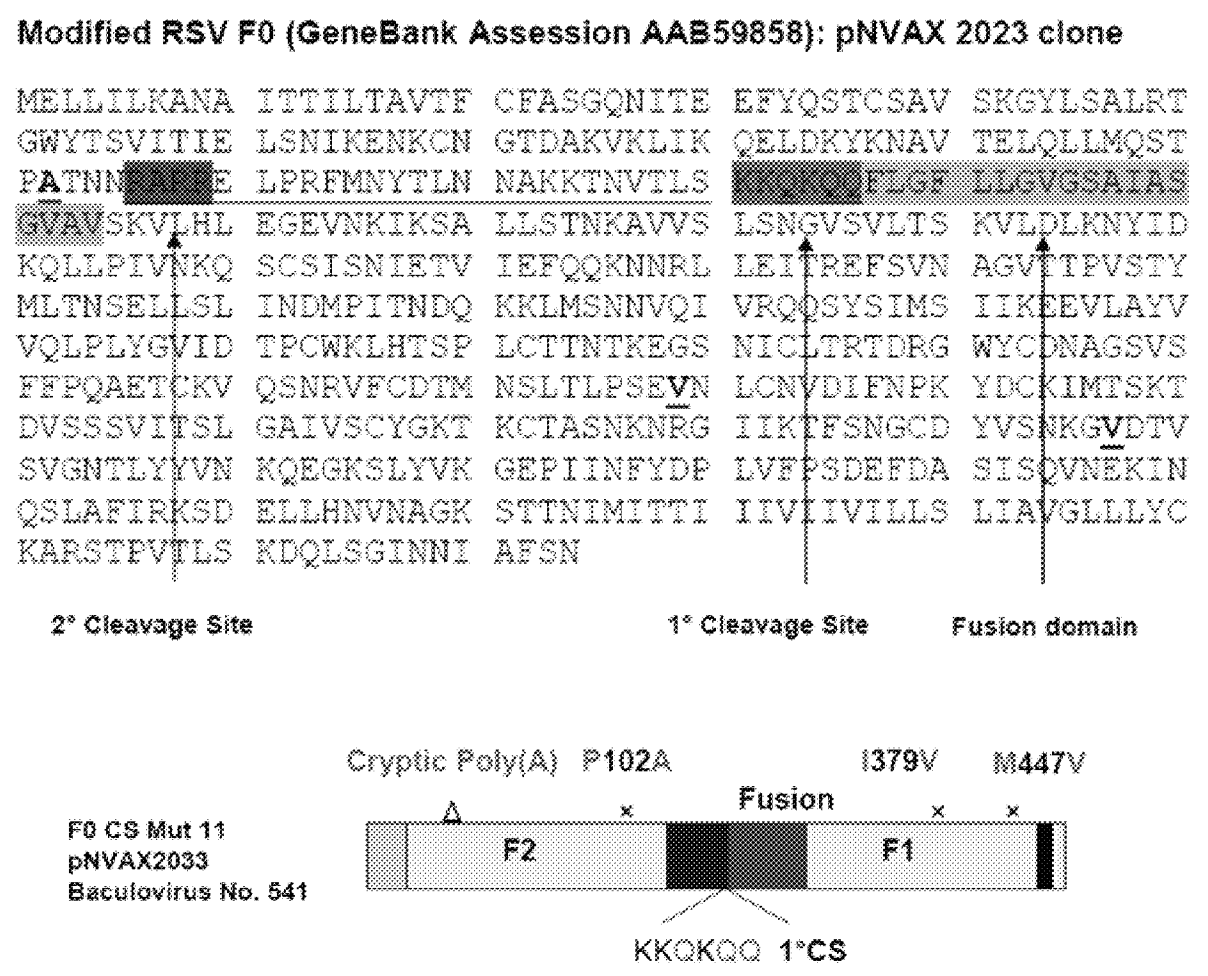

A non-limiting exemplary modified HRSV F gene sequence designed to have all modifications mentioned above is shown in FIG. 4. This modified F gene (SEQ ID NO: 5, RSV-F BV #541) encodes a modified F protein of SEQ ID NO: 6. The gene sequence was synthesized in vitro as overlapping oligonucleotides, cloned and expressed in host cells. Modified HRSV F protein BV #541 was purified from the infected Sf9 insect cell culture harvests, and was analyzed by SDS-PAGE stained by coomassie. The method of purification and SDS-PAGE analysis is described in Example 2. The expression level of the F protein RSV-F BV #541 (e.g. F protein 541) was improved as compared to the wild type $F_0$ protein in Sf9 insect cells.

Example 4

Modified HRSV F Protein with $F_1$ Subunit Fusion Domain Partial Deletion

To further improve expression of the RSV F protein, additionally modified HRSV F genes were designed that comprised the following modifications:
 (a) the three GenBank sequencing errors were corrected;
 (b) the cryptic poly (A) site at the region encoding F2 subunit was modified;
 (c) F gene codons were optimized; and
 (d) the nucleotide sequences encoding the $F_1$ subunit fusion domain was partially deleted. In one experiment, the nucleotide sequence encoding the first 10 amino acids of the $F_1$ subunit fusion domain was deleted (corresponding to amino acids 137-146 of SEQ ID NO: 2).

Figure 5:
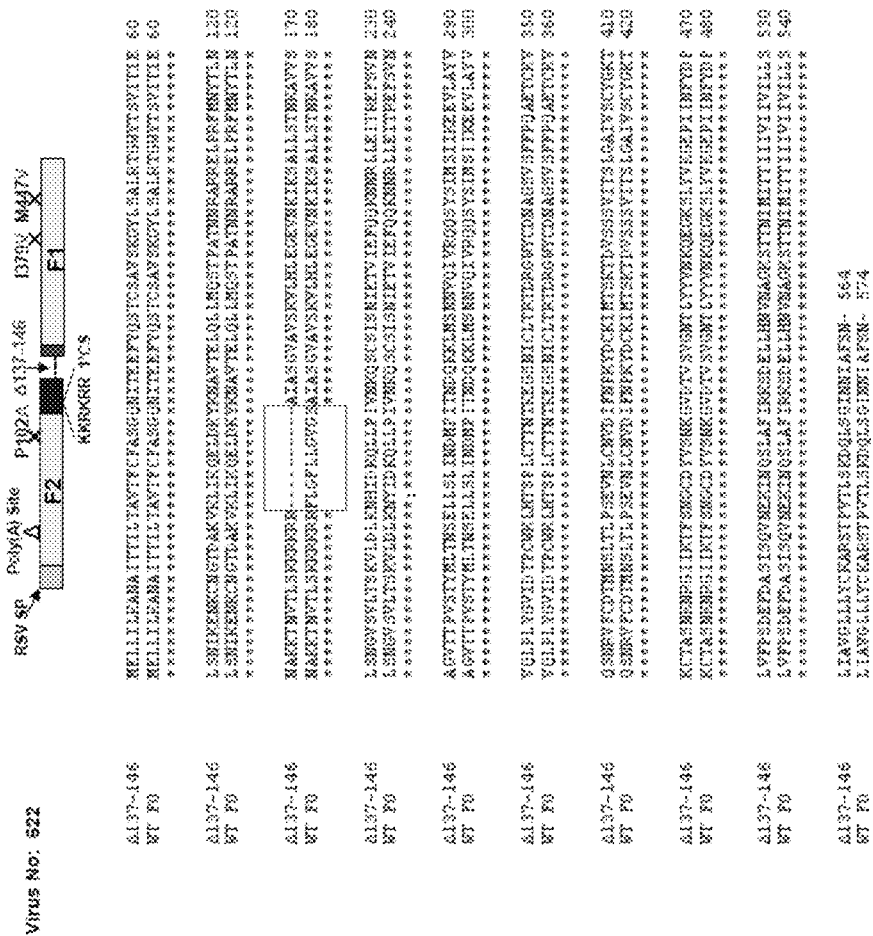
FIG. 5 depicts sequence and structure of modified HRSV F protein BV #622 (SEQ ID NO: 10), and the KKRKRRcleavage site (SEQ ID NO:24).
Figure 6:
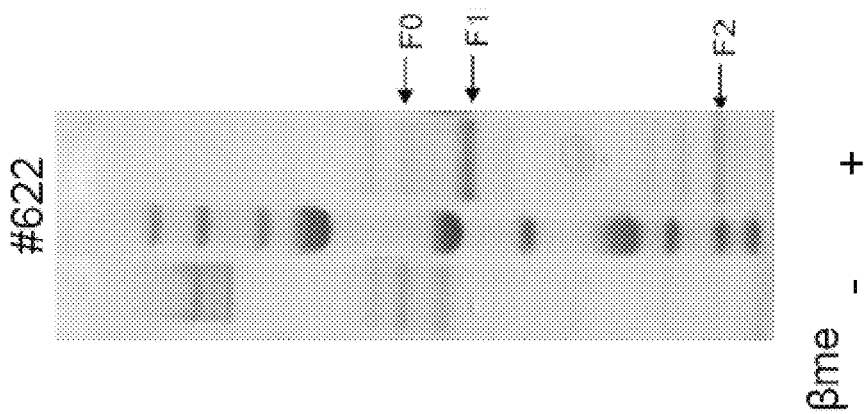
FIG. 6 depicts SDS-PAGE coomassie-stained gel of purified recombinant HRSV F protein BV #622 with or without the presence of βME.

A non-limiting exemplary modified RSV F gene comprising said modifications is shown in FIG. 5, designated as SEQ ID NO: 9 (RSV-F BV #622, e.g. F protein 622), encoding a modified F protein of SEQ ID NO: 10. The modified HRSV F protein BV #622 was purified from the infected Sf9 insect cell culture harvests, and was analyzed by SDS-PAGE stained with coomassie. The method of purification and SDS-PAGE analysis is described in Example 2. High expression levels of HRSV F protein BV #622 were observed, as displayed in the SDS-PAGE in FIG. 6.

Example 5

Modified HRSV F Protein with Both Inactivated Primary Cleavage Site and $F_1$ Fusion Domain Partial Deletion To determine if the combination of inactivated primary cleavage site and $F_1$ fusion domain partial deletion can further promote expression of the RSV F protein, particularly in the Sf9 insect cells, another modified RSV F gene was designed comprising following modifications:

(a) the three GenBank sequencing errors were corrected;
(b) the cryptic poly (A) site at the region encoding F2 subunit was modified;
(c) F gene codons were optimized;
(d) the primary cleavage site was inactivated; and
(e) the nucleotide sequence encoding the F1 subunit fusion domain was partially deleted. In one experiment, the nucleotide sequence encoding the first 10 amino acids of the $F_1$ subunit fusion domain was deleted (corresponding to amino acids 137-146 of SEQ ID NO: 2).

Figure 8:
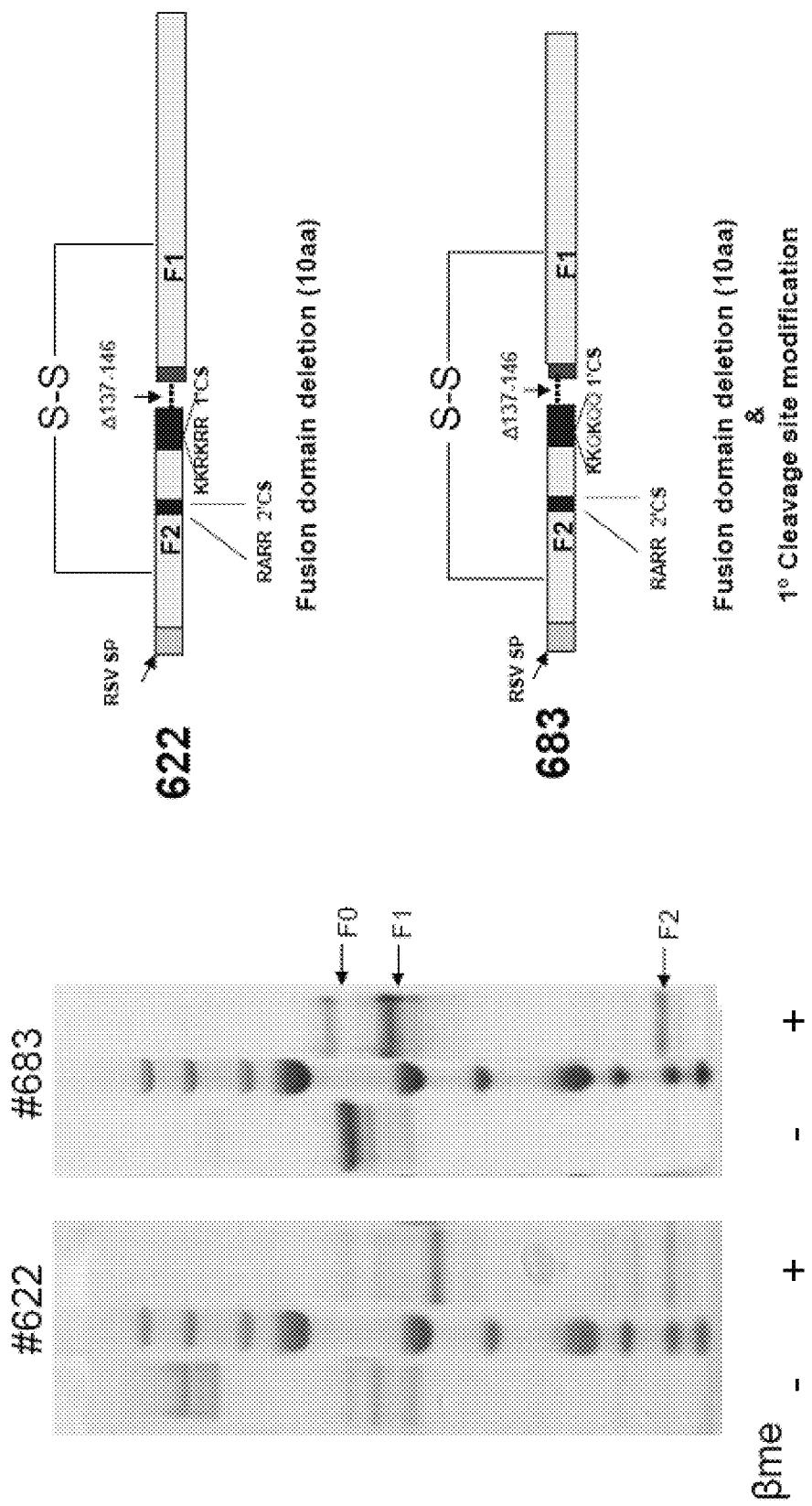
FIG. 8 depicts SDS-PAGE coomassie-stained gels of purified recombinant HRSV F proteins BV #622 and BV #683 with or without the presence of βME (on the left), and their structures; as well as the KKQKQQ cleavage site (SEQ ID NO:28) and the KKRKRRcleavage site (SEQ ID NO:24).

An non-limiting exemplary modified RSV F gene comprising said modifications is shown in FIG. 7, designated as SEQ ID NO: 7 (RSV-F BV #683, e.g. F protein 683), encoding the modified F protein of SEQ ID NO: 8. The modified RSV F protein BV #683 (e.g. F protein 683) was purified from the infected Sf9 insect cell culture harvests and analyzed by SDS-PAGE stained with coomassie. The method of purification and SDS-PAGE analysis is described in Example 2. Further enhancements in the of expression levels were achieved, as displayed in the SDS-PAGE in FIG. 8.

Example 6

Expression and Purification of Modified HRSV F Protein BV #683

Modified HRSV F protein BV #683 (e.g. F protein 683, SEQ ID NO: 8) was expressed in baculovirus expression system as describe in Example 1, and recombinant plaques expressing HRSV F protein BV #683 were picked and confirmed. The recombinant virus was then amplified by infection of Sf9 insect cells. A culture of insect cells was infected at ~3 MOI (Multiplicity of infection=virus ffu or pfu/cell) with baculovirus. The culture and supernatant were harvested 48-72 hrs post-infection. The crude harvest, approximately 30 mL, was clarified by centrifugation for 15 minutes at approximately 800×g. The resulting crude cell harvests containing HRSV F protein BV #683 were purified as described below.

HRSV F protein BV #683 was purified from the infected Sf9 insect cell culture harvests. Non-ionic surfactant Tergitol® NP-9 (Nonylphenol Ethoxylate) was used to in a membrane protein extraction protocol. Crude extraction was further purified by passing through anion exchange chromatography, lentil lectin affinity/HIC and cation exchange chromatography.

Figure 9:
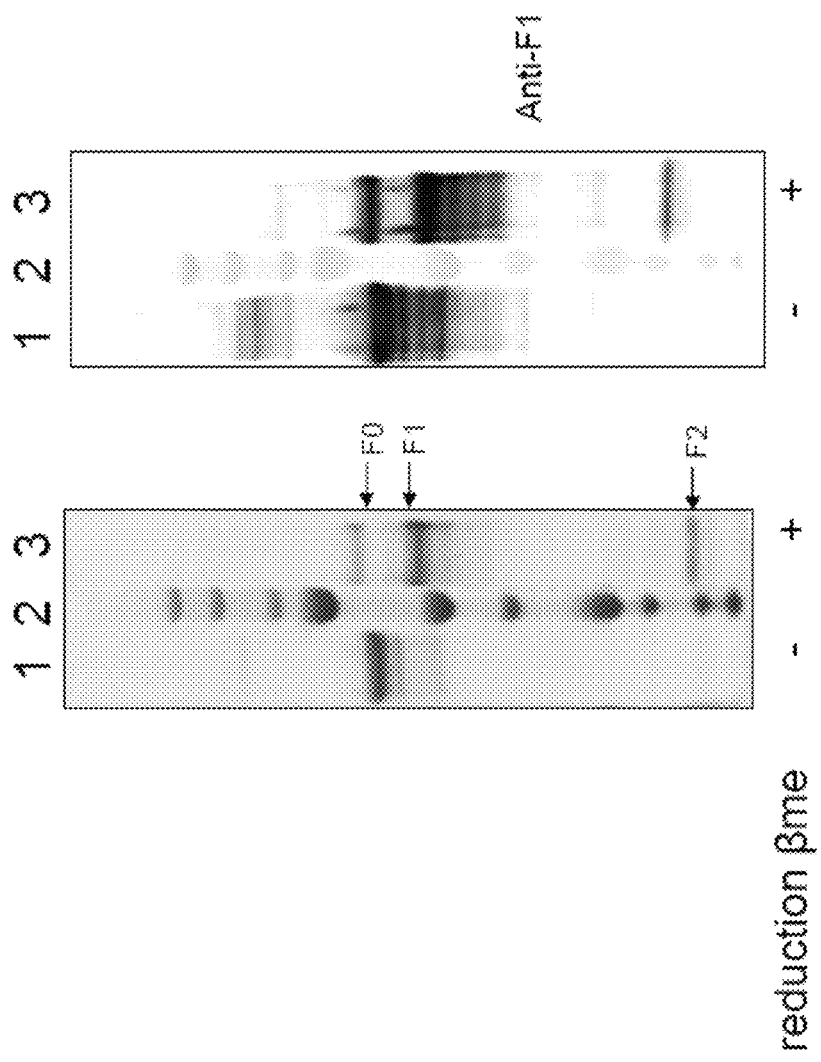
FIG. 9 depicts SDS-PAGE coomassie-stained gel (on the left) and Western Blot (on the right) analysis of purified recombinant HRSV F protein BV #683 with or without the presence of βME.
Figure 10:
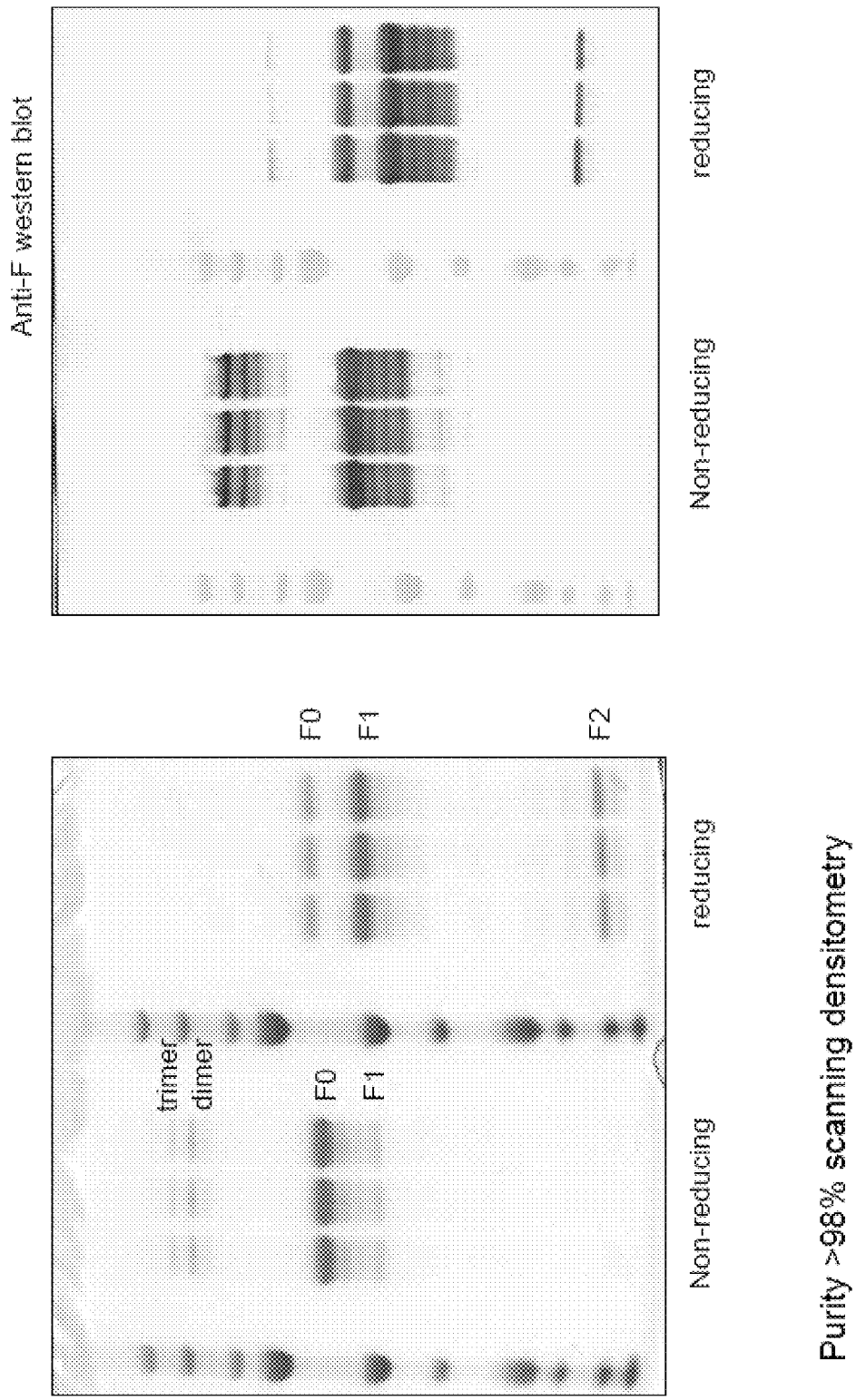
FIG. 10 depicts SDS-PAGE coomassie-stained gel used in purity analysis by scanning densitometry (on the left) and Western Blot (on the right) of purified recombinant HRSV F protein BV #683.

Purified HRSV F protein BV #683 was analyzed by SDS-PAGE stained with coomassie, and Western Blot using anti-RSV F monoclonal antibody as described in Example 2. The results were shown in FIG. 9. Excellent expression levels of the HRSV F protein BV #683 (e.g. F protein 683, SEQ ID NO: 8) were achieved. It was estimated that the expression level was above 10 mg/L in crude cell culture, and recovered F protein BV #683 was about 3.5 mg/L cell culture. In some cases expression levels above 20 mg/L were achieved and about 5 mg/L modified F protein BV #683 was recovered (see FIG. 10). Purity of the recovered F protein BV #683 reached above 98% as determined by scanning densitometry (see FIG. 10).

Example 7

Purified HRSV F Protein BV #683 Micelles (Rosettes)

Figure 11:
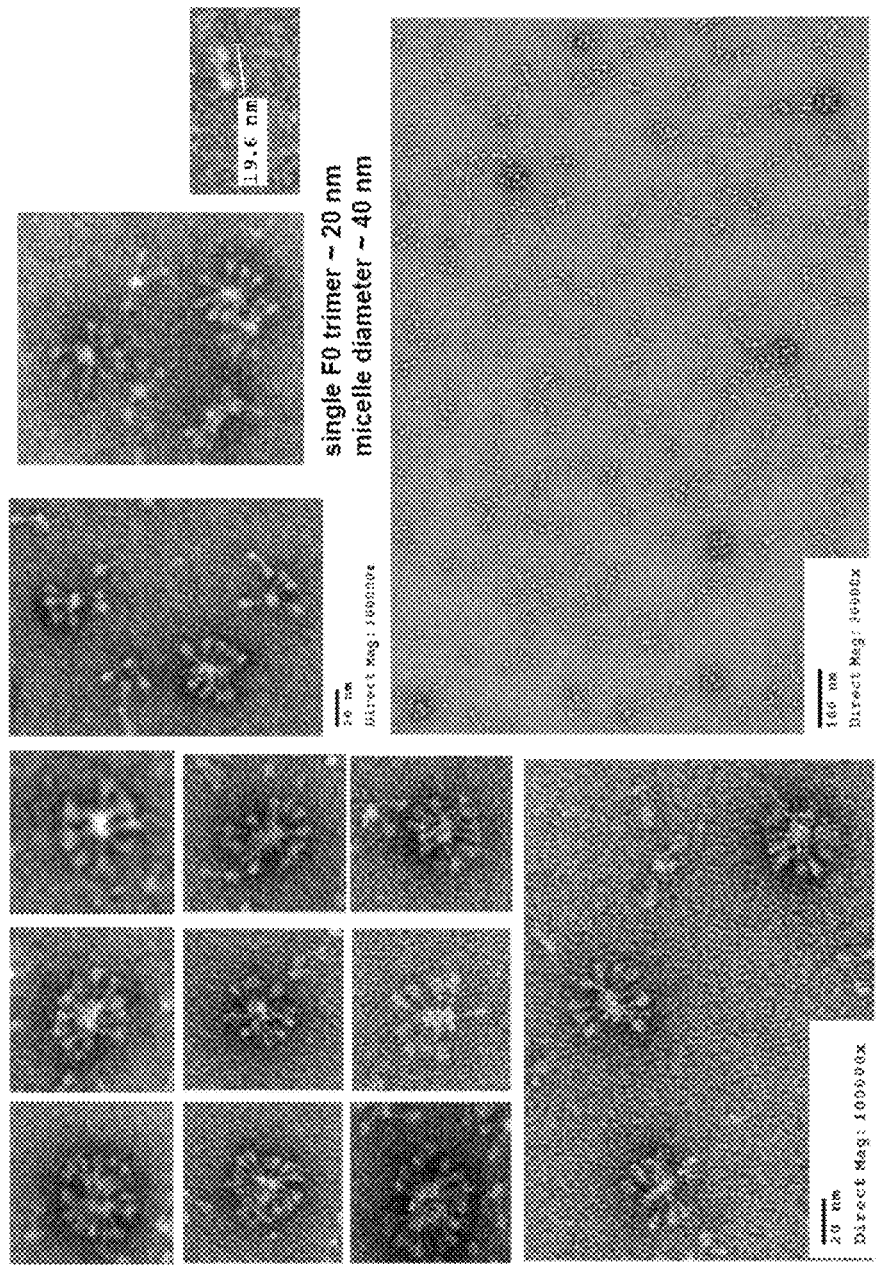
FIG. 11 depicts images of purified recombinant HRSV F protein BV #683 micelles (rosettes) taken in negative stain electron microscopy.
Figure 12:
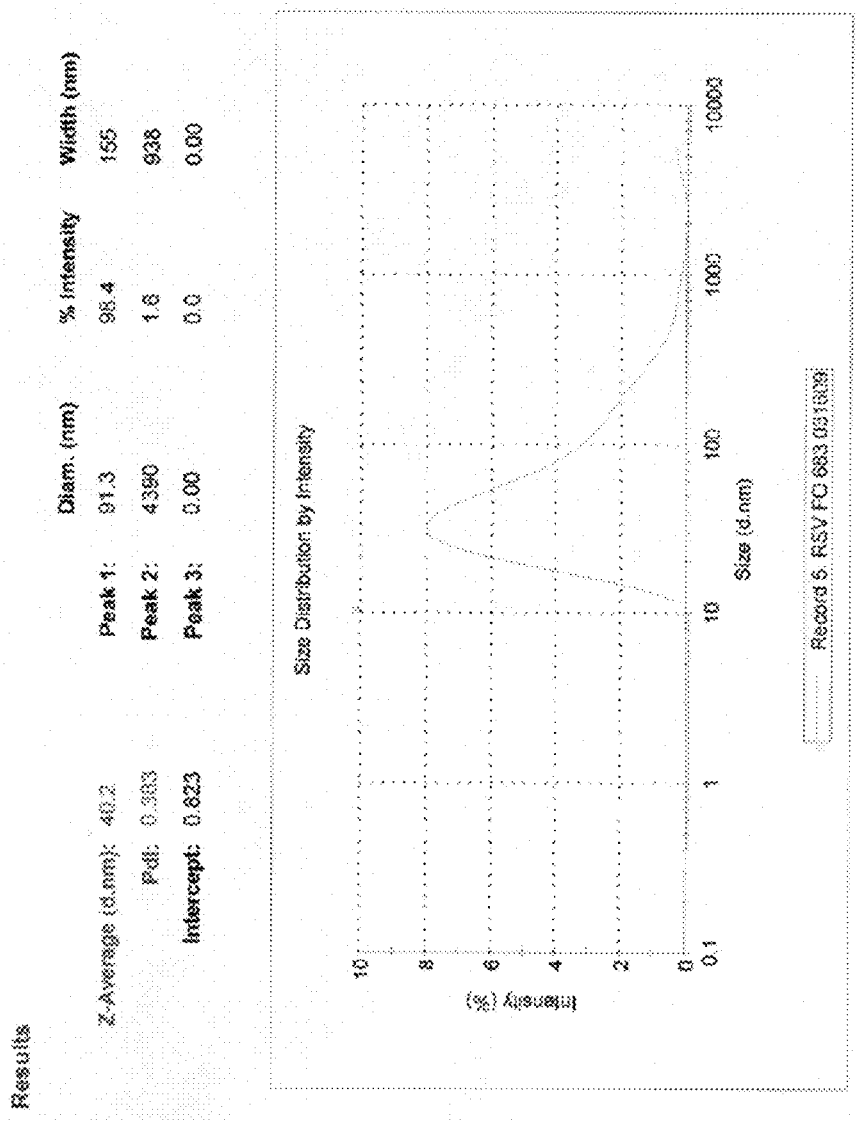
FIG. 12 depicts particle size analysis of HRSV F protein BV #683 micelles.

Purified HRSV F protein BV #683 was analyzed by negative stain electron microscopy (see FIG. 11). F proteins aggregated in the form of micelles (rosettes), similar to those observed for wild type HRSV F protein (Calder et al., 2000, Virology 271, pp. 122-131), and other full-length virus membrane glycoproteins (Wrigley et al., Academic Press, London, 1986, vol. 5, pp. 103-163). Under electron microscopy, the F spikes exhibited lollipop-shaped rod morphology with their wider ends projecting away from the centers of the rosettes. The length of single trimer was about 20 nm, and the micelle particle diameter was about 40 nm (see FIG. 12). These results indicated that HRSV F protein BV #683 has correct 3D structure for a native, active protein.

In summary, a modified recombinant HRSV F protein (e.g., BV #683) has been designed, expressed, and purified. This modified full-length F is glycosylated. Modifications of the primary cleavage site and the fusion domain together greatly enhanced expression level of F protein. In addition, this modified F protein can be cleaved to $F_1$ and $F_2$ subunits, which are disulfide-linked. Trimers of the F1 and F2 subunits form lollipop-shaped spikes of 19.6 nm and particles of 40.2 nm. Moreover, this modified F protein is highly expressed in Sf9 insect cells. Purity of micelles>98% is achieved after purification. The fact that the spikes of this modified protein have a lollipop morphology, which can further form micelles particles of 40 nm, indicates that modified F protein BV #683 has correct 3D structure of a native protein.

Example 8

Co-Expression of Modified HRSV F Protein with BRSV M and/or HRSV N in VLP Production The present invention also provides VLPs comprising a modified or mutated RSV F protein. Such VLPs are useful to induce neutralizing antibodies to viral protein antigens and thus can be administered to establish immunity against RSV. For example, such VLPs may comprise a modified RSV F protein, and a BRSV M and/or HRSV N proteins. Codons of genes encoding BRSV M (SEQ ID NO: 14) or HRSV N (SEQ ID NO: 18) proteins can be optimized for expression in insect cells. For example, an optimized BRSV M gene sequence is shown in SEQ ID NO: 13 and an optimized RSV N gene sequence is shown in SEQ ID NO: 17.

Figure 13:
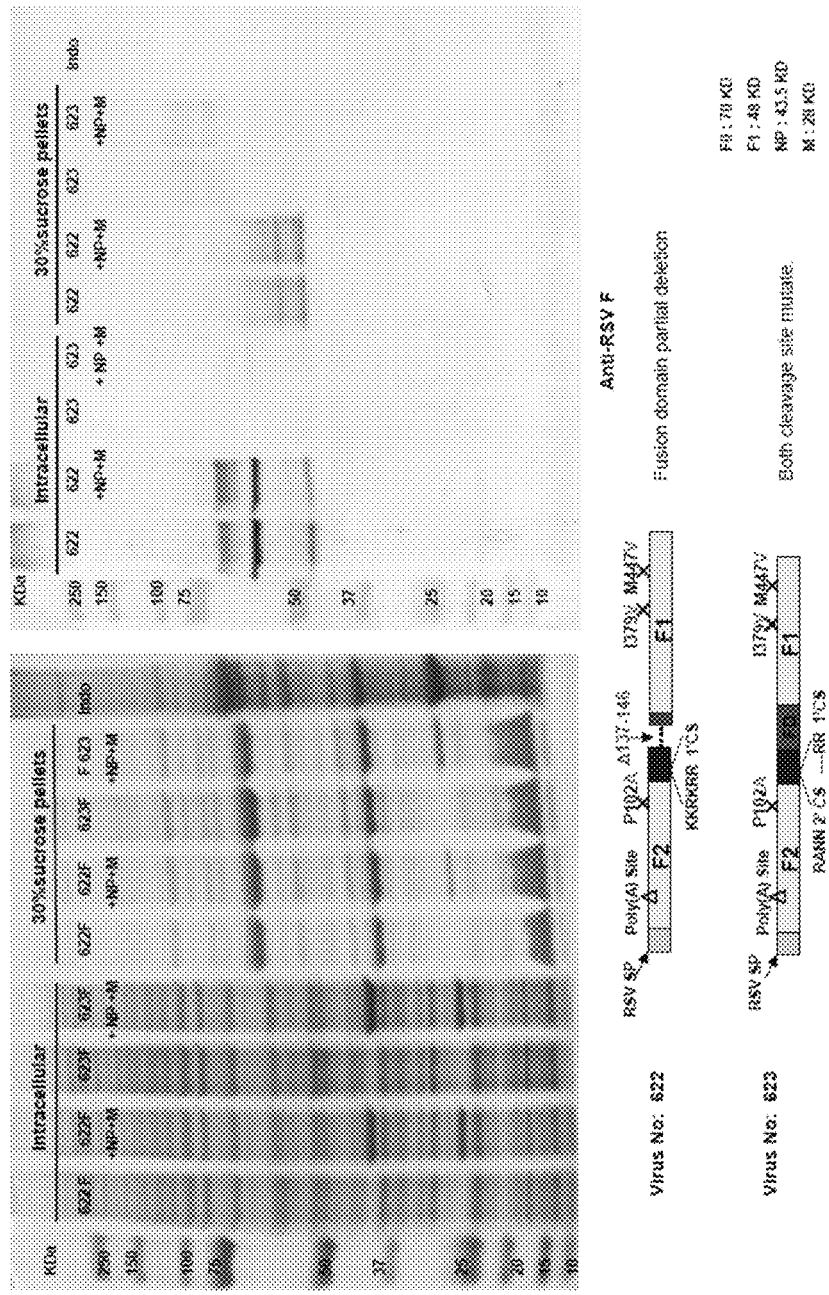
FIG. 13 depicts SDS-PAGE coomassie-stained gel (on the left) and Western Blot (on the right) analysis of modified HRSV F proteins BV #622 and BV #623 (SEQ ID NO: 21) with or without co-expression with HRSV N and BRSV M proteins in the crude cell culture harvests (intracellular) or pelleted samples by 30% sucrose gradient separation, and structures of BV #622 and BV #623. Also featured is the KKRKRRcleavage site (SEQ ID NO:24)
Figure 16A:
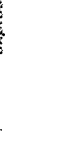
Figure 16D:
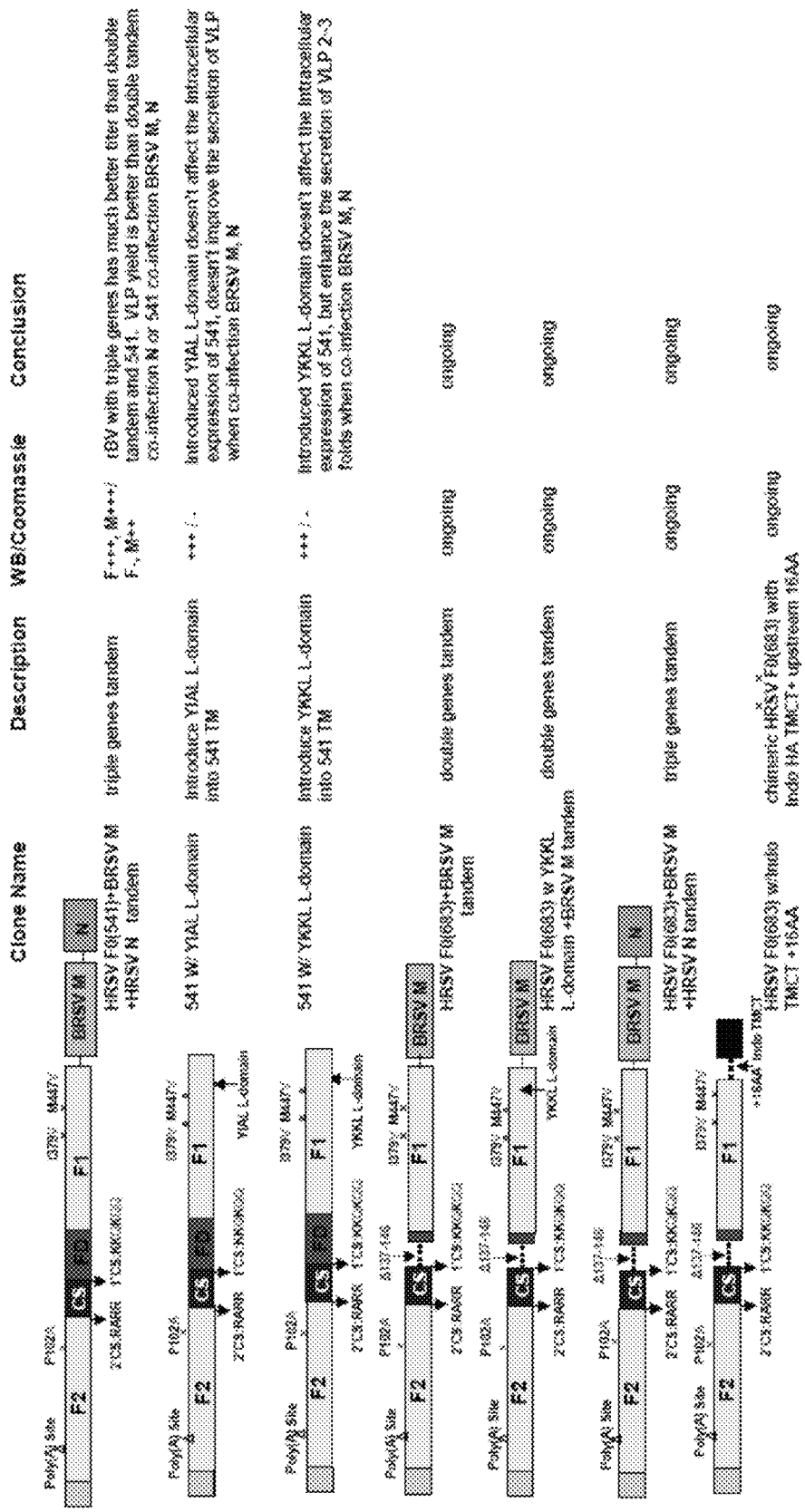
Figure 17:
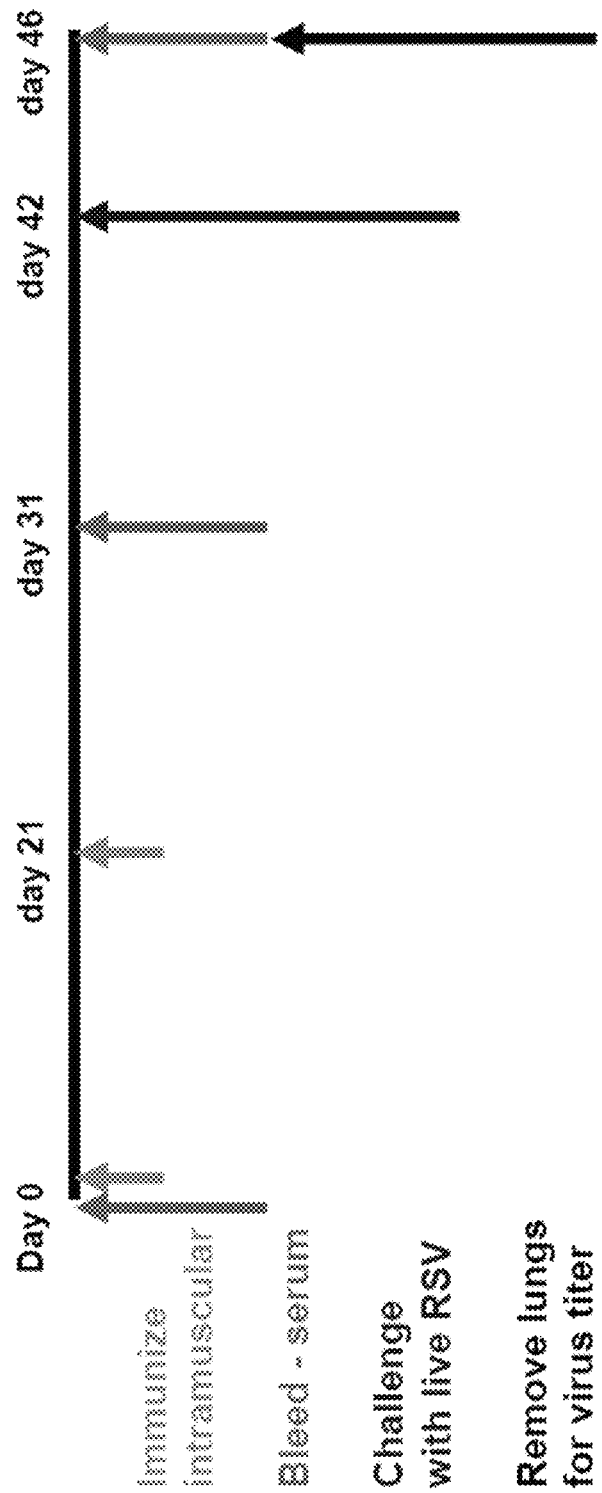
FIG. 17 depicts experimental procedures of the RSV challenge study as described in Example 10.
Figure 18:
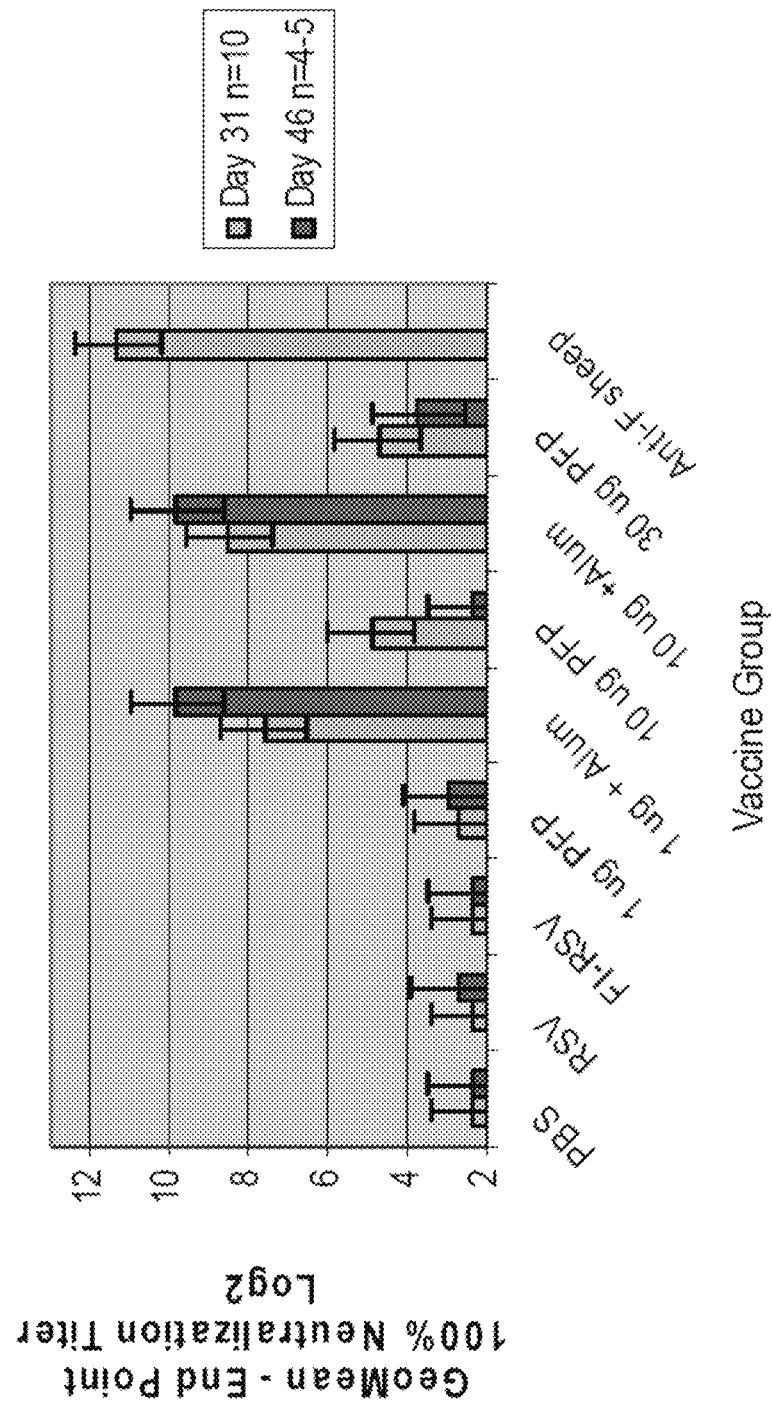
FIG. 18 depicts results of RSV neutralization assay at day 31 and day 46 of mice immunized with PBS, live RSV, FI-RSV, 1 ug PFP, 1 ug PFP+Alum, 10 ug PFP, 10 ug PFP+Alum, 30 ug PFP, and positive control (anti-F sheep).
Figure 19:
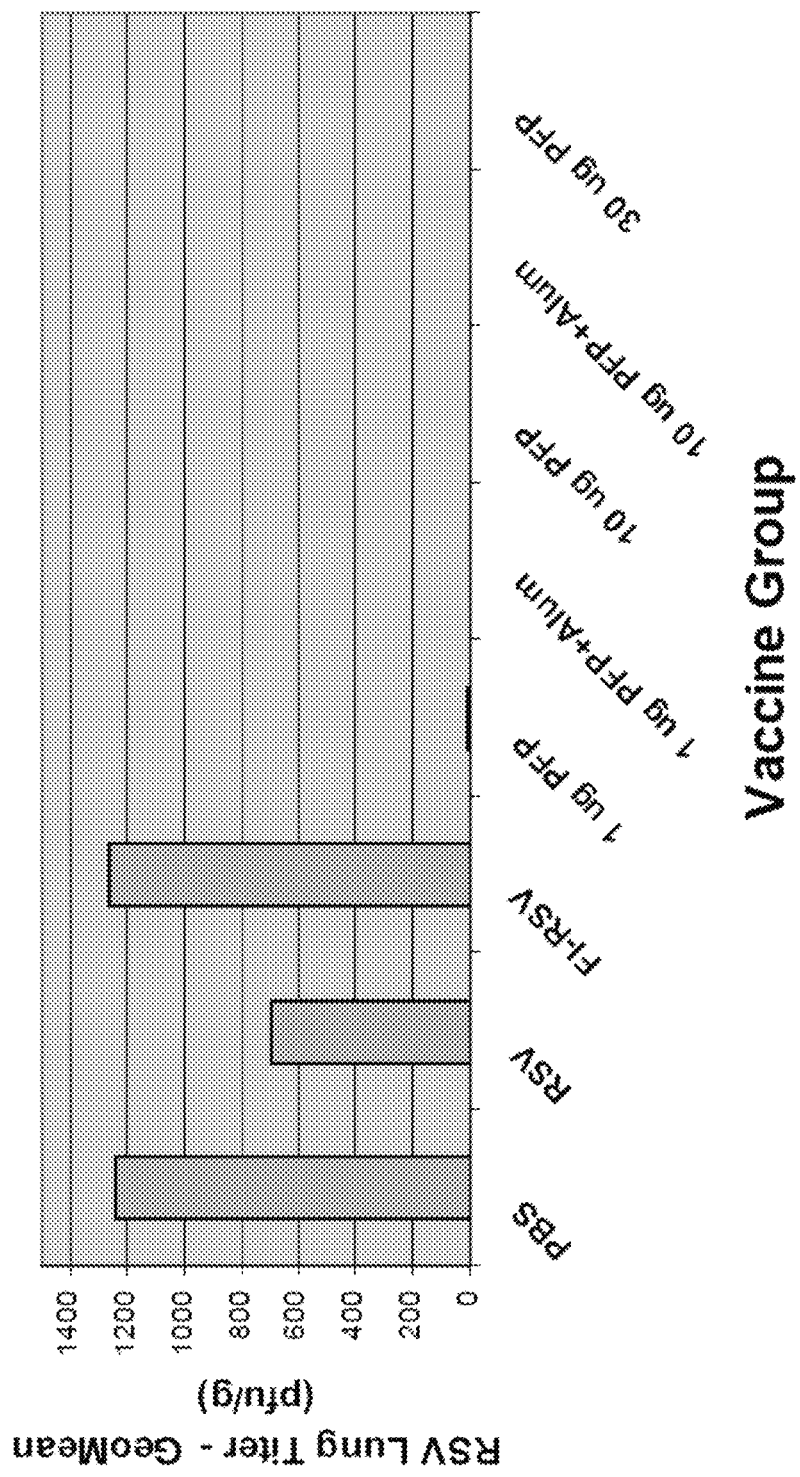
FIG. 19 depicts RSV titers in lung tissues of mice immunized with PBS, live RSV, FI-RSV, 1 ug PFP, 1 ug PFP+Alum, 10 ug PFP, 10 ug PFP+Alum, and 30 ug PFP, 4 days after challenge of infectious RSV.

In one experiment, a modified F protein BV #622 and another modified F protein BV #623 (SEQ ID NO: 21, modified such that both cleavage sites are inactivated) were either expressed alone, or co-expressed with HRSV N protein and BRSV M protein. Both crude cell harvests containing VLPs (intracellular) and VLPs pellets collected from 30% sucrose gradient separation were analyzed by SDS-PAGE stained with coomassie, and Western Blot using anti-RSV F monoclonal antibody. FIG. 13 shows the structure of the modified F proteins BV #622 and BV #623, and results of SDS-PAGE and Western Blot analysis. BV #622 was highly expressed by itself or co-expressed with HRSV N protein and BRSV M protein, while BV #623 had very poor expression, indicating inactivation of both cleavage sites inhibits F protein expression.

Figure 14:
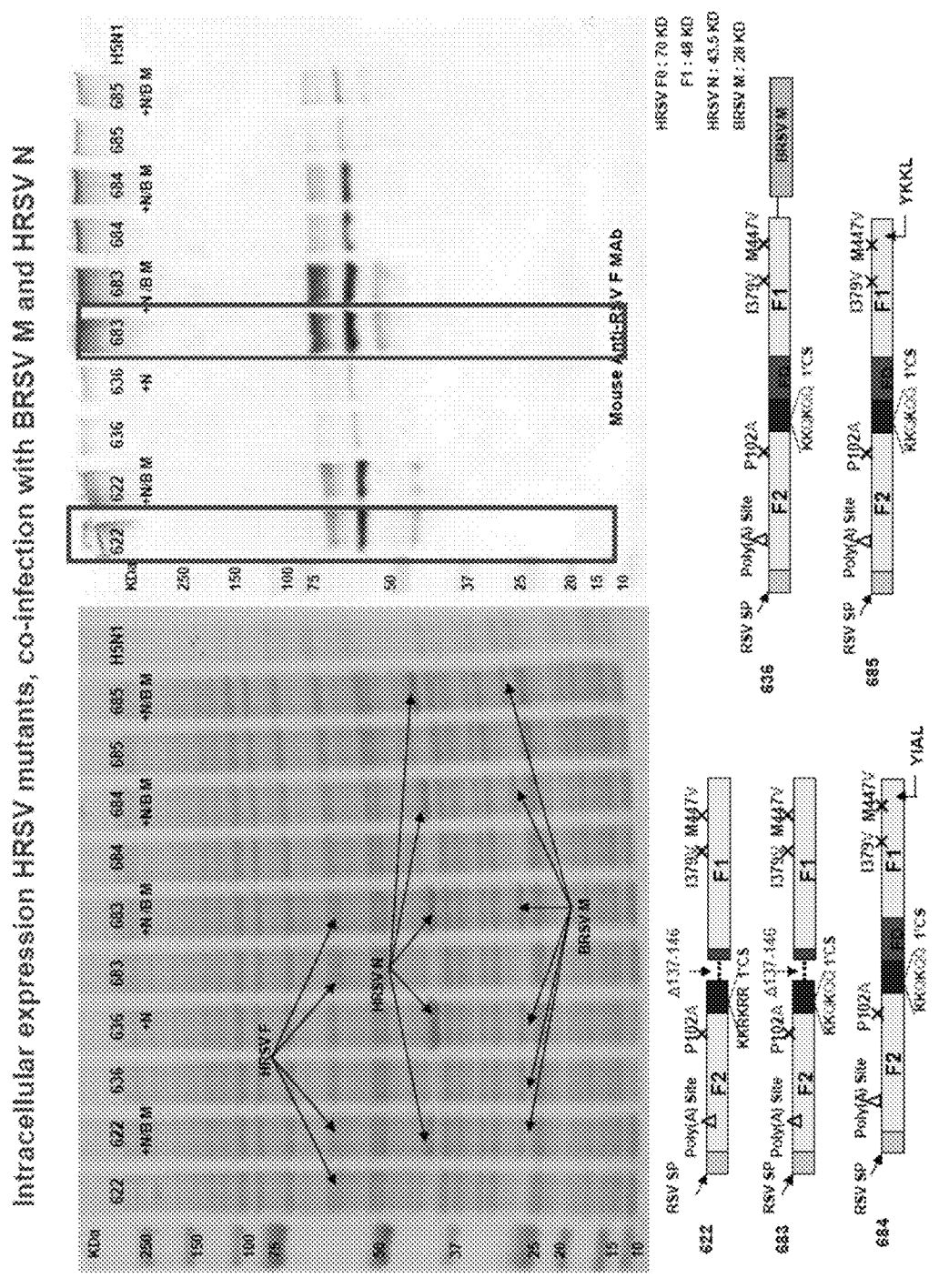
Figure 15:
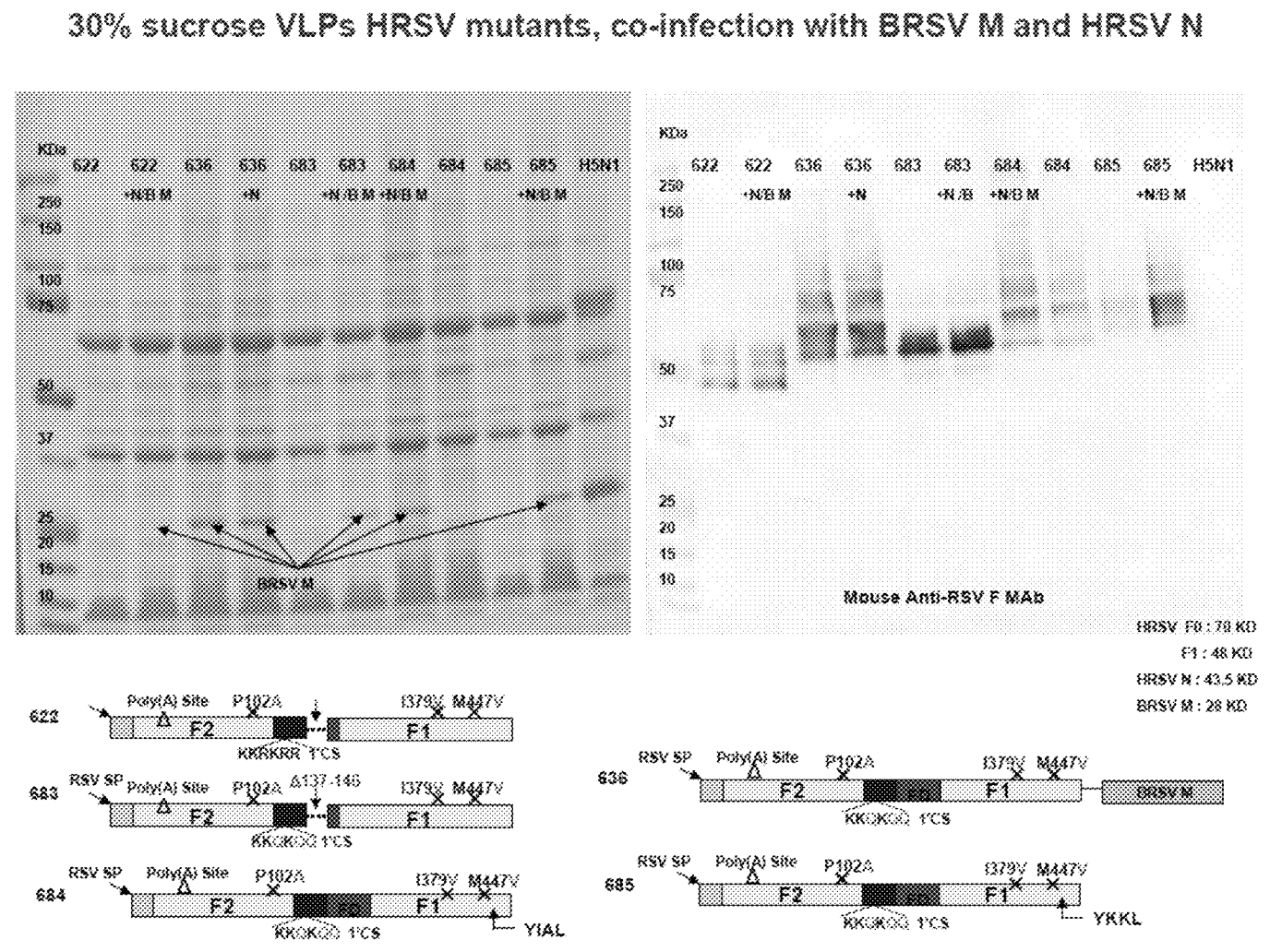
Figure 20:
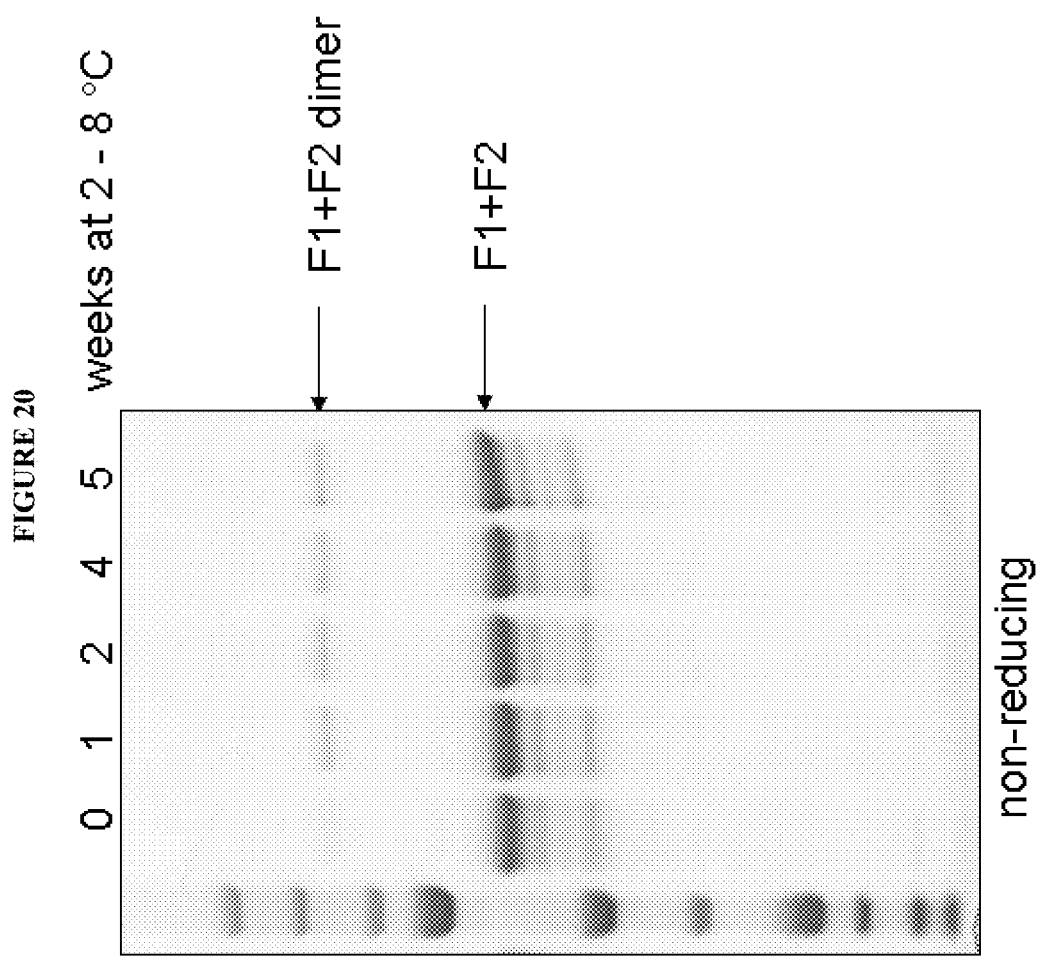
FIG. 20 depicts SDS-PAGE gel stained with coomassie of purified recombinant RSV F protein BV #683 stored at 2-8° C. for 0, 1, 2, 4, and 5 weeks.

In another experiment, modified F protein BV #622, double tandem gene BV #636 (BV #541+BRSV M), BV #683, BV #684 (BV #541 with YIAL L-domain introduced at the C terminus), and BV #685 (BV #541 with YKKL L-domain introduced at the C terminus) were either expressed alone, or co-expressed with HRSV N protein and BRSV M protein. L-domain (Late domain) is conserved sequence in retroviruses, and presents within Gag acting in conjunction with cellular proteins to efficiently release virions from the surface of the cell (Ott et al., 2005, *Journal of Virology* 79: 9038-9045). The structure of each modified F protein is shown in FIG. 14. Both crude cell harvests containing VLPs (intracellular) and VLPs pellets collected from 30% sucrose gradient separation were analyzed by SDS-PAGE stained with coomassie, and Western Blot using anti-RSV F monoclonal antibody. FIG. 14 shows the results of SDS-PAGE and Western Blot analysis of crude cell harvests containing VLPs (intracellular), and FIG. 15 showed results of SDS-PAGE and Western Blot analysis of VLPs pellets collected from 30% sucrose gradient separation. BV #622 and BV #683 were highly expressed by themselves or co-expressed with HRSV N protein and BRSV M protein, while BV #636, BV #684, and BV #685 had poor expression.

Example 9

Screening of Chimeric HRSV F Proteins with High Expression

Efforts were made to screen for additional RSV F proteins that can be highly expressed in soluble form in insect cells and can form VLPs with better yield. Various F genes were designed, expressed, and analyzed. Both Western Blot and SDS-PAGE were used to evaluate the expression.

FIG. 16*a* to FIG. 16*d* summarize the structure, clone name, description, Western Blot/coomassie analysis results, and conclusion for each chimeric HRSV F clone.

As the results indicated, wild type full length F protein was poorly expressed; chimeric HRSV F proteins that contain $F_1$ but not $F_2$ subunit could be expressed well, but the products were either insoluble, which might be due to misfolding, or could not assemble with other viral proteins to form VLPs with good yield after co-infections. Inactivation of the primary cleavage site alone did not result in substantial increases in expression, but better expression was achieved when inactivation of the primary cleavage site was combined with other modification such as deletion of cryptic poly (A) site and correction of GenBank aa errors (e.g., BV #541). Introduction of the YKKL L-domain into the C terminus of BV #541 enhanced the secretion of VLPs containing modified F protein for about 2-3 folds in co-expression with BRSV M and HRSV N proteins. The results further showed that a double tandem chimeric gene consisting of BV #541 gene and BRSV M gene displayed both improved intracellular and VLPs yield compared to co-infection of BV #541 and BRSV M proteins, indicating that BRSV M protein can facilitate production of VLPs containing modified HRSV F protein in insect cells when tandemly expressed. A triple tandem chimeric gene consisting of BV #541, BRSV M, and HRSV N had even higher intracellular and much better VLPs yield compared to above mentioned double tandem chimeric gene or co-infection of BV #541, BRSV M, and HRSV N proteins. Furthermore, the results suggested that chimeric HRSV F protein BV#683 (e.g. F protein 683, SEQ ID NO: 8) had the best intracellular expression. Expression of a double tandem chimeric gene consisting of BV#683 and BRSV M genes, or a triple tandem chimeric gene consisting of BV#683, BRSV M, and HRSV N genes is also embodied herein. These double and triple tandem chimeric gene should further improve VLP production compared to co-infection.

Example 10

RSV Neutralization Assay and RSV Challenge Studies in Mice

To test the efficiency of vaccine comprising modified HRSV F protein BV #683 in prohibiting RSV infection, neutralization assay and RSV challenge studies were conducted in mice. The experimental procedures are shown in FIG. 17.

Groups of mice (n=10) were injected intramuscularly (except for live RSV) with placebo (PBS solution), live RSV (given intranasally), formalin inactivated RSV vaccine (FI-RSV), 1 ug purified F particles (PFP, modified F protein BV #683), 1 ug purified F particles with Alum (PFP+Alum), 10 ug purified F particles, 10 ug purified F particles with Alum (PFP+Alum), or 30 ug purified F particles on day 0 and day 21. Each immunized group was challenged by live RSV on day 42 (21 days after the second immunization). Mouse serum from each group was harvested on day 0, day 31 (10 days after the second immunization), and day 46 (4 days following challenge with live RSV).

Mouse serum from each treatment group was assayed for the presence of anti-RSV neutralization antibodies. Dilutions of serum from immunized mice were incubated with infectious RSV in 96-well microtiter plates. Serum was diluted from 1:20 to 1:2560. 50 ul diluted serum was mixed with 50 ul live RSV virus (400 pfu) in each well. The virus/serum mixture was incubated first for 60 minutes at room temperature, and then mixed with 100 ul HEp-2 cells and incubated for 4 days. The number of infectious virus plaques were then counted after stained with crystal violet. The neutralization titer for each serum sample was defined as the inverse of the highest dilution of serum that produced 100% RSV neutralization (e.g., no plaques) and was determined for each animal. The geometric mean serum neutralizing antibody titer at day 31 (10 days after the boost) and day 46 (4 days following challenge with live RSV) were graphed for each vaccine group. FIG. 18 shows the results of neutralization assays. The results indicate that 10 ug or 30 ug purified F protein produce much higher neutralization titer as compared to live RSV. In addition, neutralization titers of PFP are enhanced with co-administration of Alum adjuvant.

RSV challenge studies were carried out to determine if immunization could prevent and/or inhibit RSV replication in the lungs of the immunized animals. The amount of RSV in the lungs of immunized mice was determined by plaque assay using HEp-2 cells Immunized groups of mice mentioned above were infected with $1\times10^6$ pfu of infectious RSV long strain intranasally on day 42 (11 days after the second immunization). On day 46 (4 days after RSV infection), lungs of mice were removed, weighed, and homogenized. Homogenized lung tissue was clarified. Supernatant of clarified solution was diluted and subjected to plaque assay using HEp-2 cells to determine RSV titer in lung tissue (calculated as pfu/g lung tissue). Results are shown in FIG. 19, indicating that all mice immunized with recombinant RSV F protein BV #683 had undetectable RSV in the lungs, and even 1 ug purified recombinant HRSV F protein BV #683 without adjuvant exhibited excellent efficiency in inhibiting RSV replication (reduced more then 1000 times compared to placebo).

To determine the stability of RSV PFP vaccine used above, the vaccine was stored at 2-8° C. for 0, 1, 2, 4, and 5 weeks, and then analyzed by SDS-PAGE stained with coomassie (FIG. 20). The results show that this RSV PFP vaccine is very stable at 2-8° C. and there is no detectable degradation.

Example 11

Recombinant RSV F Micelle Activity in Cotton Rats

In this example, animals groups included immunization at days 0 and 21 with live RSV (RSV), formalin inactivated RSV (FI-RSV), RSV-F protein BV #683 with and without aluminum (PFP and PFP+Aluminum Adjuvant), and PBS controls.

Figure 21:
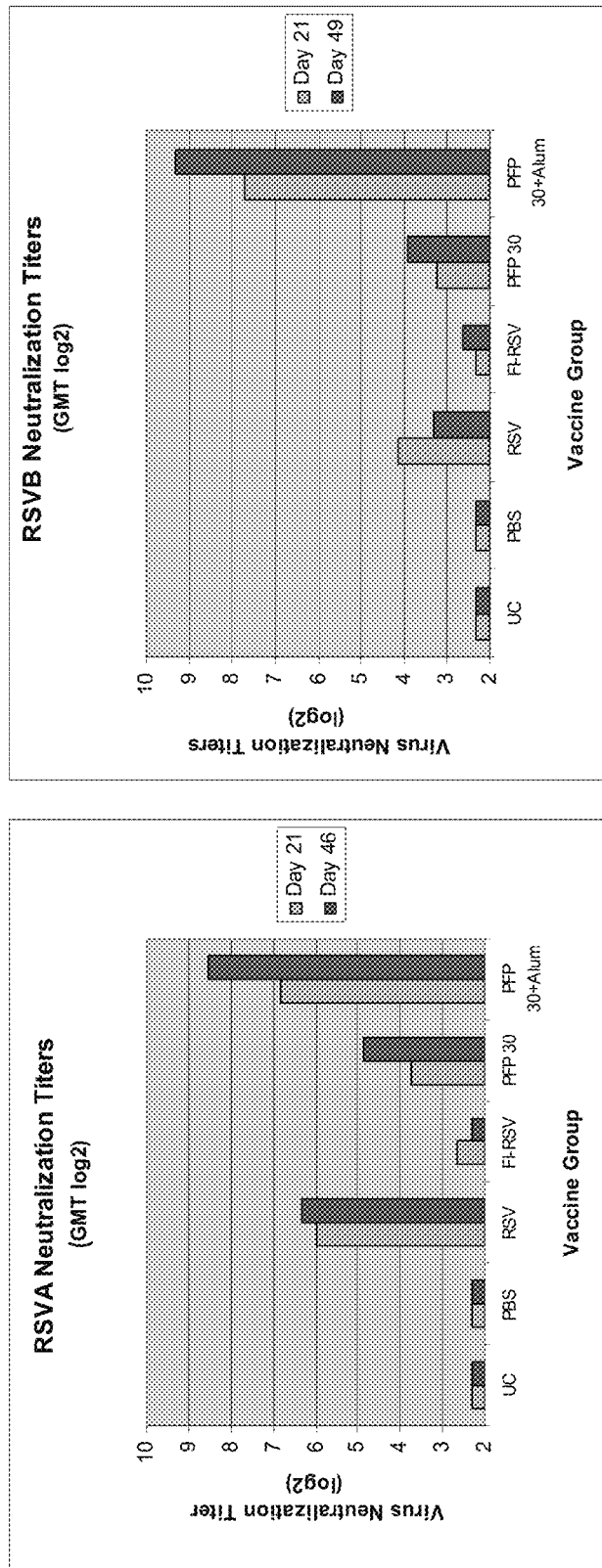
FIG. 21 depicts RSV A and RSV B neutralizing antibody responses following immunization with live RSV (RSV), formalin inactivated RSV (FI-RSV), RSV-F protein BV #683 with and without aluminum (PFP and PFP+Aluminum Adjuvant), and PBS controls.

As shown in FIG. 21, immunization with 30 ug of the F-micelle vaccine (RSV-F protein BV #683, i.e. F protein 683, SEQ ID NO: 8), with and without aluminum produced robust neutralizing antibody responses following exposure to both RSV A and RSV B. In addition, it was observed that aluminum significantly enhances the antibody response. Moreover, neutralizing antibodies were increased following a boost at day 46 or day 49 in RSV A and RSV B, respectively.

Figure 22:
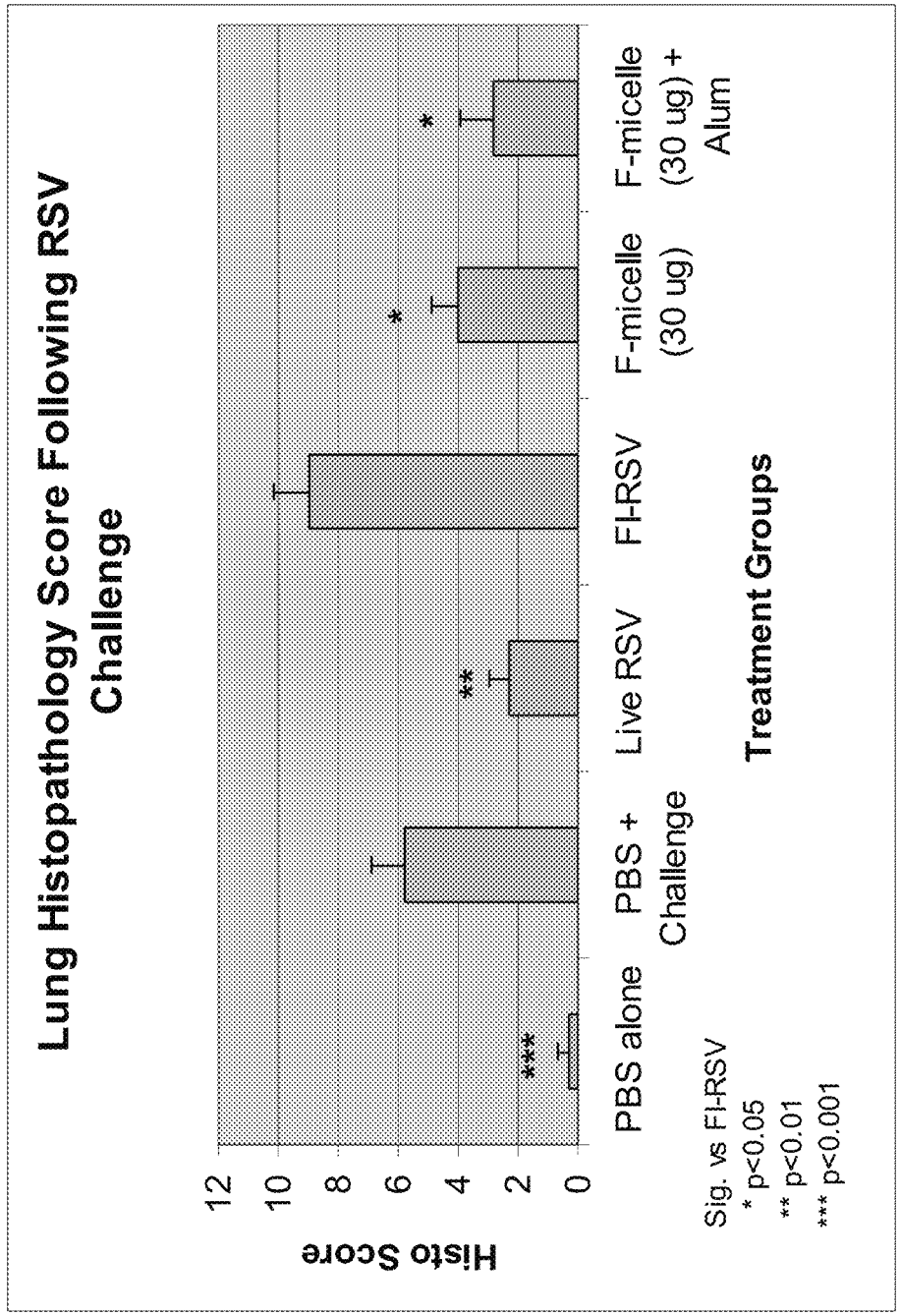
FIG. 22 depicts lung pathology following challenge with RSV in rats immunized with live RSV, formalin inactivated RSV (FI-RSV), RSV-F protein BV #683 with and without aluminum (F-micelle (30 ug) and F-micelle (30 ug)+Aluminum Adjuvant), and PBS controls.

While significant lung pathology was observed in rats immunized with formalin inactivated RSV (FI-RSV), no disease enhancement was seen with the F-micelle vaccine (FIG. 22). The use of the F-micelle vaccine and the F-micelle vaccine with adjuvant produced lower inflammation scores (4.0 and 2.8, respectively) than the primary RSV infection (PBS+RSV challenge) control group (5.8). As noted above, the FI-RSV treated group had a higher inflammation score than the primary RSV infection (PBS+RSV challenge) control group (9.0 versus 5.8). Moreover, the FI-RSV treated group had a significantly higher mean inflammation score (9.0) than the unchallenged placebo controls, live RSV+RSV challenge, F-micelle+RSV challenge, and F-micelle+aluminum+RSV challenge.

The foregoing detailed description has been given for clearness of understanding only and no unnecessary limitations should be understood therefrom as modifications will be obvious to those skilled in the art. It is not an admission that any of the information provided herein is prior art or relevant to the presently claimed inventions, or that any publication specifically or implicitly referenced is prior art.

Unless defined otherwise, all technical and scientific terms used herein have the same meaning as commonly understood by one of ordinary skill in the art to which this invention belongs.

Although the application has been broken into sections to direct the reader's attention to specific embodiments, such sections should be not be construed as a division amongst embodiments. The teachings of each section and the embodiments described therein are applicable to other sections.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The invention claimed is:

1. A method of reducing respiratory syncytial virus (RSV) replication in the lung of an infant or juvenile, said method comprising:
   administering an RSV Fusion (F) protein,
   wherein the RSV F protein is encoded by a nucleic acid having the sequence of SEQ ID NO:7; and
   wherein an immune response that reduces RSV replication in the lung is obtained.

2. The method of claim 1, wherein the administration is intramuscular.

3. The method of claim 2, wherein the immune response comprises neutralizing antibodies.

4. The method of claim 3, wherein the neutralizing antibodies bind a polypeptide corresponding to amino acids 254-278 (SEQ ID NO:35) of the wild-type RSV F protein.

5. The method of claim 2, wherein 1 microgram to 30 micrograms of the RSV F protein is administered.

6. The method of claim 2, wherein 1 microgram to 10 micrograms of the RSV F protein is administered.

7. The method of claim 2, wherein the RSV F protein is administered without an adjuvant.

8. The method of claim 2, wherein the RSV F protein is administered with an adjuvant.

9. The method of claim 8, wherein the adjuvant is alum.

10. The method of claim 2, wherein the RSV F stimulated immune response is associated with reduced incidence of an RSV-induced pathological lung response compared to an immune response obtained by administering a formalin-inactivated RSV (FI-RSV).

11. The method of claim 10, wherein the pathological lung response is selected from the group consisting of bronchiolitis, bronchitis, alveolitis, and pneumonitis.

12. The method of claim 1 further comprising administering one or more additional RSV proteins selected from the group consisting of an RSV M protein, and RSV N protein, and RSV G protein, and an RSV SH protein.

13. The method of claim 1, wherein the RSV F protein consists of the amino acid sequence of SEQ ID NO:8.

14. The method of claim 1, wherein the administration of the RSV F protein is a booster administration after an initial administration of the same antigen.

15. The method of claim 14, wherein the booster administration is administered at about one month to about six months after the initial administration.

16. The method of claim 14, wherein the booster administration is administered at six months after the initial administration.

17. The method of claim 1 wherein the RSV F protein lacks an N-terminal signal peptide.

18. The method of claim 1 wherein the RSV F protein is purified from an Sf9 insect host cell.

* * * * *

SEQUENCE LISTING

```
<160> NUMBER OF SEQ ID NOS: 35

<210> SEQ ID NO 1
<211> LENGTH: 1725
<212> TYPE: DNA
<213> ORGANISM: Respiratory syncytial virus

<400> SEQUENCE: 1
atggagttgc taatcctcaa agcaaatgca attaccacaa tcctcactgc agtcacattt     60
tgttttgctt ctggtcaaaa catcactgaa gaattttatc aatcaacatg cagtgcagtt    120
agcaaaggct atcttagtgc tctgagaact ggttggtata ccagtgttat aactatagaa    180
ttaagtaata tcaaggaaaa taagtgtaat ggaacagatg ctaaggtaaa attgataaaa    240
caagaattag ataaatataa aaatgctgta acagaattgc agttgctcat gcaaagcaca    300
ccaccaacaa acaatcgagc cagaagagaa ctaccaaggt ttatgaatta tacactcaac    360
aatgccaaaa aaaccaatgt aacattaagc aagaaaagga aaagaagatt tcttggtttt    420
ttgttaggtg ttggatctgc aatcgccagt ggcgttgctg tatctaaggt cctgcaccta    480
gaaggggaag tgaacaagat caaaagtgct ctactatcca caaacaaggc tgtagtcagc    540
ttatcaaatg gagttagtgt cttaaccagc aaagtgttag acctcaaaaa ctatatagat    600
aaacaattgt tacctattgt gaacaagcaa agctgcagca tatcaaatat agaaactgtg    660
atagagttcc aacaaaagaa caacagacta ctagagatta ccagggaatt tagtgttaat    720
gcaggtgtaa ctacacctgt aagcacttac atgttaacta atagtgaatt attgtcatta    780
atcaatgata tgcctataac aaatgatcag aaaaagttaa tgtccaacaa tgttcaaata    840
```

```
gttagacagc aaagttactc tatcatgtcc ataataaaag aggaagtctt agcatatgta    900
gtacaattac cactatatgg tgttatagat acaccctgtt ggaaactaca cacatcccct    960
ctatgtacaa ccaacacaaa agaagggtcc aacatctgtt aacaagaac tgacagagga   1020 tggtactgtg acaatgcagg atcagtatct ttcttcccac aagctgaaac atgtaaagtt   1080
caatcaaatc gagtattttg tgacacaatg aacagtttaa cattaccaag tgaaataaat   1140
ctctgcaatg ttgacatatt caaccccaaa tatgattgta aaattatgac ttcaaaaaca   1200
gatgtaagca gctccgttat cacatctcta ggagccattg tgtcatgcta tggcaaaact   1260
aaatgtacag catccaataa aaatcgtgga atcataaaga catttctaa cgggtgcgat   1320 tatgtatcaa ataaagggat ggacactgtg tctgtaggta acacattata ttatgtaaat   1380
aagcaagaag gtaaaagtct ctatgtaaaa ggtgaaccaa taataaattt ctatgacccca  1440 ttagtattcc cctctgatga atttgatgca tcaatatctc aagtcaacga gaagattaac   1500
cagagcctag catttattcg taaatccgat gaattattac ataatgtaaa tgctggtaaa   1560
tccaccacaa atatcatgat aactactata attatagtga ttatagtaat attgttatca   1620
ttaattgctg ttggactgct cttatactgt aaggccagaa gcacaccagt cacactaagc   1680
aaagatcaac tgagtggtat aaataatatt gcatttagta actaa                  1725

<210> SEQ ID NO 2
<211> LENGTH: 574
<212> TYPE: PRT
<213> ORGANISM: Respiratory syncytial virus

<400> SEQUENCE: 2

Met Glu Leu Le

```
Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Ile Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
            435                 440                 445

Thr Val Ser Val Gly Asn Thr Leu Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 3
<211> LENGTH: 1725
<212> TYPE: DNA
<213> ORGANISM: Artificial Sequence
<220> FEATURE:
<223> OTHER INFORMATION: F Protein 576

<400> SEQUENCE: 3
atggagctgc tcatcttgaa ggctaacgcc attaccacta tccttacagc ggtgacgttc    60
```

| | |
|---|---|
| tgctttgcat ccggtcagaa tattaccgaa gagttctacc aatctacttg tagcgctgtc | 120 |
| tcaaaaggct atctgtcggc cctccgtaca ggatggtaca cgagtgttat caccatcgaa | 180 |
| ttgtccaaca ttaaggagaa caagtgcaac ggtactgacg cgaaggtaaa gcttatcaaa | 240 |
| caggaactgg ataagtacaa gaacgcagtg acagagctcc aattgctgat gcagtctacc | 300 |
| cccgctacga ataaccgcgc taggagagaa cttccacgat tcatgaacta tactctcaat | 360 |
| aacgccaaaa agaccaacgt cacattgagc aaaaagcgta agcgcaggtt tctgggcttc | 420 |
| ctcctgggag ttggttcagc tattgcgtcg ggcgtagccg tgagtaaagt ccttcacttg | 480 |
| gagggagaag ttaataagat caagtccgca ctcctgtcta ctaacaaagc tgtggtcagc | 540 |
| ttgtcaaacg gtgtatccgt gctgacctcg aaggttcttg acctcaaaaa ttacatcgat | 600 |
| aagcaattgc tgccgattgt caacaagcag agttgttcta tcagcaatat tgagacggtg | 660 |
| atcgagttcc aacagaaaaa caacagactc ctggaaatca cacgtgagtt ttcagtaaat | 720 |
| gccggcgtta ctaccccgt ctccacgtac atgcttacaa actcggaatt gctcagtctg | 780 |
| attaacgaca tgcctatcac taatgatcag aagaagctta tgtctaacaa cgtgcaaatt | 840 |
| gtccgccagc aaagctattc catcatgtca atcattaaag aggaagtgtt ggcgtacgta | 900 |
| gttcagctcc cactgtacgg agtcatcgac accccgtgct ggaagcttca tacctcgccc | 960 |
| ttgtgtacga caaatactaa agagggttct aacatttgcc tcaccaggac ggatcgaggc | 1020 |
| tggtattgcg ataacgctgg aagtgtgagc ttcttccctc aagcagaaac atgtaaggta | 1080 |
| cagtccaata gagttttttg cgacactatg aactcactga cccttccatc tgaggtcaat | 1140 |
| ttgtgtaacg tcgatatctt caacccgaag tacgactgca aaattatgac gtccaagaca | 1200 |
| gatgtgtcga gtagcgtaat cacttcactc ggtgccatcg tttcttgcta cggcaagacc | 1260 |
| aaatgtacgg cttccaataa gaaccgtgga attatcaaaa cattctcgaa cggttgcgac | 1320 |
| tatgtcagca ataagggcgt ggacactgtg agtgtaggaa acaccctgta ctacgttaac | 1380 |
| aagcaagaag gtaaatcact gtatgtcaag ggcgagccca ttatcaattt ttacgatcct | 1440 |
| cttgtgttcc catccgacga gttcgatgcg tctatcagcc aggtaaacga aaagattaac | 1500 |
| cagtccttgg catttatccg caaatcggac gagctcctgc acaatgttaa cgccggaaag | 1560 |
| agtacgacaa acattatgat cactaccatc attatcgtca ttatcgtgat ccttttgtca | 1620 |
| ctcattgctg taggtctgct tttgtactgt aaagcgaggt ctacgcccgt tacactcagc | 1680 |
| aaggatcaac tgtccggcat caataacatt gccttctcga attaa | 1725 |

<210> SEQ ID NO 4
<211> LENGTH: 574
<212> TYPE: PRT
<213> ORGANISM: Artificial Sequence
<220> FEATURE:
<223> OTHER INFORMATION: F Protein 576

<400> SEQUENCE: 4

Met Glu Leu Leu Ile Leu Lys Ala Asn Ala Ile Thr Thr Ile Leu Thr
1               5                   10                  15

Ala Val Thr Phe Cys Phe Ala Ser Gly

```
            65                  70                  75                  80
        Gln Glu Leu Asp Lys Tyr Lys Asn Ala Val Thr Glu Leu Gln Leu Leu
                        85                  90                  95

Met Gln Ser Thr Pro Ala Thr Asn Asn Arg Ala Arg Arg Glu Leu Pro
                    100                 105                 110

Arg Phe Met Asn Tyr Thr Leu Asn Asn Ala Lys Lys Thr Asn Val Thr
                115                 120                 125

Leu Ser Lys Lys Arg Lys Arg Arg Phe Leu Gly Phe Leu Leu Gly Val
                130                 135                 140

Gly Ser Ala Ile Ala Ser Gly Val Ala Val Ser Lys Val Leu His Leu
        145                 150                 155                 160

Glu Gly Glu Val Asn Lys Ile Lys Ser Ala Leu Leu Ser Thr Asn Lys
                        165                 170                 175

Ala Val Val Ser Leu Ser Asn Gly Val Ser Val Leu Thr Ser Lys Val
                    180                 185                 190

Leu Asp Leu Lys Asn Tyr Ile Asp Lys Gln Leu Leu Pro Ile Val Asn
                195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
        225                 230                 235                 240

Ala Gly Val Thr Thr Pro Val Ser Thr Tyr Met Leu Thr Asn Ser Glu
                        245                 250                 255

Leu Leu Ser Leu Ile Asn Asp Met Pro Ile Thr Asn Asp Gln Lys Lys
                    260                 265                 270

Leu Met Ser Asn Asn Val Gln Ile Val Arg Gln Gln Ser Tyr Ser Ile
                275                 280                 285

Met Ser Ile Ile Lys Glu Glu Val Leu Ala Tyr Val Val Gln Leu Pro
            290                 295                 300

Leu Tyr Gly Val Ile Asp Thr Pro Cys Trp Lys Leu His Thr Ser Pro
        305                 310                 315                 320

Leu Cys Thr Thr Asn Thr Lys Glu Gly Ser Asn Ile Cys Leu Thr Arg
                        325                 330                 335

Thr Asp Arg Gly Trp Tyr Cys Asp Asn Ala Gly Ser Val Ser Phe Phe
                    340                 345                 350

Pro Gln Ala Glu Thr Cys Lys Val Gln Ser Asn Arg Val Phe Cys Asp
                355                 360                 365

Thr Met Asn Ser Leu Thr Leu Pro Ser Glu Val Asn Leu Cys Asn Val
            370                 375                 380

Asp Ile Phe Asn Pro Lys Tyr Asp Cys Lys Ile Met Thr Ser Lys Thr
        385                 390                 395                 400

Asp Val Ser Ser Ser Val Ile Thr Ser Leu Gly Ala Ile Val Ser Cys
                        405                 410                 415

Tyr Gly Lys Thr Lys Cys Thr Ala Ser Asn Lys Asn Arg Gly Ile Ile
                    420                 425                 430

Lys Thr Phe Ser Asn Gly Cys Asp Tyr Val Ser Asn Lys Gly Val Asp
                435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
        465                 470                 475                 480

Leu Val Phe Pro Ser Asp Glu Phe Asp Ala Ser Ile Ser Gln Val Asn
                        485                 490                 495
```

```
Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 5
<211> LENGTH: 1725
<212> TYPE: DNA
<213> ORGANISM: Artificial Sequence
<220> FEATURE:
<223> OTHER INFORMATION: F Protein 541

<400> SEQUENCE: 5

```
atggagctgc tcatcttgaa ggctaacgcc attaccacta tccttacagc ggtgacgttc      60
tgctttgcat ccggtcagaa tattaccgaa gagttctacc aatctacttg tagcgctgtc     120
tcaaaaggct atctgtcggc cctccgtaca ggatggtaca cgagtgttat caccatcgaa     180
ttgtccaaca ttaaggagaa caagtgcaac ggtactgacg cgaaggtaaa gcttatcaaa     240
caggaactgg ataagtacaa gaacgcagtg acagagctcc aattgctgat gcagtctacc     300
cccgctacga ataaccgcgc taggagagaa cttccacgat tcatgaacta tactctcaat     360
aacgccaaaa agaccaacgt cacattgagc aaaaagcaga gcaacagtt  tctgggcttc     420
ctcctgggag ttggttcagc tattgcgtcg ggcgtagccg tgagtaaagt ccttcacttg     480
gagggagaag ttaataagat caagtccgca ctcctgtcta ctaacaaagc tgtggtcagc     540
ttgtcaaacg gtgtatccgt gctgacctcg aaggttcttg acctcaaaaa ttacatcgat     600
aagcaattgc tgccgattgt caacaagcag agttgttcta tcagcaatat tgagacggtg     660
atcgagttcc aacagaaaaa caacagactc ctggaaatca cacgtgagtt ttcagtaaat     720
gccggcgtta ctaccccccgt ctccacgtac atgcttacaa actcggaatt gctcagtctg     780
attaacgaca tgcctatcac taatgatcag aagaagctta tgtctaacaa cgtgcaaatt     840
gtccgccagc aaagctattc catcatgtca atcattaaag aggaagtgtt ggcgtacgta     900
gttcagctcc cactgtacgg agtcatcgac accccgtgct ggaagcttca tacctcgccc     960
ttgtgtacga caaatactaa agagggttct aacatttgcc tcaccaggac ggatcgaggc    1020
tggtattgcg ataacgctgg aagtgtgagc ttcttccctc aagcagaaac atgtaaggta    1080
cagtccaata gagttttttg cgacactatg aactcactga cccttccatc tgaggtcaat    1140
ttgtgtaacg tcgatatctt caacccgaag tacgactgca aaattatgac gtccaagaca    1200
gatgtgtcga gtagcgtaat cacttcactc ggtgccatcg tttcttgcta cggcaagacc    1260
aaatgtacgg cttccaataa gaaccgtgga attatcaaaa cattctcgaa cggttgcgac    1320
tatgtcagca ataagggcgt ggacactgtg agtgtaggaa acaccctgta ctacgttaac    1380
aagcaagaag gtaaatcact gtatgtcaag ggcgagccca ttatcaattt ttacgatcct    1440
cttgtgttcc catccgacga gttcgatgcg tctatcagcc aggtaaacga aaagattaac    1500
cagtccttgg catttatccg caatcggac gagctcctgc acaatgttaa cgccggaaag    1560
agtacgacaa acattatgat cactaccatc attatcgtca ttatcgtgat cctttttgtca    1620
```
ctcattgctg taggtctgct tttgtactgt aaagcgaggt ctacgcccgt tacactcagc    1680
aaggatcaac tgtccggcat caataacatt gccttctcga attaa    1725

<210> SEQ ID NO 6
<211> LENGTH: 574
<212> TYPE: PRT
<213> ORGANISM: Artificial Sequence
<220> FEATURE:
<223> OTHER INFORMATION: F protein 541

<400> SEQUENCE: 6

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
```

```
                340             345             350
Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
        370                 375                 380

Asp Ile Phe Asn Pro Lys Tyr Asp Cys Lys Ile Met Thr Ser Lys Thr
385                 390                 395                 400

Asp Val Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
        450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
        530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 7  
<211> LENGTH: 1695  
<212> TYPE: DNA  
<213> ORGANISM: Artificial Sequence  
<220> FEATURE:  
<223> OTHER INFORMATION: F Protein 683

<400> SEQUENCE: 7

```
atggagctgc tcatcttgaa ggctaacgcc attaccacta tccttacagc ggtgacgttc      60
tgctttgcat ccggtcagaa tattaccgaa gagttctacc aatctacttg tagcgctgtc     120
tcaaaaggct atctgtcggc cctccgtaca ggatggtaca cgagtgttat caccatcgaa     180
ttgtccaaca ttaaggagaa caagtgcaac ggtactgacg cgaaggtaaa gcttatcaaa     240
caggaactgg ataagtacaa gaacgcagtg acagagctcc aattgctgat gcagtctacc     300
cccgctacga ataaccgcgc taggagagaa cttccacgat tcatgaacta tactctcaat     360
aacgccaaaa agaccaacgt cacattgagc aaaaagcaga agcaacaggc tattgcgtcg     420
ggcgtagccg tgagtaaagt ccttcacttg gagggagaag ttaataagat caagtccgca     480
ctcctgtcta ctaacaaagc tgtggtcagc ttgtcaaacg gtgtatccgt gctgacctcg     540
aaggttcttg acctcaaaaa ttacatcgat aagcaattgc tgccgattgt caacaagcag     600
agttgttcta tcagcaatat tgagacggtg atcgagttcc aacagaaaaa caacagactc     660
ctggaaatca cacgtgagtt ttcagtaaat gccggcgtta ctaccccgt ctccacgtac     720 atgcttacaa actcggaatt gctcagtctg attaacgaca tgcctatcac taatgatcag     780
```

| | |
|---|---|
| aagaagctta tgtctaacaa cgtgcaaatt gtccgccagc aaagctattc catcatgtca | 840 |
| atcattaaag aggaagtgtt ggcgtacgta gttcagctcc cactgtacgg agtcatcgac | 900 |
| accccgtgct ggaagcttca tacctcgccc ttgtgtacga caaatactaa agagggttct | 960 |
| aacatttgcc tcaccaggac ggatcgaggc tggtattgcg ataacgctgg aagtgtgagc | 1020 |
| ttcttccctc aagcagaaac atgtaaggta cagtccaata gagttttttg cgacactatg | 1080 |
| aactcactga cccttccatc tgaggtcaat tgtgtaacg tcgatatctt caaccccgaag | 1140 |
| tacgactgca aaattatgac gtccaagaca gatgtgtcga gtagcgtaat cacttcactc | 1200 |
| ggtgccatcg tttcttgcta cggcaagacc aaatgtacgg cttccaataa gaaccgtgga | 1260 |
| attatcaaaa cattctcgaa cggttgcgac tatgtcagca ataagggcgt ggacactgtg | 1320 |
| agtgtaggaa acaccctgta ctacgttaac aagcaagaag gtaaatcact gtatgtcaag | 1380 |
| ggcgagccca ttatcaattt ttacgatcct cttgtgttcc catccgacga gttcgatgcg | 1440 |
| tctatcagcc aggtaaacga aaagattaac cagtccttgg catttatccg caaatcggac | 1500 |
| gagctcctgc acaatgttaa cgccggaaag agtacgacaa acattatgat cactaccatc | 1560 |
| attatcgtca ttatcgtgat cctttttgtca ctcattgctg taggtctgct tttgtactgt | 1620 |
| aaagcgaggt ctacgcccgt tacactcagc aaggatcaac tgtccggcat caataacatt | 1680 |
| gccttctcga attaa | 1695 |

<210> SEQ ID NO 8
<211> LENGTH: 564
<212> TYPE: PRT
<213> ORGANISM: Artificial Sequence
<220> FEATURE:
<223> OTHER INFORMATION: F protein 683

<400> SEQUENCE: 8

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Gln Lys Gln Gln Ala Ile Ala Ser Gly Val Ala Val
    130                 135                 140

Ser Lys Val Leu His Leu Glu Gly Glu Val Asn Lys Ile Lys Ser Ala
145                 150                 155                 160

Leu Leu Ser Thr Asn Lys Ala Val Val Ser Leu Ser Asn Gly Val Ser
                165                 170                 175

Val Leu Thr Ser Lys Val Leu Asp Leu Lys Asn Tyr Ile Asp Lys Gln
            180                 185                 190
```

```
Leu Leu Pro Ile Val Asn Lys Gln Ser Cys Ser Ile Ser Asn Ile Glu
            195                 200                 205

Thr Val Ile Glu Phe Gln Gln Lys Asn Arg Leu Leu Glu Ile Thr
210                 215                 220

Arg Glu Phe Ser Val Asn Ala Gly Val Thr Thr Pro Val Ser Thr Tyr
225                 230                 235                 240

Met Leu Thr Asn Ser Glu Leu Leu Ser Leu Ile Asn Asp Met Pro Ile
            245                 250                 255

Thr Asn Asp Gln Lys Lys Leu Met Ser Asn Asn Val Gln Ile Val Arg
            260                 265                 270

Gln Gln Ser Tyr Ser Ile Met Ser Ile Ile Lys Glu Glu Val Leu Ala
            275                 280                 285

Tyr Val Val Gln Leu Pro Leu Tyr Gly Val Ile Asp Thr Pro Cys Trp
290                 295                 300

Lys Leu His Thr Ser Pro Leu Cys Thr Thr Asn Thr Lys Glu Gly Ser
305                 310                 315                 320

Asn Ile Cys Leu Thr Arg Thr Asp Arg Gly Trp Tyr Cys Asp Asn Ala
                325                 330                 335

Gly Ser Val Ser Phe Phe Pro Gln Ala Glu Thr Cys Lys Val Gln Ser
            340                 345                 350

Asn Arg Val Phe Cys Asp Thr Met Asn Ser Leu Thr Leu Pro Ser Glu
            355                 360                 365

Val Asn Leu Cys Asn Val Asp Ile Phe Asn Pro Lys Tyr Asp Cys Lys
370                 375                 380

Ile Met Thr Ser Lys Thr Asp Val Ser Ser Val Ile Thr Ser Leu
385                 390                 395                 400

Gly Ala Ile Val Ser Cys Tyr Gly Lys Thr Lys Cys Thr Ala Ser Asn
                405                 410                 415

Lys Asn Arg Gly Ile Ile Lys Thr Phe Ser Asn Gly Cys Asp Tyr Val
            420                 425                 430

Ser Asn Lys Gly Val Asp Thr Val Ser Val Gly Asn Thr Leu Tyr Tyr
            435                 440                 445

Val Asn Lys Gln Glu Gly Lys Ser Leu Tyr Val Lys Gly Glu Pro Ile
450                 455                 460

Ile Asn Phe Tyr Asp Pro Leu Val Phe Pro Ser Asp Glu Phe Asp Ala
465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
            500                 505                 510

Thr Asn Ile Met Ile Thr Thr Ile Ile Val Ile Ile Val Ile Leu
            515                 520                 525

Leu Ser Leu Ile Ala Val Gly Leu Leu Leu Tyr Cys Lys Ala Arg Ser
530                 535                 540

Thr Pro Val Thr Leu Ser Lys Asp Gln Leu Ser Gly Ile Asn Asn Ile
545                 550                 555                 560

Ala Phe Ser Asn

<210> SEQ ID NO 9
<211> LENGTH: 1695
<212> TYPE: DNA
<213> ORGANISM: Artificial Sequence
<220> FEATURE:
<223> OTHER INFORMATION: F protein 622
```

<400> SEQUENCE: 9

```
atggagctgc tcatcttgaa ggctaacgcc attaccacta tccttacagc ggtgacgttc    60
tgctttgcat ccggtcagaa tattaccgaa gagttctacc aatctacttg tagcgctgtc   120
tcaaaaggct atctgtcggc cctccgtaca ggatggtaca cgagtgttat caccatcgaa   180
ttgtccaaca ttaaggagaa caagtgcaac ggtactgacg cgaaggtaaa gcttatcaaa   240
caggaactgg ataagtacaa gaacgcagtg acagagctcc aattgctgat gcagtctacc   300
cccgctacga ataaccgcgc taggagagaa cttccacgat tcatgaacta tactctcaat   360
aacgccaaaa agaccaacgt cacattgagc aaaaagcgta agcgcagggc tattgcgtcg   420
ggcgtagccg tgagtaaagt ccttcacttg gagggagaag ttaataagat caagtccgca   480
ctcctgtcta ctaacaaagc tgtggtcagc ttgtcaaacg gtgtatccgt gctgacctcg   540
aaggttcttg acctcaaaaa tcacatcgat aagcaattgc tgccgattgt caacaagcag   600
agttgttcta tcagcaatat tgagacggtg atcgagttcc aacagaaaaa caacagactc   660
ctggaaatca cacgtgagtt ttcagtaaat gccggcgtta ctaccccgt ctccacgtac    720
atgcttacaa actcggaatt gctcagtctg attaacgaca tgcctatcac taatgatcag   780
aagaagctta tgtctaacaa cgtgcaaatt gtccgccagc aaagctattc catcatgtca   840
atcattaaag aggaagtgtt ggcgtacgta gttcagctcc cactgtacgg agtcatcgac   900
accccgtgct ggaagcttca tacctcgccc ttgtgtacga caaatactaa agagggttct   960
aacatttgcc tcaccaggac ggatcgaggc tggtattgcg ataacgctgg aagtgtgagc  1020
ttcttccctc aagcagaaac atgtaaggta cagtccaata gagttttttg cgacactatg  1080
aactcactga cccttccatc tgaggtcaat ttgtgtaacg tcgatatctt caacccgaag  1140
tacgactgca aaattatgac gtccaagaca gatgtgtcga gtagcgtaat cacttcactc  1200
ggtgccatcg tttcttgcta cggcaagacc aaatgtacgg cttccaataa gaaccgtgga  1260
attatcaaaa cattctcgaa cggttgcgac tatgtcagca ataagggcgt ggacactgtg  1320
agtgtaggaa acaccctgta ctacgttaac aagcaagaag gtaaatcact gtatgtcaag  1380
ggcgagccca ttatcaattt ttacgatcct cttgtgttcc catccgacga gttcgatgcg  1440
tctatcagcc aggtaaacga aaagattaac cagtccttgg catttatccg caaatcggac  1500
gagctcctgc acaatgttaa cgccggaaag agtacgacaa acattatgat cactaccatc  1560
attatcgtca ttatcgtgat ccttttgtca ctcattgctg taggtctgct tttgtactgt  1620
aaagcgaggt ctacgcccgt tacactcagc aaggatcaac tgtccggcat caataacatt  1680
gccttctcga attaa                                                  1695
```

<210> SEQ ID NO 10
<211> LENGTH: 564
<212> TYPE: PRT
<213> ORGANISM: Artificial Sequence
<220> FEATURE:
<223> OTHER INFORMATION: F protein 622

<400> SEQUENCE: 10

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45
```

```
Arg Thr Gly Trp Tyr Thr Ser Val Ile Thr Ile Glu Leu Ser Asn Ile
    50              55              60

Lys Glu Asn Lys Cys Asn Gly Thr Asp Ala Lys Val Lys Leu Ile Lys
 65              70              75              80

Gln Glu Leu Asp Lys Tyr Lys Asn Ala Val Thr Glu Leu Gln Leu Leu
                85              90              95

Met Gln Ser Thr Pro Ala Thr Asn Asn Arg Ala Arg Arg Glu Leu Pro
            100             105             110

Arg Phe Met Asn Tyr Thr Leu Asn Asn Ala Lys Lys Thr Asn Val Thr
        115             120             125

Leu Ser Lys Lys Arg Lys Arg Arg Ala Ile Ala Ser Gly Val Ala Val
130             135             140

Ser Lys Val Leu His Leu Glu Gly Glu Val Asn Lys Ile Lys Ser Ala
145             150             155             160

Leu Leu Ser Thr Asn Lys Ala Val Val Ser Leu Ser Asn Gly Val Ser
                165             170             175

Val Leu Thr Ser Lys Val Leu Asp Leu Lys Asn His Ile Asp Lys Gln
            180             185             190

Leu Leu Pro Ile Val Asn Lys Gln Ser Cys Ser Ile Ser Asn Ile Glu
        195             200             205

Thr Val Ile Glu Phe Gln Gln Lys Asn Asn Arg Leu Leu Glu Ile Thr
210             215             220

Arg Glu Phe Ser Val Asn Ala Gly Val Thr Thr Pro Val Ser Thr Tyr
225             230             235             240

Met Leu Thr Asn Ser Glu Leu Leu Ser Leu Ile Asn Asp Met Pro Ile
                245             250             255

Thr Asn Asp Gln Lys Lys Leu Met Ser Asn Asn Val Gln Ile Val Arg
            260             265             270

Gln Gln Ser Tyr Ser Ile Met Ser Ile Ile Lys Glu Glu Val Leu Ala
        275             280             285

Tyr Val Val Gln Leu Pro Leu Tyr Gly Val Ile Asp Thr Pro Cys Trp
290             295             300

Lys Leu His Thr Ser Pro Leu Cys Thr Thr Asn Thr Lys Glu Gly Ser
305             310             315             320

Asn Ile Cys Leu Thr Arg Thr Asp Arg Gly Trp Tyr Cys Asp Asn Ala
                325             330             335

Gly Ser Val Ser Phe Phe Pro Gln Ala Glu Thr Cys Lys Val Gln Ser
            340             345             350

Asn Arg Val Phe Cys Asp Thr Met Asn Ser Leu Thr Leu Pro Ser Glu
        355             360             365

Val Asn Leu Cys Asn Val Asp Ile Phe Asn Pro Lys Tyr Asp Cys Lys
370             375             380

Ile Met Thr Ser Lys Thr Asp Val Ser Ser Ser Val Ile Thr Ser Leu
385             390             395             400

Gly Ala Ile Val Ser Cys Tyr Gly Lys Thr Lys Cys Thr Ala Ser Asn
                405             410             415

Lys Asn Arg Gly Ile Ile Lys Thr Phe Ser Asn Gly Cys Asp Tyr Val
            420             425             430

Ser Asn Lys Gly Val Asp Thr Val Ser Val Gly Asn Thr Leu Tyr Tyr
        435             440             445

Val Asn Lys Gln Glu Gly Lys Ser Leu Tyr Val Lys Gly Glu Pro Ile
450             455             460

Ile Asn Phe Tyr Asp Pro Leu Val Phe Pro Ser Asp Glu Phe Asp Ala
```

```
                    465                 470                 475                 480

Ser Ile Ser Gln Val Asn Glu Lys Ile Asn Gln Ser Leu Ala Phe Ile
                485                 490                 495

Arg Lys Ser Asp Glu Leu Leu His Asn Val Asn Ala Gly Lys Ser Thr
                500                 505                 510

Thr Asn Ile Met Ile Thr Thr Ile Ile Val Ile Ile Val Ile Leu
                515                 520                 525

Leu Ser Leu Ile Ala Val Gly Leu Leu Leu Tyr Cys Lys Ala Arg Ser
        530                 535                 540

Thr Pro Val Thr Leu Ser Lys Asp Gln Leu Ser Gly Ile Asn Asn Ile
545                 550                 555                 560

Ala Phe Ser Asn

<210> SEQ ID NO 11
<211> LENGTH: 771
<212> TYPE: DNA
<213> ORGANISM: Bovine respiratory syncytial virus

<400> SEQUENCE: 11
atggagacat acgtgaacaa actccatgaa ggatcaactt acacagctgc tgttcagtac      60
aatgtcatag aaaagatga tgatcctgca tctctcacaa tatgggttcc tatgttccaa     120
tcatccatct ctgctgattt gcttataaaa gaactaatca atgtgaacat attagttcga     180
caaatttcta ctctgaaagg tccttcattg aagattatga taaactcaag aagtgctgta     240
ctagcccaaa tgcccagcaa atttaccata agtgcaaatg tatcattgga tgaacgaagc     300
aaattagcat atgacataac tactccttgt gaaattaagg cttgtagttt aacatgttta     360
aaggtgaaaa atatgctcac aactgtgaaa gatctcacca tgaaaacatt caatcctacc     420
catgagatca ttgcactgtg tgaatttgaa aatatcatga catccaaaag agttgttata     480
ccaactttct taaggtcaat caatgtaaaa gcaaaggatt tggactcact agagaatata     540
gctaccacag agttcaaaaa tgccatcact aatgctaaaa ttatacctta tgctgggttg     600
gtattagtta tcactgtaac tgacaataaa ggggcattca gtacattaa accacaaagt     660 caatttatag tagatcttgg tgcatatcta gagaaagaga gcatatatta tgtaactaca     720
aattggaaac acacggccac taaattctcc attaagccta tagaggactg a              771

<210> SEQ ID NO 12
<211> LENGTH: 256
<212> TYPE: PRT
<213> ORGANISM: Bovine respiratory syncytial virus

<400> SEQUENCE: 12

Met Glu Thr Tyr Val Asn Lys Leu His Glu Gly Ser Thr Tyr Thr Ala
1               5                   10                  15

Ala Val Gln Tyr Asn Val Ile Glu Lys Asp Asp Asp Pro Ala Ser Leu
                20                  25                  30

Thr Ile Trp Val Pro Met Phe Gln Ser Ser Ile Ser Ala Asp Leu Leu
            35                  40                  45

Ile Lys Glu Leu Ile Asn Val Asn Ile Leu Val Arg Gln Ile Ser Thr
        50                  55                  60

Leu Lys Gly Pro Ser Leu Lys Ile Met Ile Asn Ser Arg Ser Ala Val
65                  70                  75                  80

Leu Ala Gln Met Pro Ser Lys Phe Thr Ile Ser Ala Asn Val Ser Leu
                85                  90                  95
```

Asp Glu Arg Ser Lys Leu Ala Tyr Asp Ile Thr Thr Pro Cys Glu Ile
            100                 105                 110

Lys Ala Cys Ser Leu Thr Cys Leu Lys Val Lys Asn Met Leu Thr Thr
        115                 120                 125

Val Lys Asp Leu Thr Met Lys Thr Phe Asn Pro Thr His Glu Ile Ile
    130                 135                 140

Ala Leu Cys Glu Phe Glu Asn Ile Met Thr Ser Lys Arg Val Val Ile
145                 150                 155                 160

Pro Thr Phe Leu Arg Ser Ile Asn Val Lys Ala Lys Asp Leu Asp Ser
                165                 170                 175

Leu Glu Asn Ile Ala Thr Thr Glu Phe Lys Asn Ala Ile Thr Asn Ala
            180                 185                 190

Lys Ile Ile Pro Tyr Ala Gly Leu Val Leu Val Ile Thr Val Thr Asp
        195                 200                 205

Asn Lys Gly Ala Phe Lys Tyr Ile Lys Pro Gln Ser Gln Phe Ile Val
    210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Lys Phe Ser Ile Lys Pro Ile Glu Asp
                245                 250                 255

<210> SEQ ID NO 13
<211> LENGTH: 771
<212> TYPE: DNA
<213> ORGANISM: Artificial Sequence
<220> FEATURE:
<223> OTHER INFORMATION: Codon Optimized Bovine RSV M

<400> SEQUENCE: 13
atggagactt acgtgaacaa gctgcacgag ggttccacct acaccgctgc tgtgcagtac      60
aacgtgatcg agaaggacga cgaccccgct tccctgacca tctgggtgcc catgttccag     120
tcctccatct ccgctgacct gctgatcaag gagctgatca cgtcaacat cctcgtgcgt      180
cagatctcca ccctgaaggg tcccagcctg aagatcatga tcaactcccg ttccgctgtg     240
ctggctcaga tgccctccaa gttcaccatc tccgccaacg tgtccctgga cgagcgttcc     300
aagctggctt acgacatcac caccccctgc gagatcaagg cttgctccct gacctgcctg     360
aaggtcaaga acatgctgac caccgtgaag gacctgacca tgaagacctt caaccccacc     420
cacgagatca tcgctctgtg cgagttcgag aacatcatga cctccaagcg tgtggtcatc     480
cccaccttcc tccgctccat caacgtgaag gctaaggacc tggactccct cgagaacatc     540
gctaccaccg agttcaagaa cgctatcacc aacgctaaga tcatccctta cgctggcctg     600
gtgctggtca tcaccgtgac cgacaacaag ggcgctttca gtacatcaa gccccagtcc      660
cagttcatcg tggacctggg cgcttacctc gagaaggagt ccatctacta cgtcaccacc     720
aactggaagc acaccgctac caagttctcc atcaagccca tcgaggacta a              771

<210> SEQ ID NO 14
<211> LENGTH: 256
<212> TYPE: PRT
<213> ORGANISM: Artificial Sequence
<220> FEATURE:
<223> OTHER INFORMATION: Codon Optimized Bovine RSV M

<400> SEQUENCE: 14

Met Glu Thr Tyr Val Asn Lys Leu His Glu Gly Ser Thr Tyr Thr Ala
1               5                   10                  15

```
Ala Val Gln Tyr Asn Val Ile Glu Lys Asp Asp Pro Ala Ser Leu
             20                  25                  30

Thr Ile Trp Val Pro Met Phe Gln Ser Ser Ile Ser Ala Asp Leu Leu
         35                  40                  45

Ile Lys Glu Leu Ile Asn Val Asn Ile Leu Val Arg Gln Ile Ser Thr
 50                  55                  60

Leu Lys Gly Pro Ser Leu Lys Ile Met Ile Asn Ser Arg Ser Ala Val
 65                  70                  75                  80

Leu Ala Gln Met Pro Ser Lys Phe Thr Ile Ser Ala Asn Val Ser Leu
                 85                  90                  95

Asp Glu Arg Ser Lys Leu Ala Tyr Asp Ile Thr Thr Pro Cys Glu Ile
             100                 105                 110

Lys Ala Cys Ser Leu Thr Cys Leu Lys Val Lys Asn Met Leu Thr Thr
         115                 120                 125

Val Lys Asp Leu Thr Met Lys Thr Phe Asn Pro Thr His Glu Ile Ile
     130                 135                 140

Ala Leu Cys Glu Phe Glu Asn Ile Met Thr Ser Lys Arg Val Val Ile
145                 150                 155                 160

Pro Thr Phe Leu Arg Ser Ile Asn Val Lys Ala Lys Asp Leu Asp Ser
                 165                 170                 175

Leu Glu Asn Ile Ala Thr Thr Glu Phe Lys Asn Ala Ile Thr Asn Ala
             180                 185                 190

Lys Ile Ile Pro Tyr Ala Gly Leu Val Leu Val Ile Thr Val Thr Asp
         195                 200                 205

Asn Lys Gly Ala Phe Lys Tyr Ile Lys Pro Gln Ser Gln Phe Ile Val
210                 215                 220

Asp Leu Gly Ala Tyr Leu Glu Lys Glu Ser Ile Tyr Tyr Val Thr Thr
225                 230                 235                 240

Asn Trp Lys His Thr Ala Thr Lys Phe Ser Ile Lys Pro Ile Glu Asp
                 245                 250                 255

<210> SEQ ID NO 15
<211> LENGTH: 1176
<212> TYPE: DNA
<213> ORGANISM: Respiratory syncytial virus

<400> SEQUENCE: 15
atggctctta gcaaagtcaa gttgaatgat acactcaaca agatcaact  tctgtcatcc      60 agcaaataca ccatccaacg gagcacagga gatagtattg atactcctaa ttatgatgtg     120
cagaaacaca tcaataagtt atgtggcatg ttattaatca cagaagatgc taatcataaa     180
ttcactgggt taataggtat gttatatgcg atgtctaggt taggaagaga agacaccata     240
aaaatactca gagatgcggg atatcatgta aaagcaaatg gagtagatgt aacaacacat     300
cgtcaagaca ttaatggaaa agaaatgaaa tttgaagtgt taacattggc aagcttaaca     360
actgaaattc aaatcaacat tgagatagaa tctagaaaat cctacaaaaa aatgctaaaa     420
gaaatgggag aggtagctcc agaatacagg catgactctc ctgattgtgg gatgataata     480
ttatgtatag cagcattagt aataactaaa ttagcagcag ggacagatc  tggtcttaca     540 gccgtgatta ggagagctaa taatgtccta aaaaatgaaa tgaaacgtta caaaggctta     600
ctacccaagg acatagccaa cagcttctat gaagtgtttg aaaaacatcc cactttata      660 gatgttttg  ttcattttgg tatagcacaa tcttctacca gaggtggcag tagagttgaa     720 gggattttg  caggattgtt tatgaatgcc tatggtgcag gcaagtgat  gttacggtgg     780
```

```
ggagtcttag caaaatcagt taaaaatatt atgttaggac atgctagtgt gcaagcagaa    840
atggaacaag ttgttgaggt ttatgaatat gcccaaaaat tgggtggtga agcaggattc    900
taccatatat tgaacaaccc aaaagcatca ttattatctt tgactcaatt tcctcacttc    960
tccagtgtag tattaggcaa tgctgctggc ctaggcataa tgggagagta cagaggtaca   1020
ccgaggaatc aagatctata tgatgcagca aaggcatatg ctgaacaact caaagaaaat   1080
ggtgtgatta actacagtgt actagacttg acagcagaag aactagaggc tatcaaacat   1140
cagcttaatc caaaagataa tgatgtagag ctttga                              1176
```

<210> SEQ ID NO 16
<211> LENGTH: 391
<212> TYPE: PRT
<213> ORGANISM: Respiratory syncytial virus

<400> SEQUENCE: 16

```
Met Ala Leu Ser Lys Val Lys Leu Asn Asp Thr Leu Asn Lys Asp Gln
1               5                   10

Asn Asn Pro Lys Ala Ser Leu Leu Ser Leu Thr Gln Phe Pro His Phe
305                 310                 315                 320

Ser Ser Val Val Leu Gly Asn Ala Ala Gly Leu Gly Ile Met Gly Glu
            325                 330                 335

Tyr Arg Gly Thr Pro Arg Asn Gln Asp Leu Tyr Asp Ala Ala Lys Ala
            340                 345                 350

Tyr Ala Glu Gln Leu Lys Glu Asn Gly Val Ile Asn Tyr Ser Val Leu
            355                 360                 365

Asp Leu Thr Ala Glu Glu Leu Glu Ala Ile Lys His Gln Leu Asn Pro
370                 375                 380

Lys Asp Asn Asp Val Glu Leu
385                 390

<210> SEQ ID NO 17
<211> LENGTH: 1176
<212> TYPE: DNA
<213> ORGANISM: Artificial Sequence
<220> FEATURE:
<223> OTHER INFORMATION: Codon Optimized RSV N

<400> SEQUENCE: 17
atggctctgt ccaaggtcaa gctgaacgac accctgaaca aggaccagct gctgtcctcc      60
tccaagtaca ccatccagcg ttccaccggt gactccatcg acaccccaa ctacgacgtg      120 cagaagcaca tcaacaagct gtgcggcatg ctgctgatca ccgaggacgc taaccacaag      180
ttcaccggtc tgatcggcat gctgtacgct atgtcccgtc tgggtcgtga ggacaccatc      240
aagatcctgc gtgacgctgg ttaccacgtg aaggctaacg tgtcgacgt gaccacccac      300 cgtcaggaca tcaacggcaa ggagatgaag ttcgaggtcc tgaccctggc ttccctgacc      360
accgagatcc agatcaacat cgagatcgag tcccgtaagt cctacaagaa gatgctgaag      420
gagatgggcg aggtcgcccc cgagtaccgt cacgactccc ccgactgcgg catgatcatc      480
ctgtgcatcg ctgctctcgt catcaccaag ctggctgctg gtgaccgttc cggtctgacc      540
gctgtgatcc gtcgtgctaa caacgtgctg aagaacgaga tgaagcgcta caagggtctg      600
ctgcccaagg acatcgctaa cagcttctac gaggtgttcg agaagcaccc ccacttcatc      660
gacgtgttcg tgcacttcgg tatcgctcag tcctccaccc gtggtggttc cgtgtggag      720 ggcatcttcg ctggtctgtt catgaacgct tacggtgctg ccaggtcat gctgcgttgg      780 ggtgtgctgg ctaagtccgt gaagaacatc atgctgggtc acgcttccgt gcaggctgag      840
atggagcagg tggtggaggt gtacgagtac gctcagaagc tgggcggcga ggctggtttc      900
taccacatcc tgaacaaccc caaggcttcc ctgctgtccc tgacccagtt cccccacttc      960
tcctccgtgg tgctgggtaa cgctgctggt ctgggtatca tgggcgagta ccgtggcacc     1020
ccccgtaacc aggacctgta cgacgctgct aaggcttacg ccgagcagct caaggagaac     1080
ggcgtcatca actactccgt gctggacctg accgctgagg agctggaggc tatcaagcac     1140
cagctgaacc ccaaggacaa cgacgtggag ctgtaa                              1176

<210> SEQ ID NO 18
<211> LENGTH: 391
<212> TYPE: PRT
<213> ORGANISM: Artificial Sequence
<220> FEATURE:
<223> OTHER INFORMATION: Codon Optimized RSV N

<400> SEQUENCE: 18

Met Ala Leu Ser Lys Val Lys Leu Asn Asp Thr Leu Asn Lys Asp Gln

```
            1               5                  10                 15
          Leu Leu Ser Ser Ser Lys Tyr Thr Ile Gln Arg Ser Thr Gly Asp Ser
                          20                  25                 30

Ile Asp Thr Pro Asn Tyr Asp Val Gln Lys His Ile Asn Lys Leu Cys
                          35                  40                  45

Gly Met Leu Leu Ile Thr Glu Asp Ala Asn His Lys Phe Thr Gly Leu
                          50                  55                  60

Ile Gly Met Leu Tyr Ala Met Ser Arg Leu Gly Arg Glu Asp Thr Ile
           65                  70                  75                  80

Lys Ile Leu Arg Asp Ala Gly Tyr His Val Lys Ala Asn Gly Val Asp
                              85                  90                  95

Val Thr Thr His Arg Gln Asp Ile Asn Gly Lys Glu Met Lys Phe Glu
                             100                 105                 110

Val Leu Thr Leu Ala Ser Leu Thr Thr Glu Ile Gln Ile Asn Ile Glu
                             115                 120                 125

Ile Glu Ser Arg Lys Ser Tyr Lys Lys Met Leu Lys Glu Met Gly Glu
                         130                 135                 140

Val Ala Pro Glu Tyr Arg His Asp Ser Pro Asp Cys Gly Met Ile Ile
          145                 150                 155                 160

Leu Cys Ile Ala Ala Leu Val Ile Thr Lys Leu Ala Ala Gly Asp Arg
                             165                 170                 175

Ser Gly Leu Thr Ala Val Ile Arg Arg Ala Asn Asn Val Leu Lys Asn
                         180                 185                 190

Glu Met Lys Arg Tyr Lys Gly Leu Leu Pro Lys Asp Ile Ala Asn Ser
                         195                 200                 205

Phe Tyr Glu Val Phe Glu Lys His Pro His Phe Ile Asp Val Phe Val
          210                 215                 220

His Phe Gly Ile Ala Gln Ser Ser Thr Arg Gly Gly Ser Arg Val Glu
          225                 230                 235                 240

Gly Ile Phe Ala Gly Leu Phe Met Asn Ala Tyr Gly Ala Gly Gln Val
                         245                 250                 255

Met Leu Arg Trp Gly Val Leu Ala Lys Ser Val Lys Asn Ile Met Leu
                         260                 265                 270

Gly His Ala Ser Val Gln Ala Glu Met Glu Gln Val Glu Val Tyr
                     275                 280                 285

Glu Tyr Ala Gln Lys Leu Gly Gly Glu Ala Gly Phe Tyr His Ile Leu
                         290                 295                 300

Asn Asn Pro Lys Ala Ser Leu Leu Ser Leu Thr Gln Phe Pro His Phe
          305                 310                 315                 320

Ser Ser Val Val Leu Gly Asn Ala Ala Gly Leu Gly Ile Met Gly Glu
                             325                 330                 335

Tyr Arg Gly Thr Pro Arg Asn Gln Asp Leu Tyr Asp Ala Ala Lys Ala
                         340                 345                 350

Tyr Ala Glu Gln Leu Lys Glu Asn Gly Val Ile Asn Tyr Ser Val Leu
                         355                 360                 365

Asp Leu Thr Ala Glu Glu Leu Glu Ala Ile Lys His Gln Leu Asn Pro
          370                 375                 380

Lys Asp Asn Asp Val Glu Leu
          385                 390

<210> SEQ ID NO 19
          <211> LENGTH: 1725
          <212> TYPE: DNA
          <213> ORGANISM: Artificial Sequence
```

<220> FEATURE:
<223> OTHER INFORMATION: F protein 368

<400> SEQUENCE: 19

```
atggagctgc tcatcttgaa ggctaacgcc attaccacta tccttacagc ggtgacgttc      60
tgctttgcat ccggtcagaa tattaccgaa gagttctacc aatctacttg tagcgctgtc     120
tcaaaaggct atctatcggc cttacgtaca ggatggtaca cgagtgttat caccatcgaa     180
ctgtccaaca ttaaggagaa taaatgcaac ggtactgacg cgaaggtaaa gctcatcaaa     240
caggaattgg ataagtacaa gaacgcagtg acagagcttc aactgctaat gcagtctacc     300
cccctacga ataaccgcgc taggagagaa ctcccacgat tcatgaacta ctctttaaat     360
aacgccaaaa agaccaacgt cacattgagc aaaaagcgta agcgcaggtt tctgggcttc     420
cttctcggag ttggttcagc tattgcgtcg ggcgtagccg tgagtaaagt cttgcacctg     480
gagggagaag ttaataagat caagtccgca ctcctgtcta ctaacaaagc tgtggtcagc     540
ctatcaaacg gtgtatccgt gttaacctcg aaggttcttg acttgaaaaa ttacatcgat     600
aagcaactcc tgccgattgt caacaagcag agttgttcta tcagcaatat tgagacggtg     660
atcgagttcc aacagaaaaa caacagattg ctggaaatca cacgtgagtt ttcagtaaat     720
gccggcgtta ctaccccgt ctccacgtac atgctaacaa actcggaatt acttagtctc     780
attaacgaca tgcctatcac taatgatcag aagaagttga tgtctaacaa cgtgcaaatt     840
gtccgccagc aaagctattc catcatgtca atcattaaag aggaagtgct ggcgtacgta     900
gttcagctcc cactgtacgg agtcatcgac accccgtgct ggaagctaca tacctcgccc     960
ttatgtacga caaatactaa agagggttct aacatttgcc ttaccaggac ggatcgaggc    1020
tggtattgcg ataacgctgg aagtgtgagc ttcttccctc aagcagaaac atgtaaggta    1080
cagtccaata gagttttttg cgacactatg aactcattga ccctcccatc tgagatcaat    1140
ctgtgtaacg tcgatatctt caacccgaag tacgactgca aaattatgac gtccaagaca    1200
gatgtgtcga gtagcgtaat cacttcacta ggtgccatcg tttcttgcta cggcaagacc    1260
aaatgtacgg cttccaataa gaaccgtgga attatcaaaa cattctcgaa cggttgcgac    1320
tatgtcagca ataagggcat ggacactgtg agtgtaggaa acaccttata ctacgttaac    1380
aagcaagaag gtaaatcact ttatgtcaag ggcgagccca ttatcaatttt ttacgatcct    1440
ttggtgttcc catccgacga gttcgatgcg tctatcagcc aggtaaacga aaagattaac    1500
cagtccctcg catttatccg caaatcggac gagctgctac acaatgttaa cgccggaaag    1560
agtacgacaa acattatgat cactaccatc attatcgtca ttatcgtgat cctttttgtca    1620
ctcattgctg taggtctgtt actatactgt aaagcgaggt ctacgcccgt tacacttagc    1680
aaggatcaat tgtccggcat caataacatt gccttctcga attaa                    1725
```

<210> SEQ ID NO 20
<211> LENGTH: 574
<212> TYPE: PRT
<213> ORGANISM: Artificial Sequence
<220> FEATURE:
<223> OTHER INFORMATION: F protein 368

<400> SEQUENCE: 20

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30
```

-continued

```
Tyr Gln Ser Thr Cys Ser Ala Val Ser Lys Gly Tyr Leu Ser Ala Leu
            35                  40                  45

Arg Thr Gly Trp Tyr Thr Ser Val Ile Thr Ile Glu Leu Ser Asn Ile
 50                  55                  60

Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
                 85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
            115                 120                 125

Leu Ser Lys Lys Arg Lys Arg Arg Phe Leu Gly Phe Leu Leu Gly Val
130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
            210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Ile Asn Leu Cys Asn Val
            370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
            435                 440                 445

Thr Val Ser Val Gly Asn Thr Leu Tyr Tyr Val Asn Lys Gln Glu Gly
```

```
                450                 455                 460
Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
                500                 505                 510

Leu His Asn Val Asn Ala Gly Lys Ser Thr Thr Asn Ile Met Ile Thr
                515                 520                 525

Thr Ile Ile Ile Val Ile Ile Val Ile Leu Ser Leu Ile Ala Val
                530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570

<210> SEQ ID NO 21
<211> LENGTH: 560
<212> TYPE: PRT
<213> ORGANISM: Artificial Sequence
<220> FEATURE:
<223> OTHER INFORMATION: F protein 623

<400> SEQUENCE: 21

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
                20                  25                  30

Tyr Gln Ser Thr Cys Ser Ala Val Ser Lys Gly Tyr Leu Ser Ala Leu
                35                  40                  45

Arg Thr Gly Trp Tyr Thr Ser Val Ile Thr Ile Glu Leu Ser Asn Ile
                50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Asn Asn Glu Leu Pro
                100                 105                 110

Arg Phe Met Asn Tyr Thr Leu Asn Asn Ala Lys Lys Thr Asn Val Thr
                115                 120                 125

Leu Ser Arg Arg Ala Ile Ala Ser Gly Val Ala Val Ser Lys Val Leu
                130                 135                 140

His Leu Glu Gly Glu Val Asn Lys Ile Lys Ser Ala Leu Leu Ser Thr
145                 150                 155                 160

Asn Lys Ala Val Val Ser Leu Ser Asn Gly Val Ser Val Leu Thr Ser
                165                 170                 175

Lys Val Leu Asp Leu Lys Asn His Ile Asp Lys Gln Leu Leu Pro Ile
                180                 185                 190

Val Asn Lys Gln Ser Cys Ser Ile Ser Asn Ile Glu Thr Val Ile Glu
                195                 200                 205

Phe Gln Gln Lys Asn Asn Arg Leu Leu Glu Ile Thr Arg Glu Phe Ser
                210                 215                 220

Val Asn Ala Gly Val Thr Thr Pro Val Ser Thr Tyr Met Leu Thr Asn
225                 230                 235                 240

Ser Glu Leu Leu Ser Leu Ile Asn Asp Met Pro Ile Thr Asn Asp Gln
```

245                 250                 255
Lys Lys Leu Met Ser Asn Asn Val Gln Ile Val Arg Gln Gln Ser Tyr
            260                 265                 270

Ser Ile Met Ser Ile Ile Lys Glu Glu Val Leu Ala Tyr Val Val Gln
            275                 280                 285

Leu Pro Leu Tyr Gly Val Ile Asp Thr Pro Cys Trp Lys Leu His Thr
            290                 295                 300

Ser Pro Leu Cys Thr Thr Asn Thr Lys Glu Gly Ser Asn Ile Cys Leu
305                 310                 315                 320

Thr Arg Thr Asp Arg Gly Trp Tyr Cys Asp Asn Ala Gly Ser Val Ser
                325                 330                 335

Phe Phe Pro Gln Ala Glu Thr Cys Lys Val Gln Ser Asn Arg Val Phe
                340                 345                 350

Cys Asp Thr Met Asn Ser Leu Thr Leu Pro Ser Glu Val Asn Leu Cys
                355                 360                 365

Asn Val Asp Ile Phe Asn Pro Lys Tyr Asp Cys Lys Ile Met Thr Ser
            370                 375                 380

Lys Thr Asp Val Ser Ser Ser Val Ile Thr Ser Leu Gly Ala Ile Val
385                 390                 395                 400

Ser Cys Tyr Gly Lys Thr Lys Cys Thr Ala Ser Asn Lys Asn Arg Gly
                405                 410                 415

Ile Ile Lys Thr Phe Ser Asn Gly Cys Asp Tyr Val Ser Asn Lys Gly
            420                 425                 430

Val Asp Thr Val Ser Val Gly Asn Thr Leu Tyr Tyr Val Asn Lys Gln
                435                 440                 445

Glu Gly Lys Ser Leu Tyr Val Lys Gly Glu Pro Ile Ile Asn Phe Tyr
    450                 455                 460

Asp Pro Leu Val Phe Pro Ser Asp Glu Phe Asp Ala Ser Ile Ser Gln
465                 470                 475                 480

Val Asn Glu Lys Ile Asn Gln Ser Leu Ala Phe Ile Arg Lys Ser Asp
                485                 490                 495

Glu Leu Leu His Asn Val Asn Ala Gly Lys Ser Thr Thr Asn Ile Met
            500                 505                 510

Ile Thr Thr Ile Ile Ile Val Ile Val Ile Leu Ser Leu Ile
        515                 520                 525

Ala Val Gly Leu Leu Leu Tyr Cys Lys Ala Arg Ser Thr Pro Val Thr
            530                 535                 540

Leu Ser Lys Asp Gln Leu Ser Gly Ile Asn Asn Ile Ala Phe Ser Asn
545                 550                 555                 560

<210> SEQ ID NO 22
<211> LENGTH: 252
<212> TYPE: PRT
<213> ORGANISM: Avian influenza virus

<400> SEQUENCE: 22

Met Ser Leu Leu Thr Glu Val Glu Thr Tyr Val Leu Ser Ile Ile Pro
1               5                   10                  15

Ser Gly Pro Leu Lys Ala Glu Ile Ala Gln Lys Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

```
Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Arg Ala
                 85                  90                  95

Val Lys Leu Tyr Lys Lys Leu Lys Arg Glu Ile Thr Phe His Gly Ala
            100                 105                 110

Lys Glu Val Ser Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 23
<211> LENGTH: 4
<212> TYPE: PRT
<213> ORGANISM: Artificial Sequence
<220> FEATURE:
<223> OTHER INFORMATION: Secondary Cleavage Site

<400> SEQUENCE: 23

Arg Ala Arg Arg
1

<210> SEQ ID NO 24
<211> LENGTH: 6
<212> TYPE: PRT
<213> ORGANISM: Artificial Sequence
<220> FEATURE:
<223> OTHER INFORMATION: Primary Cleavage Site

<400> SEQUENCE: 24

Lys Lys Arg Lys Arg Arg
1               5

<210> SEQ ID NO 25
<211> LENGTH: 897
<212> TYPE: DNA
<213> ORGANISM: Artificial Sequence
<220> FEATURE:
<223> OTHER INFORMATION: Codon Optimized RSV G

<400> SEQUENCE: 25
atgtccaaga caaagacca gcgtaccgct aagactctgg agcgcacatg ggatacgctc      60
aatcacttgc ttttcatctc tagctgcctg tacaaactca acttgaagtc agtggcccaa    120
attccccttt cgatcctggc gatgattatc agtactcccc tcatcattgc agctatcatt    180
tttatcgcct ctgcgaatca taaggtcaca cccacgaccg caatcattca ggacgctact    240
```

```
agccaaatca aaaacacaac ccctacgtat ttgactcaga acccacaact gggtatttca    300
ccgtcgaatc ccagtgaaat cacctcccag atcacaacta ttcttgcctc taccacgcct    360
ggcgttaaga gcacactcca atcaactacc gtaaagacga aaaacacaac taccacccag    420
acgcagccat ccaagccgac aactaaacaa aggcagaaca agcccccttc gaagccaaat    480
aacgatttcc acttcgaggt gtttaacttc gtcccgtgta gtatctgctc taataacccc    540
acctgttggg ctatttgcaa agaatccct aacaagaagc caggaaaaaa gacgacaact     600
aaacccacca agaagcctac gttgaaaaca actaagaagg acccgaaacc acaaaccacg    660
aagagcaaag aagttcccac aactaagcct accgaggaac cgacgatcaa tacaactaag    720
accaacatta tcacgacact gctcacttca ataccactg gtaacccaga gctgacctcc      780
cagatggaaa ccttccattc gacgagttct gagggcaacc ccagcccttc ccaagtatca    840
acaacttcgg aatacccatc tcagcccagt agccctccga ataccccacg acaataa       897
```

<210> SEQ ID NO 26
<211> LENGTH: 298
<212> TYPE: PRT
<213> ORGANISM: Artificial Sequence
<220> FEATURE:
<223> OTHER INFORMATION: Codon Optimized RSV G

<400> SEQUENCE: 26

```
Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190

Lys Pro Gly Lys Lys Thr Thr Thr Lys Pro Thr Lys Lys Pro Thr Leu
        195                 200                 205

Lys Thr Thr Lys Lys Asp Pro Lys Pro Gln Thr Thr Lys Ser Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Ser Asn Thr Thr Gly Asn Pro
```

```
                245                 250                 255
Glu Leu Thr Ser Gln Met Glu Thr Phe His Ser Thr Ser Ser Glu Gly
            260                 265                 270

Asn Pro Ser Pro Ser Gln Val Ser Thr Thr Ser Glu Tyr Pro Ser Gln
        275                 280                 285

Pro Ser Ser Pro Pro Asn Thr Pro Arg Gln
    290                 295

<210> SEQ ID NO 27
<211> LENGTH: 65
<212> TYPE: PRT
<213> ORGANISM: Respiratory syncytial virus

<400> SEQUENCE: 27

Met Gly Asn Thr Ser Ile Thr Ile Glu Phe Thr Ser Lys Phe Trp Pro
1               5                   10                  15

Tyr Phe Thr Leu Ile His Met Ile Leu Thr Leu Ile Ser Leu Leu Ile
            20                  25                  30

Ile Ile Thr Ile Met Ile Ala Ile Leu Asn Lys Leu Ser Glu His Lys
        35                  40                  45

Thr Phe Cys Asn Asn Thr Leu Glu Leu Gly Gln Met His Gln Ile Asn
    50                  55                  60

Thr
65

<210> SEQ ID NO 28
<211> LENGTH: 6
<212> TYPE: PRT
<213> ORGANISM: Artificial Sequence
<220> FEATURE:
<223> OTHER INFORMATION: Furin Recognition Site Mutation

<400> SEQUENCE: 28

Lys Lys Gln Lys Gln Gln
1               5

<210> SEQ ID NO 29
<211> LENGTH: 6
<212> TYPE: PRT
<213> ORGANISM: Artificial Sequence
<220> FEATURE:
<223> OTHER INFORMATION: Furin Recognition Site Mutation

<400> SEQUENCE: 29

Gly Arg Arg Gln Gln Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Secondary Cleavage Site

<400> SEQUENCE: 30

Asn Asn Arg Ala Arg Arg Glu Leu Pro
1               5

<210> SEQ ID NO 31
<211> LENGTH: 11
<212> TYPE: PRT
<213> ORGANISM: Artificial Sequence
<220> FEATURE:
```

```
<223> OTHER INFORMATION: Primary Cleavage Site

<400> SEQUENCE: 31

Leu Ser Lys Lys Arg Lys Arg Arg Phe Leu Gly
1               5                   10

<210> SEQ ID NO 32
<211> LENGTH: 6
<212> TYPE: PRT
<213> ORGANISM: Artificial Sequence
<220> FEATURE:
<223> OTHER INFORMATION: Furin Recognition Site Mutation

<400> SEQUENCE: 32

Lys Lys Gln Lys Arg Gln
1               5

<210> SEQ ID NO 33
<211> LENGTH: 4
<212> TYPE: PRT
<213> ORGANISM: Artificial Sequence
<220> FEATURE:
<223> OTHER INFORMATION: Furin Recognition Site Mutation

<400> SEQUENCE: 33

Arg Ala Gln Gln
1

<210> SEQ ID NO 34
<211> LENGTH: 4
<212> TYPE: PRT
<213> ORGANISM: Artificial Sequence
<220> FEATURE:
<223> OTHER INFORMATION: Furin Recognition Site Mutation

<400> SEQUENCE: 34

Arg Ala Asn Asn
1

<210> SEQ ID NO 35
<211> LENGTH: 11
<212> TYPE: PRT
<213> ORGANISM: Artificial Sequence
<220> FEATURE:
<223> OTHER INFORMATION: RSV F protein containing a Furin recognition
      site mutation

<400> SEQUENCE: 35

Leu Ser Lys Lys Gln Lys Gln Gln Phe Leu Gly
1               5                   10
```